United States Patent
Wang et al.

(10) Patent No.: US 7,084,239 B1
(45) Date of Patent: Aug. 1, 2006

(54) CANCER PEPTIDES OF NY-ESO-1/CAG-3

(75) Inventors: Rong Fu Wang, Bethesda, MD (US); Steven Rosenberg, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/529,206

(22) PCT Filed: Sep. 21, 1998

(86) PCT No.: PCT/US98/19609

§ 371 (c)(1),
(2), (4) Date: Jun. 13, 2000

(87) PCT Pub. No.: WO99/18206

PCT Pub. Date: Apr. 15, 1999

Related U.S. Application Data

(60) Provisional application No. 60/061,428, filed on Oct. 8, 1997.

(51) Int. Cl.
| | |
|---|---|
| *A61K 38/00* | (2006.01) |
| *C07K 7/04* | (2006.01) |
| *C07K 7/06* | (2006.01) |
| *C07K 7/08* | (2006.01) |
| *A61K 38/04* | (2006.01) |
| *C07H 21/04* | (2006.01) |
| *C12P 21/06* | (2006.01) |
| *C07K 16/00* | (2006.01) |

(52) U.S. Cl. ............... 530/300; 530/326; 530/327; 530/328; 424/184.1; 424/185.1

(58) Field of Classification Search ............... 530/350, 530/324, 327, 300, 328, 326; 435/69.1; 424/185.1, 424/277.1, 184.1; 514/16
See application file for complete search history.

(56) References Cited

U.S. PATENT DOCUMENTS 5,539,084 A * 7/1996 Geysen
5,785,973 A * 7/1998 Bixler et al.
5,840,839 A * 11/1998 Wang et al.

FOREIGN PATENT DOCUMENTS

| WO | WO 94/03205 | 2/1994 |
| WO | WO 97/29195 | 8/1997 |
| WO | WO 98/14464 | 4/1998 |
| WO | WO 98 32855 | 6/1998 |

OTHER PUBLICATIONS

Burgess et al., J of Cell Bio. 111:2129-2138, 1990.*
Lazar et al. Molecular and Cellular Biology 8:1247-1252, 1988.*
Bowie et al. Science, 247:1306-1310, 1990.*
Chen, et al., 1997, Proc. Natl. Acad. Sci. 94:1914.*
Reiger et al. Glossary of Genetics and Cytogenetics, Classical and Molecular, 4th Ed., Springer-Verlay, Berlin, 1976.*
Riott et al. Immunology, Fourth Edition, 1996, p. 7.9-7.11.*
Le Gal et al. Journal of Immunotherapy, 28(3):252-257, May/Jun. 2005.*
Khong et al. Journal of Immunotherapy, 27(6):472-477, Nov./Dec. 2004.*
Gnjatic et al. Proc. Natl. Acad. Sci. USA, 99(18):11813-11818, 2002.*
Burgess et al. Journal of Cell Biology, 111:2129-2138, Nov. 1990.*
Lazar et al. Molecular and Cellular Biology, 8(3): 1247-1252, Mar. 1988.*
Alberts et al., *Molecular Biology of the Cell*, 3rd Ed., G-12 (1994).
Branden et al., *Introduction to Protein Structure*, 249, (1991).
Estaquier et al., *Eur. J. Immunol.*, 24(11), 2789-2795 (1994), abstract.
Gill et al. *J. Biol. Chem.*, 242, 3308-3318 (1967).

(Continued)

*Primary Examiner*—Sheela Huff
*Assistant Examiner*—David J Blanchard
(74) *Attorney, Agent, or Firm*—Leydig, Voit & Mayer

(57) ABSTRACT

The present invention discloses the identification, isolation and cloning of a gene encoding a novel cancer antigen NY ESO-1CAG-3 and peptides thereof derived from various open reading frames from the NY ESO-1 gene. The novel cancer antigen and peptides are recognized by cytotoxic T lymphocytes in an HLA restricted manner. The products of the gene are promising candidates for immunotherapeutic strategies for the prevention, treatment and diagnosis of patients with cancer.

41 Claims, 16 Drawing Sheets

OTHER PUBLICATIONS

Chen Y.-T., et al. A testicular antigen aberrantly expressed in human cancers detected by autologous antibody screening. Proc. Natl. Acad. Sci. USA 94:1914 (1997).

Jager, E., et al. Simultaneous humoral and cellular immu8ne response against cancer-testis antigen NY-ESO-1: definition of human histocompativility leukocyte antigen (HLA)-A2-binding peptide eptiopes. J. Exp. Med. 187:265 (1998).

Parkhurst, et al. Improved induction of melanoma reactive CTL with peptides from the melanoma antigen gp 100 modified at HLA-A0201 binding residues. J. Immunol. 157:2539 (1996).

Wang, R., et al., A breast and melanoma-shared tumor antigen: T cell responses to antigenic peptides translated from different from different open reading frames. J. Immunol. 161:3596 (1998).

Falk et al. Peptide motifs of HLA-A1, -A11, -A31, and -A33 molecules Immunogenetics, vol. 40: 238-241 (1994).

Kawakami, Y et al. Identification of the Immunodominant Peptides of the MART-1 Human Melanoma Antigen Recognized by the Majority of HLA-A2-restricted Tumor Infiltrating lymphocytes. J. Exp. Med., vol. 180: 347 (1994).

Wang, R-F et al. Identification of a gene encoding a melanoma tumor antigen recognized by HLA-A31-restricted tumor-infiltrating lymphocytes. J. Exp. Med., vol. 181, 799-804 (1995).

Rammensee, H.G. et al. MHC ligand and peptide motifs: first listing, Immunogenetics, vol. 41: 178 (1995).

Wang, R-F, et al. Utilization of an Alternative Open Reading Frame of a Normal Gene in Generating a Novel Human Cancer Antigen, J. Exp. Med. vol. 183: 1131 (1996).

Wang and Rosenberg, Human tumor antigens recognized by T lymphocytes: implications for cancer therapy, J. Leukocyte Biology, vol. 60: 296 (1996).

Wang, R-F et al., Identification of TRP-2 as a Human Tumor Antigen Recognized by cytotoxic T lymphocytes. J. Exp. Med., vol. 184: 2203 (1996).

Kawakami Y et al. Identification of tumor-regression antigens in melanoma. 1. Important Advances in Oncology, 1996, eds. V. DeVita, S. Hellman, S.A. Rosenberg, Lippincott —Raven Publishers, Philadelphia, pp. 3-21.

* cited by examiner

SEQ ID NO:1  AGCAGGGGGCGCTGTGTGTACCGAGAATACGAGAATACCTCGTGGGCCCTGACCTT

SEQ ID NO:2
↓
CTCTCTGAGAGCCGGGCAGAGGCTCCGGAGCCATGCAGGCCGAAGGCCGGGGCACA (SEQ ID NO:4)ORF1▶   M   Q   A   E   G   R   G   T
SEQ ID NO:3
↓
GGGGGTTCGACGGGCGATGCTGATGGCCCAGGAGGCCCTGGCATTCCTGATGGCCC

ORF1▶ G   G   S   T   G   D   A   D   G   P   G   G   P   G   I   P   D   G   P
(SEQ ID NO:5)ORF2▶   M   L   M   A   Q   E   A   L   A   F   L   M   A

AGGGGGCAATGCTGGCGGCCCAGGAGAGGCGGGTGCCACGGGCGGCAGAGGTCCCC

ORF1▶ G   G   N   A   G   G   P   G   E   A   G   A   T   G   G   R   G   P
ORF2▶Q   G   A   M   |L   A   A   Q   E   R   R   V   P   R|   A   A   E   V   P

GGGGCGCAGGGGCAGCAAGGGCCTCGGGGCCGGGAGGAGGCGCCCCGCGGGGTCCG

ORF1▶R   G   A   G   A   A   R   |A   S   G   ?   G   G   G   A   P   R|   G   P
ORF2▶   G   A   Q   G   Q   Q   G   P   R   G   R   E   E   A   P   R   G   V   R

CATGGCGGCGCGGCTTCAGGGCTGAATGGATGCTGCAGATGCGGGGCCAGGGGGCC

ORF1▶ H   G   G   A   A   S   G   L   N   G   C   C   R   C   G   A   R   G   P
ORF2▶   M   A   A   R   L   Q   G

FIG. 3A-1

```
       GGAGAGCCGCCTGCTTGAGTTCTACCTCGCCATGCCTTTCGCGACACCCATGGAAG
ORF1▶  E  S  R  L  L  E  F  Y  L  A  M  P  F  A  T  P  M  E
       CAGAGCTGGCCCGCAGGAGCCTGGCCCAGGATGCCCCACCGCTTCCCGTGCCAGGG
ORF1▶A  E  L  A  R  R  S  L  A  Q  D  A  P  P  L  P  V  P  G
       GTGCTTCTGAAGGAGTTCACTGTGTCCGGCAACATACTGACTATCCGACTCACTGC
ORF1▶  V  L  L  K  E  F  T  V  S  G  N  I  L  T  I  R  L  T  A
       TGCAGACCACCGCCAACTGCAGCTCTCCATCAGCTCCTGTCTCCAGCAGCTTTCCC
ORF1▶  A  D  H  R  Q  L  Q  L  S  I  S  S  C  L  Q  Q  L  S
       TGTTGATGTGGATCACGCAGTGCTTTCTGCCCGTGTTTTTGGCTCAGCCTCCCTCA
ORF1▶L  L  M  W  I  T  Q  C  F  L  P  V  F  L  A  Q  P  P  S
       GGGCAGAGGCGCTAAGCCCAGCCTGGCGCCCCTTCCTAGGTCATGCCTCCTCCCCT
ORF1▶  G  Q  R  R
       AGGGAATGGTCCCAGCACGAGTGGCCAGTTCATTGTGGGGCCTGATTGTTTGTCG
       CTGGAGGAGGACGGCTTACATGTTTGTTTCTGTAGAAAATAAAACTGAGCTACGAA
       AAAAAAAAAAAAAAAAAAAAAA
```

FIG. 3A-2

```
SEQ ID NO:60 ENTF E. coli  894  QAAATGGDARQLVGYLVSQSGL-PLDTSAL--QAQLRETLPPHMVPVVLLQ  941
SEQ ID NO:57                    +  A G ++R  L  YL       P++      +   L +  PP   VP VLL+
SEQ ID NO:55 ESO-ORF1       77  RCGARGPESRLLEFYLAM-PFATPMEAELA--RRSLAQDAPPLPVPGVLLKEFTVSGNITLTIRL  137

SEQ ID NO:58                    +  G  GP + LLEF L M P+ T +     LA  R SLA  A   LP+      +L E ++ G +    +L
SEQ ID NO:61 TEGU HSV11    604  OAGVAGPAAALLEFTLNMLPWKTAVGDFLASTRLSLADVAAHLPLVQHVLDENSLIGRLALAKL  667

SEQ ID NO:56 ESO-ORF2        1  MLMAQEALAFLMAQGAMLAAQERRV  25
SEQ ID NO:59                    M     EAL FLN Q   M+ A  + V
SEQ ID NO:62 GDH C.symb    348  MPTTNEALRFLMQQPNMVVAPSKAV  372
```

FIG. 3B

SEQUENCE LISTING

<160> NUMBER OF SEQ ID NOS: 106

<210> SEQ ID NO 1
<211> LENGTH: 805
<212> TYPE: DNA
<213> ORGANISM: Homo sapiens

<400> SEQUENCE: 1

```
agcaggggc gctgtgtgta ccgagaatac gagaatacct cgtgggccct gaccttctct      60
ctgagagccg ggcagaggct ccggagccat gcaggccgaa ggccggggca caggggttc     120 gacgggcgat gctgatggcc caggaggccc tggcattcct gatggcccag ggggcaatgc    180
tggcggccca ggagaggcgg gtgccacggg cggcagaggt ccccggggcg caggggcagc    240
aagggcctcg gggccgggag gaggcgcccc gcggggtccg catggcggcg cggcttcagg    300
gctgaatgga tgctgcagat gcggggccag ggggccggag agccgcctgc ttgagttcta    360
cctcgccatg cctttcgcga cacccatgga agcagagctg gcccgcagga gcctggccca    420
ggatgcccca ccgcttcccg tgccaggggt gcttctgaag gagttcactg tgtccggcaa    480
catactgact atccgactga ctgctgcaga ccaccgccaa ctgcagctct ccatcagctc    540
ctgtctccag cagctttccc tgttgatgtg gatcacgcag tgctttctgc ccgtgttttt    600
ggctcagcct ccctcagggc agaggcgcta agcccagcct ggcgcccctt cctaggtcat    660
gcctcctccc ctagggaatg gtcccagcac gagtggccag ttcattgtgg gggcctgatt    720
gtttgtcgct ggaggaggac ggcttacatg tttgtttctg tagaaaataa aactgagcta    780
cgaaaaaaaa aaaaaaaaa aaaaa                                            805
```

```
<210> SEQ ID NO 2
<211> LENGTH: 540
<212> TYPE: DNA
<213> ORGANISM: Homo sapiens

<400> SEQUENCE: 2
atgcaggccg aaggccgggg cacagggggt tcgacgggcg atgctgatgg cccaggaggc    60
cctggcattc ctgatggccc aggggcaat  gctggcggcc caggagaggc gggtgccacg   120
ggcggcagag gtccccgggg cgcagggca  gcaagggcct cggggccggg aggaggcgcc   180
ccgcggggtc cgcatggcgg cgcggcttca gggctgaatg gatgctgcag atgcggggcc   240 aggggccgg  agagccgcct gcttgagttc tacctcgcca tgcctttcgc gacacccatg   300
gaagcagagc tggcccgcag gagcctggcc caggatgccc caccgcttcc cgtgccaggg   360
gtgcttctga aggagttcac tgtgtccggc aacatactga ctatccgact gactgctgca   420
gaccaccgcc aactgcagct ctccatcagc tcctgtctcc agcagctttc cctgttgatg   480
tggatcacgc agtgctttct gcccgtgttt ttggctcagc ctccctcagg gcagaggcgc   540

<210> SEQ ID NO 3
<211> LENGTH: 174
<212> TYPE: DNA
<213> ORGANISM: Homo sapiens

<400> SEQUENCE: 3
atgctgatgg cccaggaggc cctggcattc ctgatggccc aggggcaat  gctggcggcc    60 caggagaggc gggtgccacg ggcggcagag gtccccgggg cgcagggca  gcaagggcct   120 cggggccggg aggaggcgcc ccgcggggtc cgcatggcgg cgcggcttca gggc         174

<210> SEQ ID NO 4
<211> LENGTH: 180
<212> TYPE: PRT
<213> ORGANISM: Homo sapiens

<400> SEQUENCE: 4

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Lys Glu Phe Thr Val
            115                 120                 125

Ser Gly Asn Ile Leu Thr Ile Arg Leu Thr Ala Ala Asp His Arg Gln
        130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
```

```
                    165                 170                 175

Gly Gln Arg Arg
            180

<210> SEQ ID NO 5
<211> LENGTH: 58
<212> TYPE: PRT
<213> ORGANISM: Homo sapiens

<400> SEQUENCE: 5

Met Leu Met Ala Gln Glu Ala Leu Ala Phe Leu Met Ala Gln Gly Ala
1               5                   10                  15

Met Leu Ala Ala Gln Glu Arg Arg Val Pro Arg Ala Ala Glu Val Pro
            20                  25                  30

Gly Ala Gln Gly Gln Gly Pro Arg Gly Arg Glu Ala Pro Arg
        35                  40                  45

Gly Val Arg Met Ala Ala Arg Leu Gln Gly
    50                  55

<210> SEQ ID NO 6
<211> LENGTH: 9
<212> TYPE: PRT
<213> ORGANISM: Homo sapiens

<400> SEQUENCE: 6

Ala Gln Pro Pro Ser Gly Gln Arg Arg
1               5

<210> SEQ ID NO 7
<211> LENGTH: 9
<212> TYPE: PRT
<213> ORGANISM: Homo sapiens

<400> SEQUENCE: 7

Thr Pro Met Glu Ala Glu Leu Ala Arg
1               5

<210> SEQ ID NO 8
<211> LENGTH: 9
<212> TYPE: PRT
<213> ORGANISM: Homo sapiens

<400> SEQUENCE: 8

Pro Met Glu Ala Glu Leu Ala Arg Arg
1               5

<210> SEQ ID NO 9
<211> LENGTH: 9
<212> TYPE: PRT
<213> ORGANISM: Homo sapiens

<400> SEQUENCE: 9

Gly Ala Thr Gly Gly Arg Gly Pro Arg
1               5

<210> SEQ ID NO 10
<211> LENGTH: 9
<212> TYPE: PRT
<213> ORGANISM: Homo sapiens

<400> SEQUENCE: 10

Gly Pro Arg Gly Ala Gly Ala Ala Arg
1               5
```

<210> SEQ ID NO 11
<211> LENGTH: 9
<212> TYPE: PRT
<213> ORGANISM: Homo sapiens

<400> SEQUENCE: 11

Leu Ala Gln Pro Pro Ser Gly Gln Arg
1               5

<210> SEQ ID NO 12
<211> LENGTH: 9
<212> TYPE: PRT
<213> ORGANISM: Homo sapiens

<400> SEQUENCE: 12

Val Ser Gly Asn Ile Leu Thr Ile Arg
1               5

<210> SEQ ID NO 13
<211> LENGTH: 9
<212> TYPE: PRT
<213> ORGANISM: Homo sapiens

<400> SEQUENCE: 13

Ile Arg Leu Thr Ala Ala Asp His Arg
1               5

<210> SEQ ID NO 14
<211> LENGTH: 9
<212> TYPE: PRT
<213> ORGANISM: Homo sapiens

<400> SEQUENCE: 14

Ser Gly Pro Gly Gly Gly Ala Pro Arg
1               5

<210> SEQ ID NO 15
<211> LENGTH: 10
<212> TYPE: PRT
<213> ORGANISM: Homo sapiens

<400> SEQUENCE: 15

Thr Val Ser Gly Asn Ile Leu Thr Ile Arg
1               5                   10

<210> SEQ ID NO 16
<211> LENGTH: 10
<212> TYPE: PRT
<213> ORGANISM: Homo sapiens

<400> SEQUENCE: 16

Thr Ile Arg Leu Thr Ala Ala Asp His Arg
1               5                   10

<210> SEQ ID NO 17
<211> LENGTH: 10
<212> TYPE: PRT
<213> ORGANISM: Homo sapiens

<400> SEQUENCE: 17

Ala Thr Pro Met Glu Ala Glu Leu Ala Arg
1               5                   10

```
<210> SEQ ID NO 18
<211> LENGTH: 10
<212> TYPE: PRT
<213> ORGANISM: Homo sapiens

<400> SEQUENCE: 18

Phe Leu Ala Gln Pro Pro Ser Gly Gln Arg
1               5                   10

<210> SEQ ID NO 19
<211> LENGTH: 10
<212> TYPE: PRT
<213> ORGANISM: Homo sapiens

<400> SEQUENCE: 19

Thr Pro Met Glu Ala Glu Leu Ala Arg Arg
1               5                   10

<210> SEQ ID NO 20
<211> LENGTH: 10
<212> TYPE: PRT
<213> ORGANISM: Homo sapiens

<400> SEQUENCE: 20

Arg Cys Gly Ala Arg Gly Pro Glu Ser Arg
1               5                   10

<210> SEQ ID NO 21
<211> LENGTH: 10
<212> TYPE: PRT
<213> ORGANISM: Homo sapiens

<400> SEQUENCE: 21

Ala Ala Ser Gly Leu Asn Gly Cys Cys Arg
1               5                   10

<210> SEQ ID NO 22
<211> LENGTH: 10
<212> TYPE: PRT
<213> ORGANISM: Homo sapiens

<400> SEQUENCE: 22

Leu Ala Gln Pro Pro Ser Gly Gln Arg Arg
1               5                   10

<210> SEQ ID NO 23
<211> LENGTH: 10
<212> TYPE: PRT
<213> ORGANISM: Homo sapiens

<400> SEQUENCE: 23

Arg Gly Pro Arg Gly Ala Gly Ala Ala Arg
1               5                   10

<210> SEQ ID NO 24
<211> LENGTH: 10
<212> TYPE: PRT
<213> ORGANISM: Homo sapiens

<400> SEQUENCE: 24

Leu Asn Gly Cys Cys Arg Cys Gly Ala Arg
1               5                   10

<210> SEQ ID NO 25
<211> LENGTH: 10
```

```
<212> TYPE: PRT
<213> ORGANISM: Homo sapiens

<400> SEQUENCE: 25

Ala Ser Gly Pro Gly Gly Gly Ala Pro Arg
1               5                   10

<210> SEQ ID NO 26
<211> LENGTH: 15
<212> TYPE: PRT
<213> ORGANISM: Homo sapiens

<400> SEQUENCE: 26

Ala Gly Ala Ala Arg Ala Ser Gly Pro Gly Gly Gly Ala Pro Arg
1               5                   10                  15

<210> SEQ ID NO 27
<211> LENGTH: 14
<212> TYPE: PRT
<213> ORGANISM: Homo sapiens

<400> SEQUENCE: 27

Gly Ala Ala Arg Ala Ser Gly Pro Gly Gly Gly Ala Pro Arg
1               5                   10

<210> SEQ ID NO 28
<211> LENGTH: 13
<212> TYPE: PRT
<213> ORGANISM: Homo sapiens

<400> SEQUENCE: 28

Ala Ala Arg Ala Ser Gly Pro Gly Gly Gly Ala Pro Arg
1               5                   10

<210> SEQ ID NO 29
<211> LENGTH: 12
<212> TYPE: PRT
<213> ORGANISM: Homo sapiens

<400> SEQUENCE: 29

Ala Arg Ala Ser Gly Pro Gly Gly Gly Ala Pro Arg
1               5                   10

<210> SEQ ID NO 30
<211> LENGTH: 11
<212> TYPE: PRT
<213> ORGANISM: Homo sapiens

<400> SEQUENCE: 30

Arg Ala Ser Gly Pro Gly Gly Gly Ala Pro Arg
1               5                   10

<210> SEQ ID NO 31
<211> LENGTH: 8
<212> TYPE: PRT
<213> ORGANISM: Homo sapiens

<400> SEQUENCE: 31

Gly Pro Gly Gly Gly Ala Pro Arg
1               5

<210> SEQ ID NO 32
<211> LENGTH: 11
<212> TYPE: PRT
<213> ORGANISM: Homo sapiens
```

```
<400> SEQUENCE: 32

Ala Ser Gly Pro Gly Gly Ala Pro Arg Gly
1               5                   10

<210> SEQ ID NO 33
<211> LENGTH: 10
<212> TYPE: PRT
<213> ORGANISM: Homo sapiens

<400> SEQUENCE: 33

Ser Gly Pro Gly Gly Gly Ala Pro Arg Gly
1               5                   10

<210> SEQ ID NO 34
<211> LENGTH: 10
<212> TYPE: PRT
<213> ORGANISM: Homo sapiens

<400> SEQUENCE: 34

Ala Ala Gly Pro Gly Gly Gly Ala Pro Arg
1               5                   10

<210> SEQ ID NO 35
<211> LENGTH: 10
<212> TYPE: PRT
<213> ORGANISM: Homo sapiens

<400> SEQUENCE: 35

Ala Ile Gly Pro Gly Gly Gly Ala Pro Arg
1               5                   10

<210> SEQ ID NO 36
<211> LENGTH: 10
<212> TYPE: PRT
<213> ORGANISM: Homo sapiens

<400> SEQUENCE: 36

Ala Leu Gly Pro Gly Gly Gly Ala Pro Arg
1               5                   10

<210> SEQ ID NO 37
<211> LENGTH: 10
<212> TYPE: PRT
<213> ORGANISM: Homo sapiens

<400> SEQUENCE: 37

Ala Val Gly Pro Gly Gly Gly Ala Pro Arg
1               5                   10

<210> SEQ ID NO 38
<211> LENGTH: 10
<212> TYPE: PRT
<213> ORGANISM: Homo sapiens

<400> SEQUENCE: 38

Ala Thr Gly Pro Gly Gly Gly Ala Pro Arg
1               5                   10

<210> SEQ ID NO 39
<211> LENGTH: 10
<212> TYPE: PRT
<213> ORGANISM: Homo sapiens

<400> SEQUENCE: 39
```

```
Ala Ser Gly Pro Gly Gly Gly Ala Pro Lys
1               5                   10
```

<210> SEQ ID NO 40
<211> LENGTH: 10
<212> TYPE: PRT
<213> ORGANISM: Homo sapiens

<400> SEQUENCE: 40

```
Ala Ser Gly Pro Gly Gly Gly Ala Pro His
1               5                   10
```

<210> SEQ ID NO 41
<211> LENGTH: 10
<212> TYPE: PRT
<213> ORGANISM: Homo sapiens

<400> SEQUENCE: 41

```
Thr Ser Gly Pro Gly Gly Gly Ala Pro Arg
1               5                   10
```

<210> SEQ ID NO 42
<211> LENGTH: 10
<212> TYPE: PRT
<213> ORGANISM: Homo sapiens

<400> SEQUENCE: 42

```
Val Ser Gly Pro Gly Gly Gly Ala Pro Arg
1               5                   10
```

<210> SEQ ID NO 43
<211> LENGTH: 10
<212> TYPE: PRT
<213> ORGANISM: Homo sapiens

<400> SEQUENCE: 43

```
Leu Ser Gly Pro Gly Gly Gly Ala Pro Arg
1               5                   10
```

<210> SEQ ID NO 44
<211> LENGTH: 10
<212> TYPE: PRT
<213> ORGANISM: Homo sapiens

<400> SEQUENCE: 44

```
Arg Ser Gly Pro Gly Gly Gly Ala Pro Arg
1               5                   10
```

<210> SEQ ID NO 45
<211> LENGTH: 20
<212> TYPE: PRT
<213> ORGANISM: Homo sapiens

<400> SEQUENCE: 45

```
Arg Gly Pro Arg Gly Ala Gly Ala Ala Arg Ala Ser Gly Pro Gly Gly
1               5                   10                  15

Gly Ala Pro Arg
            20
```

<210> SEQ ID NO 46
<211> LENGTH: 9
<212> TYPE: PRT
<213> ORGANISM: Homo sapiens

```
<400> SEQUENCE: 46

Ala Ala Gln Glu Arg Arg Val Pro Arg
1               5

<210> SEQ ID NO 47
<211> LENGTH: 10
<212> TYPE: PRT
<213> ORGANISM: Homo sapiens

<400> SEQUENCE: 47

Leu Ala Ala Gln Glu Arg Arg Val Pro Arg
1               5                   10

<210> SEQ ID NO 48
<211> LENGTH: 11
<212> TYPE: PRT
<213> ORGANISM: Homo sapiens

<400> SEQUENCE: 48

Met Leu Ala Ala Gln Glu Arg Arg Val Pro Arg
1               5                   10

<210> SEQ ID NO 49
<211> LENGTH: 12
<212> TYPE: PRT
<213> ORGANISM: Homo sapiens

<400> SEQUENCE: 49

Ala Met Leu Ala Ala Gln Glu Arg Arg Val Pro Arg
1               5                   10

<210> SEQ ID NO 50
<211> LENGTH: 13
<212> TYPE: PRT
<213> ORGANISM: Homo sapiens

<400> SEQUENCE: 50

Gly Ala Met Leu Ala Ala Gln Glu Arg Arg Val Pro Arg
1               5                   10

<210> SEQ ID NO 51
<211> LENGTH: 30
<212> TYPE: DNA
<213> ORGANISM: Homo sapiens

<400> SEQUENCE: 51
cctcggggcc gggaggaggc gccccgcggg                              30

<210> SEQ ID NO 52
<211> LENGTH: 30
<212> TYPE: DNA
<213> ORGANISM: Homo sapiens

<400> SEQUENCE: 52
ctggcggccc aggagaggcg ggtgccacgg                              30

<210> SEQ ID NO 53
<211> LENGTH: 27
<212> TYPE: DNA
<213> ORGANISM: Homo sapiens

<400> SEQUENCE: 53
gcggcccagg agaggcgggt gccacgg                                 27
```

```
<210> SEQ ID NO 54
<211> LENGTH: 11
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa is no amino acid or one to about 10 amino
      acids
<220> FEATURE:
<221> NAME/KEY: misc_feature
<222> LOCATION: (2)..(2)
<223> OTHER INFORMATION: Xaa is Ala, Thr, Val, Leu or Arg
<220> FEATURE:
<221> NAME/KEY: misc_feature
<222> LOCATION: (3)..(3)
<223> OTHER INFORMATION: Xaa is Ser or conservative substitution
<220> FEATURE:
<221> NAME/KEY: misc_feature
<222> LOCATION: (11)..(11)
<223> OTHER INFORMATION: Xaa is Arg or Lys

<400> SEQUENCE: 54

Xaa Xaa Xaa Gly Pro Gly Gly Gly Ala Pro Xaa
1               5                   10

<210> SEQ ID NO 55
<211> LENGTH: 61
<212> TYPE: PRT
<213> ORGANISM: Homo sapiens

<400> SEQUENCE: 55

Arg Cys Gly Ala Arg Gly Pro Glu Ser Arg Leu Leu Glu Phe Tyr Leu
1               5                   10                  15

Ala Met Pro Phe Ala Thr Pro Met Glu Ala Glu Leu Ala Arg Arg Ser
            20                  25                  30

Leu Ala Gln Asp Ala Pro Pro Leu Pro Val Pro Gly Val Leu Leu Lys
        35                  40                  45

Glu Phe Thr Val Ser Gly Asn Ile Leu Thr Ile Arg Leu
    50                  55                  60

<210> SEQ ID NO 56
<211> LENGTH: 25
<212> TYPE: PRT
<213> ORGANISM: Homo sapiens

<400> SEQUENCE: 56

Met Leu Met Ala Gln Glu Ala Leu Ala Phe Leu Met Ala Gln Gly Ala
1               5                   10                  15

Met Leu Ala Ala Gln Glu Arg Arg Val
            20                  25

<210> SEQ ID NO 57
<211> LENGTH: 15
<212> TYPE: PRT
<213> ORGANISM: Homo sapiens

<400> SEQUENCE: 57

Ala Gly Arg Leu Tyr Leu Pro Leu Pro Pro Val Pro Val Leu Leu
1               5                   10                  15

<210> SEQ ID NO 58
<211> LENGTH: 24
<212> TYPE: PRT
<213> ORGANISM: Homo sapiens
```

```
<400> SEQUENCE: 58

Gly Gly Pro Leu Leu Glu Phe Leu Met Pro Thr Leu Ala Arg Ser Leu
1               5                   10                  15

Ala Ala Leu Pro Leu Glu Gly Leu
            20

<210> SEQ ID NO 59
<211> LENGTH: 11
<212> TYPE: PRT
<213> ORGANISM: Homo sapiens

<400> SEQUENCE: 59

Met Glu Ala Leu Phe Leu Met Gln Met Ala Val
1               5                   10

<210> SEQ ID NO 60
<211> LENGTH: 48
<212> TYPE: PRT
<213> ORGANISM: Homo sapiens

<400> SEQUENCE: 60

Gln Ala Ala Ala Thr Gly Gly Asp Ala Arg Gln Leu Val Gly Tyr Leu
1               5                   10                  15

Val Ser Gln Ser Gly Leu Pro Leu Asp Thr Ser Ala Leu Gln Ala Gln
            20                  25                  30

Leu Arg Glu Thr Leu Pro Pro His Met Val Pro Val Val Leu Leu Gln
        35                  40                  45

<210> SEQ ID NO 61
<211> LENGTH: 64
<212> TYPE: PRT
<213> ORGANISM: Homo sapiens

<400> SEQUENCE: 61

Gln Ala Gly Val Ala Gly Pro Ala Ala Leu Leu Glu Phe Thr Leu
1               5                   10                  15

Asn Met Leu Pro Trp Lys Thr Ala Val Gly Asp Phe Leu Ala Ser Thr
            20                  25                  30

Arg Leu Ser Leu Ala Asp Val Ala Ala His Leu Pro Leu Val Gln His
        35                  40                  45

Val Leu Asp Glu Asn Ser Leu Ile Gly Arg Leu Ala Leu Ala Lys Leu
    50                  55                  60

<210> SEQ ID NO 62
<211> LENGTH: 25
<212> TYPE: PRT
<213> ORGANISM: Homo sapiens

<400> SEQUENCE: 62

Met Pro Thr Thr Asn Glu Ala Leu Arg Phe Leu Met Gln Gln Pro Asn
1               5                   10                  15

Met Val Val Ala Pro Ser Lys Ala Val
            20                  25

<210> SEQ ID NO 63
<211> LENGTH: 9
<212> TYPE: PRT
<213> ORGANISM: Homo sapiens

<400> SEQUENCE: 63

Arg Leu Leu Glu Phe Tyr Leu Ala Met
```

```
1               5
```

<210> SEQ ID NO 64
<211> LENGTH: 9
<212> TYPE: PRT
<213> ORGANISM: Homo sapiens

<400> SEQUENCE: 64

```
Gln Gln Leu Ser Leu Leu Met Trp Ile
1               5
```

<210> SEQ ID NO 65
<211> LENGTH: 9
<212> TYPE: PRT
<213> ORGANISM: Homo sapiens

<400> SEQUENCE: 65

```
Leu Pro Val Pro Gly Val Leu Leu Lys
1               5
```

<210> SEQ ID NO 66
<211> LENGTH: 9
<212> TYPE: PRT
<213> ORGANISM: Homo sapiens

<400> SEQUENCE: 66

```
Gly Val Leu Leu Lys Glu Phe Thr Val
1               5
```

<210> SEQ ID NO 67
<211> LENGTH: 9
<212> TYPE: PRT
<213> ORGANISM: Homo sapiens

<400> SEQUENCE: 67

```
Asn Ile Leu Thr Ile Arg Leu Thr Ala
1               5
```

<210> SEQ ID NO 68
<211> LENGTH: 9
<212> TYPE: PRT
<213> ORGANISM: Homo sapiens

<400> SEQUENCE: 68

```
Trp Ile Thr Gln Cys Phe Leu Pro Val
1               5
```

<210> SEQ ID NO 69
<211> LENGTH: 9
<212> TYPE: PRT
<213> ORGANISM: Homo sapiens

<400> SEQUENCE: 69

```
Thr Val Ser Gly Asn Ile Leu Thr Ile
1               5
```

<210> SEQ ID NO 70
<211> LENGTH: 9
<212> TYPE: PRT
<213> ORGANISM: Homo sapiens

<400> SEQUENCE: 70

```
Leu Gln Gln Leu Ser Leu Leu Met Trp
1               5
```

<210> SEQ ID NO 71
<211> LENGTH: 9
<212> TYPE: PRT
<213> ORGANISM: Homo sapiens

<400> SEQUENCE: 71

Leu Met Trp Ile Thr Gln Cys Phe Leu
1               5

<210> SEQ ID NO 72
<211> LENGTH: 9
<212> TYPE: PRT
<213> ORGANISM: Homo sapiens

<400> SEQUENCE: 72

Leu Leu Met Trp Ile Thr Gln Cys Phe
1               5

<210> SEQ ID NO 73
<211> LENGTH: 9
<212> TYPE: PRT
<213> ORGANISM: Homo sapiens

<400> SEQUENCE: 73

Ile Leu Thr Ile Arg Leu Thr Ala Ala
1               5

<210> SEQ ID NO 74
<211> LENGTH: 9
<212> TYPE: PRT
<213> ORGANISM: Homo sapiens

<400> SEQUENCE: 74

Ser Ile Ser Ser Cys Leu Gln Gln Leu
1               5

<210> SEQ ID NO 75
<211> LENGTH: 9
<212> TYPE: PRT
<213> ORGANISM: Homo sapiens

<400> SEQUENCE: 75

Leu Gln Leu Ser Ile Ser Ser Cys Leu
1               5

<210> SEQ ID NO 76
<211> LENGTH: 9
<212> TYPE: PRT
<213> ORGANISM: Homo sapiens

<400> SEQUENCE: 76

Cys Leu Gln Gln Leu Ser Leu Leu Met
1               5

<210> SEQ ID NO 77
<211> LENGTH: 9
<212> TYPE: PRT
<213> ORGANISM: Homo sapiens

<400> SEQUENCE: 77

Ala Gln Asp Ala Pro Pro Leu Pro Val
1               5

<210> SEQ ID NO 78

-continued

```
<211> LENGTH: 9
<212> TYPE: PRT
<213> ORGANISM: Homo sapiens

<400> SEQUENCE: 78

Gln Cys Phe Leu Pro Val Phe Leu Ala
1               5

<210> SEQ ID NO 79
<211> LENGTH: 9
<212> TYPE: PRT
<213> ORGANISM: Homo sapiens

<400> SEQUENCE: 79

Arg Gln Leu Gln Leu Ser Ile Ser Ser
1               5

<210> SEQ ID NO 80
<211> LENGTH: 9
<212> TYPE: PRT
<213> ORGANISM: Homo sapiens

<400> SEQUENCE: 80

Ser Leu Ala Gln Asp Ala Pro Pro Leu
1               5

<210> SEQ ID NO 81
<211> LENGTH: 9
<212> TYPE: PRT
<213> ORGANISM: Homo sapiens

<400> SEQUENCE: 81

Asn Gly Cys Cys Arg Cys Gly Ala Arg
1               5

<210> SEQ ID NO 82
<211> LENGTH: 9
<212> TYPE: PRT
<213> ORGANISM: Homo sapiens

<400> SEQUENCE: 82

Thr Ile Arg Leu Thr Ala Ala Asp His
1               5

<210> SEQ ID NO 83
<211> LENGTH: 9
<212> TYPE: PRT
<213> ORGANISM: Homo sapiens

<400> SEQUENCE: 83

Ala Ser Gly Leu Asn Gly Cys Cys Arg
1               5

<210> SEQ ID NO 84
<211> LENGTH: 10
<212> TYPE: PRT
<213> ORGANISM: Homo sapiens

<400> SEQUENCE: 84

Thr Val Ser Gly Asn Ile Leu Thr Ile Arg
1               5                   10

<210> SEQ ID NO 85
<211> LENGTH: 10
<212> TYPE: PRT
```

<210> SEQ ID NO 85 (implied continuation)
<213> ORGANISM: Homo sapiens

<400> SEQUENCE: 85

Thr Ile Arg Leu Thr Ala Ala Asp His Arg
1               5                   10

<210> SEQ ID NO 86
<211> LENGTH: 10
<212> TYPE: PRT
<213> ORGANISM: Homo sapiens

<400> SEQUENCE: 86

Thr Gln Cys Phe Leu Pro Val Phe Leu Ala
1               5                   10

<210> SEQ ID NO 87
<211> LENGTH: 10
<212> TYPE: PRT
<213> ORGANISM: Homo sapiens

<400> SEQUENCE: 87

Leu Gln Gln Leu Ser Leu Leu Met Trp Ile
1               5                   10

<210> SEQ ID NO 88
<211> LENGTH: 10
<212> TYPE: PRT
<213> ORGANISM: Homo sapiens

<400> SEQUENCE: 88

Pro Leu Pro Val Pro Gly Val Leu Leu Lys
1               5                   10

<210> SEQ ID NO 89
<211> LENGTH: 10
<212> TYPE: PRT
<213> ORGANISM: Homo sapiens

<400> SEQUENCE: 89

Cys Leu Gln Gln Leu Ser Leu Leu Met Trp
1               5                   10

<210> SEQ ID NO 90
<211> LENGTH: 10
<212> TYPE: PRT
<213> ORGANISM: Homo sapiens

<400> SEQUENCE: 90

Asn Ile Leu Thr Ile Arg Leu Thr Ala Ala
1               5                   10

<210> SEQ ID NO 91
<211> LENGTH: 10
<212> TYPE: PRT
<213> ORGANISM: Homo sapiens

<400> SEQUENCE: 91

Phe Thr Val Ser Gly Asn Ile Leu Thr Ile
1               5                   10

<210> SEQ ID NO 92
<211> LENGTH: 10
<212> TYPE: PRT
<213> ORGANISM: Homo sapiens

```
<400> SEQUENCE: 92

Leu Leu Met Trp Ile Thr Gln Cys Phe Leu
1               5                   10

<210> SEQ ID NO 93
<211> LENGTH: 10
<212> TYPE: PRT
<213> ORGANISM: Homo sapiens

<400> SEQUENCE: 93

Leu Leu Glu Phe Tyr Leu Ala Met Pro Phe
1               5                   10

<210> SEQ ID NO 94
<211> LENGTH: 10
<212> TYPE: PRT
<213> ORGANISM: Homo sapiens

<400> SEQUENCE: 94

Trp Ile Thr Gln Cys Phe Leu Pro Val Phe
1               5                   10

<210> SEQ ID NO 95
<211> LENGTH: 10
<212> TYPE: PRT
<213> ORGANISM: Homo sapiens

<400> SEQUENCE: 95

Ser Leu Leu Met Trp Ile Thr Gln Cys Phe
1               5                   10

<210> SEQ ID NO 96
<211> LENGTH: 10
<212> TYPE: PRT
<213> ORGANISM: Homo sapiens

<400> SEQUENCE: 96

Ala Met Pro Phe Ala Thr Pro Met Glu Ala
1               5                   10

<210> SEQ ID NO 97
<211> LENGTH: 10
<212> TYPE: PRT
<213> ORGANISM: Homo sapiens

<400> SEQUENCE: 97

Gln Gln Leu Ser Leu Leu Met Trp Ile Thr
1               5                   10

<210> SEQ ID NO 98
<211> LENGTH: 10
<212> TYPE: PRT
<213> ORGANISM: Homo sapiens

<400> SEQUENCE: 98

Arg Leu Leu Glu Phe Tyr Leu Ala Met Pro
1               5                   10

<210> SEQ ID NO 99
<211> LENGTH: 10
<212> TYPE: PRT
<213> ORGANISM: Homo sapiens

<400> SEQUENCE: 99
```

Arg Gln Leu Gln Leu Ser Ile Ser Ser Cys
1               5                   10

<210> SEQ ID NO 100
<211> LENGTH: 9
<212> TYPE: PRT
<213> ORGANISM: Homo sapiens

<400> SEQUENCE: 100

Gly Leu Gly Cys Cys Arg Cys Gly Ala
1               5

<210> SEQ ID NO 101
<211> LENGTH: 10
<212> TYPE: PRT
<213> ORGANISM: Homo sapiens

<400> SEQUENCE: 101

Tyr Leu Ala Met Pro Phe Ala Thr Pro Met
1               5                   10

<210> SEQ ID NO 102
<211> LENGTH: 10
<212> TYPE: PRT
<213> ORGANISM: Homo sapiens

<400> SEQUENCE: 102

Gly Ile Pro Asp Gly Pro Gly Gly Asn Ala
1               5                   10

<210> SEQ ID NO 103
<211> LENGTH: 10
<212> TYPE: PRT
<213> ORGANISM: Homo sapiens

<400> SEQUENCE: 103

Gln Leu Gln Leu Ser Ile Ser Ser Cys Leu
1               5                   10

<210> SEQ ID NO 104
<211> LENGTH: 10
<212> TYPE: PRT
<213> ORGANISM: Homo sapiens

<400> SEQUENCE: 104

Leu Thr Ile Arg Leu Thr Ala Ala Asp His
1               5                   10

<210> SEQ ID NO 105
<211> LENGTH: 23
<212> TYPE: DNA
<213> ORGANISM: Homo sapiens

<400> SEQUENCE: 105
gcggcttcag ggctgaatgg atg                                              23

<210> SEQ ID NO 106
<211> LENGTH: 22
<212> TYPE: DNA
<213> ORGANISM: Homo sapiens

<400> SEQUENCE: 106
aagccgtcct cctccagcga ca                                               22

CANCER PEPTIDES OF NY-ESO-1/CAG-3

This patent application is a national stage application of PCT/US98/19609, which was filed on Sep. 21, 1998, which claims priority to U.S. Application No. 60/061,428, which was filed on Oct. 8, 1997.

FIELD OF THE INVENTION

The present invention relates to the area of cancer diagnostics and therapeutics including a cancer vaccine. More specifically, the invention relates to the isolation and purification of a novel human cancer peptide, NY ESO-1/CAG-3, epitopes, and analogs thereof and DNA sequence encoding the cancer peptide or portion thereof. The invention further relates to methods of detecting, diagnosing and treating cancer and precancer in an individual.

BACKGROUND OF THE INVENTION

The adoptive transfer of tumor infiltrating lymphocytes (TIL) can mediate tumor regression in patients with metastatic melanoma, suggesting that tumor rejection antigens recognized by T cells exist on these tumor cells. The availability of such T cells has made it possible to clone and sequence the genes that encode human melanoma antigens. The antigens identified so far from human melanoma can be divided into two classes based on their expression pattern. The antigens of the first class are encoded by genes that are expressed only in tumor and testis, but not other normal human tissues. MAGE1, MAGE3, GAGE and BAGE are examples of this class. The second class of antigens represents differentiation antigens encoded by genes that are expressed only in melanocytes, melanomas, and normal retina. MART-1/Melan-A, gp100 and tyrosine are examples of this class. All these antigens are nonmutated self proteins. However, several mutated antigens were also identified to be recognized by T cells, including CDK 4, B-catenin and Mum-1. Identification of the antigenic epitopes recognized by T cells derived from the corresponding gene products is important not only for understanding the mechanism of immune response to self antigens, but also for developing new, effective immunotherapeutic strategies with these antigens or synthetic peptides for the treatment of patients with cancer.

Previous studies showed that the infusion of TIL586 plus IL-2 into the autologous patient with melanoma resulted in the objective regression of metastases. More recently, the gene, tyrosinase-related protein 1 (TRP-1 or gp75) was cloned which encodes the tumor antigen recognized by TIL586 in association with HLA-A31. Interestingly, the gene product, gp75, was originally identified as an antigen recognized by IgG antibodies in the serum from a patient with metastatic melanoma. The gene was found to be expressed only in melanoma, normal melanocyte cell lines, and retina, but not in other normal tissues tested. Therefore, this gene is a member of the second class of antigens including MART-1/Melan-A, gp100 and tyrosinase.

Wang, R. F. et al *J. Exp. Med.* Vol. 183, pp. 1131–1140 (1996) report on the identification of a cancer peptide encoded from an alternative open reading frame sequence within the TRP-1 gene which is specifically recognized by cloned TIL 586 cells. Wang, R. F. et al *J. Exp. Med.* Vol 184, pp. 2207–2216 (1996) identified a second tumor antigen, TRP-2, recognized by a HLA-A31-restricted CTL clone derived from the TIL 586 cell line.

The present invention is the identification and isolation of novel tumor antigens distinct from TRP-1 and TRP-2 which are recognized by CTL clones derived from the TIL 586 cell line. The cancer peptides of the invention are useful as an immunogen and vaccine to inhibit or prevent cancer in a mammal and as a diagnostic agent to detect cancer or precancer.

SUMMARY OF THE INVENTION

One object of the present invention is to provide a novel peptide and portions thereof recognized as a cancer antigen by T lymphocytes.

The tumor antigen of the present invention and the antigenic cancer peptides of the tumor antigen are encoded by all or a portion of the NY ESO-1/CAG-3 (term used interchangeably herein with CAG-3) gene (SEQ ID NO:1). CAG-3 is a new and potent tumor antigen capable of eliciting an antigen specific immune response by T cells.

One aspect of the invention is cancer peptides encoded by various open reading frames of the CAG-3 gene, or variants thereof, which are useful as a cancer vaccine capable of protecting the recipient from development of cancer. The present invention also relates to a method of administering the cancer vaccine in an effective amount to inhibit or prevent cancers or inhibit the growth of cells expressing the CAG-3 gene product. The CAG-3 gene product may be derived from a normal open reading frames from (ORF-1) or derived from an alternative open reading frame from SEQ. ID NO: 1.

Another aspect of the present invention is a pharmaceutical composition comprising a CAG-3 protein, peptide or antigenic cancer epitope thereof alone or in combination with one or more immunostimulatory molecules. The pharmaceutical composition comprising at least one CAG-3 Epitope, or combination of epitopes stimulate CAG-3 antigen specific T-cells to elicit an immunogenic response against tumors and cancers. The cancer peptide or antigenic cancer epitope thereof may be provided as an immunogen or as a vaccine for prevention or treatment of cancer. The pharmaceutical composition is useful in methods of treating or preventing cancer in a mammal. In the method of treatment, the pharmaceutical composition is administered to the mammal in an amount effective in preventing or inhibiting the cancer in the mammal.

Another object of the present invention is a method of generating CAG-3 cancer peptides and the antigenic cancer epitope within the peptide by translation of DNA sequence encoding same from a CAG-3 gene.

A further aspect of the invention is the DNA or RNA sequence that encodes a CAG-3 cancer peptide or portion thereof and the use of the DNA or RNA sequence in methods of producing the cancer peptide or portions thereof. The invention further provides oligonucleotides of the DNA or RNA sequence for use as probes or primers.

The present invention further provides vectors comprising DNA sequence encoding a CAG-3 cancer peptide or portions thereof alone or in combination with a second DNA sequence encoding at least one immunostimulatory molecule.

The invention also provides host cells transfected or transduced with a vector comprising DNA sequence encoding a CAG-3 cancer peptide or portions thereof alone or in combination with a second DNA sequence encoding at least one immunostimulatory molecule. The vectors and host cells may serve as vaccines in which expression of a cancer peptides results in the stimulation of tumor antigen specific T lymphocytes in a mammal immunized with the vaccine.

The invention provides a method of diagnosis of cancer or precancer in a mammal by detection of a CAG-3 cancer peptide or portions thereof.

It is still another object of the invention to provide a method for diagnosing human preneoplastic and neoplastic cells and tissues. In accordance with the invention, the method comprises isolating cells, tissues or extracts thereof from a human and detecting the DNA sequence, RNA sequence or portion thereof encoding a CAG-3 cancer peptide or portions thereof or detecting the CAG-3 cancer peptide or portions thereof expressed by the DNA sequence or RNA sequence, wherein detection of/or increase in the DNA sequence, RNA sequence or expression product is indicative of preneoplasia and neoplasia.

Still another object of the invention is to provide a transgenic animal which has incorporated into its genome one or more copies of the DNA sequence encoding a CAG-3 cancer peptide or portion thereof. The incorporation of the DNA sequence results in expression or overexpression of the CAG-3 cancer peptide. Such transgenic animals are useful for screening of therapeutic agents useful in treating cancer.

The invention also encompasses antisense oligonucleotides which specifically target and bind to the open reading frame nucleic acid sequence or portion thereof of CAG-3 and inhibit the expression of the cancer peptide or tumor antigen without adversely affecting the expression of the normal protein from the same gene.

Still another aspect of the invention are monoclonal and polyclonal antibodies reactive with the CAG-3 cancer peptide and antigenic cancer epitope thereof, for use in diagnostic and detection assays. The monoclonal and polyclonal antibodies may be provided in the form of a kit alone, or along with other reagents commonly used in diagnostic and detection assays.

BRIEF DESCRIPTION OF THE FIGURES

These and other objects, features, and many of the attendant advantages of the invention will be better understood upon a reading of the following detailed description when considered in connection with the accompanying drawings wherein:

FIG. 3A. Nucleotide and amino acid sequence of NY-ESO-1. FIG. 3A. Numbering of nucleotide sequence of NY-ESO-1 starts from the first nucleotide in the 5' untranslated region. ORF1 represents the gene product of NY-ESO-1, and ORF2 represents a 58-amino acid gene product translated from the ORF2. Antigenic peptides recognized by CTL clone 2 and 5 are boxed. In addition, a peptide poorly recognized by CTL clone 5 is underlined. FIG. 3B. Sequence alignment of the ESO-ORF1 protein with enterobactin synthetase component F (accession g250614) and tegument protein of herpes simplex virus type I (accession p 10220). The residues are numbered with the first start site representing the first amino acid. Alignment of the ESO-ORF2 and glutamate dehydrogenase (accession g1942184) was also shown. The conserved amino acid substitution is indicated by the + symbol.

FIG. 5A. 586EBV or 1510EBV B cells were pulsed with ESO10-53 and ESO9-54 peptides at different concentrations for 120 min. After two washes with AIM-V medium with 120 IU IL-2, CTL clone 5 ($1\times10^5$/well) was added and incubated for 18 to 24 h. GM-CSF release by CTL clone 5 was determined by ELISA. FIG. 5B. 586mel cells were lysed by CTL clone 5, but 397mel cells were not lysed by CTL clone 5 at different E:T ratios. FIG. 5C. 586EBV and 1510EBV B cells were labeled with chromium overnight. The ESO10-53 peptide was then pulsed on the chromium-labeled 586EBV, 1510EBV, and T2 cells for 120 min. An irrelevant peptide containing an HLA-A31 peptide-binding motif was also pulsed on chromium-labeled 586EBV, 1510EBV B cells as negative controls. After peptide incubation and two washes, cytolysis of target cells by CTL clone 5 was determined in a 4-h chromium release assay. T2 pulsed with the ESO10-53 peptide was used for the specificity control.

FIGS. 6B, D, F and H. CTL clones 2, 5, 14, and TIL1244 recognized 586mel. However, CTL clones 2 and 14 did not recognize the ESO10-53 peptide, whereas CTL clone 5 strongly recognized the ESO10-53 peptide when pulsed onto HLA-A31 positive 586EBV B cells. TIL1244 recognized the TRP197-205 peptide derived from TRP-2, 586EBV B cells alone or pulsed with the ORF3P peptide from an alternative reading frame of TRP1 were negative controls. 397mel is an HLA-A31-negative, NY-ESO-1-positive tumor line.

FIG. 7A. Identification of antigenic peptides from the ORF2. Thirty peptides were synthesized based on all potential ORFs and screened. Representative data are shown here. Seven peptides derived from ORF2 (see FIG. 3A) were pulsed on HLA-A31 positive 1510EBV B cells and tested for T cell recognition based on GM-CSF release (GAMLAAQER, SEQ ID NO: 123; AMLAAQERR, SEQ ID NO: 124; PGAQGQQGPR, SEQ ID NO: 125; AAQERRVPR, SEQ ID NO: 46; LAAQERRVPR, SEQ ID NO: 47; GPRGREEAPR, SEQ ID NO: 126; and APRGVRMAAR, SEQ ID NO: 127). 1510 EBV alone was used as a negative control. FIG. 7B. 1510EBV B cells were labeled with chromium for 2 h. The ESORF2-10-18 peptide was then pulsed on the chromium-labeled 1500EBV (solid square) and HLA-A31-negative 1102EBV (open circle) at different concentrations. 1510EBV pulsed with ESO10-53, which was recognized by CTL clone 5, was used for the specificity control (solid triangle). After peptide incubation and three washes, cytolysis of target cells by CTL-clone 2 was determined in a 4-h chromium release assay at an E:T ratio of 20:1. FIG. 7C. Several tumor lines and fresh breast tumors were tested for recognition by CTL clone 2 to determine whether the ORF2 is translated in different tumors. 1510EBV B cells pulsed with ASGPGGGARP (SEQ ID NO: 25) (ESO10-53), LAAQERRVPR (SEQ ID NO: 47) (ORF2-10-18), or alone were included to evaluate the reactivity and specificity of CTL clone 2 and 5. Expression of HLA-A31 on the tumor cells is indicated.

DETAILED DESCRIPTION OF THE INVENTION

Figure 1A:
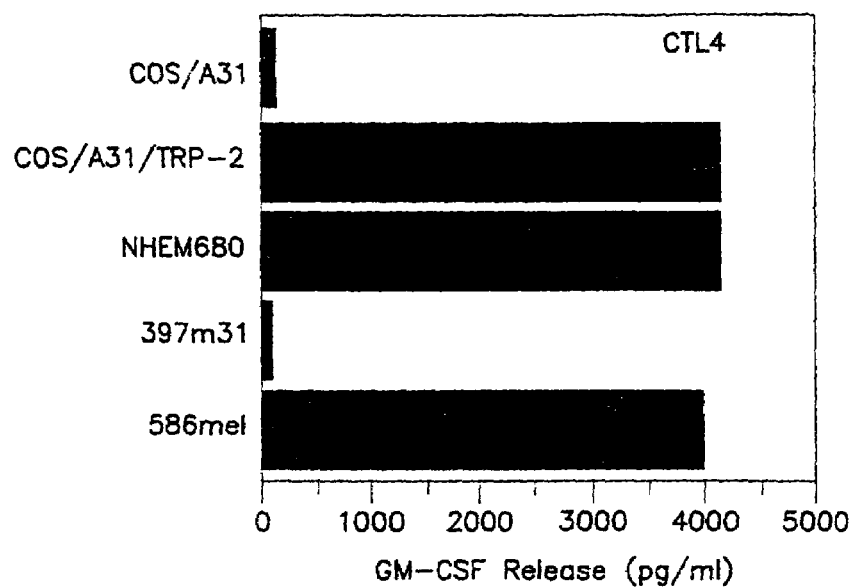
FIGS. 1A through 1C show the GM-CSF release of CTLs cloned from TIL586 in response to stimulation by various antigen expressing cells. CTL clones were isolated by the limiting dilution method and were further expanded. 1A. GM-CSF release by CTL clone 4 was measured after coculturing with different target cells. 1B and 1C. In a separate experiment, GM-CSF release by CTL clones 5 and 10 was determined after coculturing with different stimulators. NHEM680 is a HLA-A31-positive normal melanocyte cell line, 397mel is an HLA-A31-positive normal melanocyte cell line, 397mel is an HLA-A31-negative melanoma cell line and 586mel is an HLA-A31-positive melanoma cell line.

The present invention encompasses cancer peptides, tumor antigen and portion, derivatives or variants thereof which are immunologically recognized by T lymphocytes of the immune system. The present invention further encompasses the antigenic cancer epitope(s) which are contained in the cancer peptides or tumor antigen. The antigenic cancer epitope specifically causes a cellular mediated immune response by interaction with T cells of the immune system. This interaction between the antigenic cancer epitope and the T cells causes the T cells to respond against, and prevent, eliminate or reduce the cancer in a mammal, including humans.

The cancer peptide and portions thereof are characteristically absent from or present in very low levels from normal cells from the majority of tissue sources and are present in high levels from pre-cancer and cancer cells. Expression of the cancer peptide at high levels correlates with transformation of normal cells to a pre-cancer or cancer cell.

The cancer peptides of the present invention form part of, or are derived from, cancers including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, thyroid cancer and the like.

The term melanoma includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome.

Of particular interest are cancer peptides, fragments or derivatives thereof recognized by autologous CTL in patients with cancer, in particular melanoma. Of further interest are cancer peptides, fragments or derivatives thereof recognized by MHC (or HLA) restricted CTL, in particular MHC class I restricted CTLs.

The "tumor antigen" of the present invention encompasses the cancer or tumor protein and any portion or peptide of the cancer or tumor protein capable of eliciting an anti-tumor response in mammals. In one embodiment, the tumor antigen includes the full-length CAG-3 protein. In another embodiment, the tumor or cancer antigen is about 10 amino acids in length.

"Cancer peptides" as the term is used herein, encompasses any epitope or fragment of cancer or tumor protein, which acts as a tumor antigen.

The MHC restricted T lymphocytes are useful in identifying the gene product, CAG-3, associated with cancer and pre-cancer. In one embodiment, a cancer peptide, fragment or derivative thereof of the present invention comprises antigenic cancer epitope immunologically recognized by tumor infiltrating lymphocytes (TIL) derived from a cancer tumor of a mammal. Of particular interest are antigenic cancer epitopes recognized by cancer antigen specific cytotoxic T cells (CD 8$^+$).

In one embodiment, the cancer peptide of the present invention comprises the amino acid sequence:

| MQAEGRGTGG | STGDADGPGG | (SEQ. ID NO: 4) |
|---|---|---|
| PGIPDGPGGN | AGGPGEAGAT | |
| GGRGPRGAGA | ARASGPGGGA | |
| PRGPHGGAAS | GLNGCCRCGA | |
| RGPESRLLEF | YLAMPFATPM | |
| EAELARRSLA | QDAPPLPVPG | |
| VLLKEFTVSG | NILTIRLTAA | |
| DHRQLQLSIS | SCLQQLSLLM | |
| WITQCFLPVF | LAQPPSGQRR | | and cancer epitopes, fragments, or derivatives thereof. Also encompassed in the ambit of the invention are cancer peptides or portions thereof that share partial sequence homology with SEQ. ID NO: 4. By partial amino acid sequence homology is meant a peptide having at least 85% sequence homology with SEQ. ID NO: 4, preferably at least 95% sequence homology or greater and has the biological function of stimulating cancer antigen specific T lymphocytes. Mammalian homologs are included in the ambit of the invention including but not limited to primate and murine homologs.

In an embodiment of the present invention the cancer peptide may be represented by the formula:

Xaa$_1$, Xaa$_2$ Xaa$_3$ GPGGGAPXaa$_4$ (SEQ. ID NO: 54), wherein Xaa$_1$ is no amino acid or one to about 10 amino acids, preferably one to about 5 amino acids, Xaa$_2$ is Ala, Thr, Val, Leu or Arg, Xaa$_3$ is Ser or a conservative substitution such as Ala, Val, Ile, Leu, Thr and the like, Xaa$_4$ is Arg, Lys, preferably Arg and fragments and derivatives thereof.

In one embodiment, the cancer peptide of the present invention comprises the amino acid sequence:

SGPGGGAPR (SEQ. ID NO: 14).

In another embodiment the cancer peptide of the present invention comprises the amino acid sequence:

Position No.

12345678910

ASGPGGGAPR (SEQ. ID NO: 25).

Peptides having substitutions within a sequence ID No: 25 is encompassed by the present invention. In one embodiment the substitution is at position 1, anchor positions 2, 10 or combinations thereof. For example, cancer peptides of the present invention comprise the following amino acid sequences:

ASGPGGGAPK (SEQ. ID NO: 39);
AAGPGGGAPR (SEQ. ID NO: 34);
AIGPGGGAPR (SEQ. ID NO: 35);
ALGPGGGAPR (SEQ. ID NO: 36);

AVGPGGGAPR (SEQ. ID NO: 37);
ATGPGGGAPR (SEQ. ID NO: 38).

In another embodiment, a cancer peptide of the present invention comprises the amino acid sequence:

VSGPGGGAPR (SEQ. ID NO: 42).

Another example of a cancer peptide of the present invention comprises the amino acid sequence:

TSGPGGGAPR (SEQ. ID NO: 41).

Peptides having about 1 to about 10, preferably about 1 to 5 additional amino acids at the N-terminus of SEQ. ID NOS: 14, 25, 34–38, 41 and 42 also form part of the present invention. As an example, a cancer peptide of the present invention having additional amino acids at the N-terminus comprises the amino acid sequence:

AGAARASGPGGGAPR (SEQ. ID NO: 26)

Another example of a cancer peptide of the present invention having additional amino acids at the N-terminus comprises the amino acid sequence:

RGPRGAGAARASGPGGGAPR (SEQ. ID NO: 45)

Another embodiment of the present invention is a cancer peptide comprising the amino acid sequence:

TVSGNILTIR (SEQ. ID NO: 15)

In another embodiment of the invention, the cancer peptide comprises the amino acid sequence:

```
MLMAQEALAF    LMAQGAMLAA    (SEQ. ID NO: 5)
QERRVPRAAE    VPGAQGQQGP
RGREEAPRGV    RMAARLQG
``` and cancer epitopes, fragments, derivatives and homologs thereof. The cancer peptide may be derived from an alternative open reading frame sequence of SEQ. ID NO: 3.

In another embodiment, the cancer peptide comprises the amino acid sequence:

AAQERRVPR (SEQ. ID NO: 46).

In one embodiment, the cancer peptide comprises the amino acid sequence:

Position No.
12345678910
LAAQERRVPR (SEQ. ID NO: 47), and cancer epitopes, fragments, derivatives and homologs thereof. Also included within the ambit of the present invention are cancer peptides of SEQ. ID NO: 47 having an amino acid substitution at position 1, 2, 6, 9 or combination thereof provided the substituted peptide retains functional activity in stimulation cancer peptide specific cytotoxic T lymphocytes.

Also included within the ambit of the present invention is a cancer peptide having one to about 10 additional amino acids, at the N-terminus of SEQ. ID NO: 47, preferably one to about 5 amino acids, more preferably one to about 3 amino acids at the N-terminus of SEQ. ID NO: 47. In one embodiment, cancer peptides of the present invention comprise the amino acid sequences:

MLAAQERRVPR (SEQ. ID NO: 48);
AMLAAQERRVPR (SEQ. ID NO: 49); and
GAMLAAQERRVPR (SEQ. ID NO: 50).

The CAG-3 cancer peptides and the antigenic cancer epitope contained within the tumor antigen of the present invention are expressed in normal testis but not in other normal tissue. The tumor antigen of the present invention present in significantly lower levels in most normal cells as compared to the elevated levels found in pre-cancer and cancer cells. Elevated expression of the tumor antigen correlates with transformation of normal cells to a pre-cancer or cancer cell. CAG-3 is expressed in a variety of cancers including melanoma, breast cancer, prostate cancer, ovarian cancer, lung cancer, thyroid cancer, bladder cancer and liver cancer.

Of further interest are CAG-3 cancer peptides, fragments or derivatives thereof recognized by MHC restricted CTL, in particular MHC class I restricted CTLs. HLA Class I restricted CTLs include but are not limited to HLA-A31, HLA-A3, HLA-A11, HLA-A33 and HLA-A68. A preferred HLA subtype recognized by the CAG-3 cancer peptides is the HLA-A31 subtype.

Another embodiment of the present invention encompasses derivatives and variants of the cancer peptides having sufficient homology to CAG-3 or epitopes thereof to effectively act as cancer peptides. Such peptides may have conservative amino acid changes at one or more positions. By conservative amino acid changes is meant, an amino acid change at a particular position which is of the same type as originally present; i.e. a hydrophobic amino acid exchanged for a hydrophobic amino acid, a basic amino acid for a basic amino acid, etc. Such amino acid changes do not significantly alter the overall charge and configuration of the peptide and therefore such variants maintain or enhance the anti-cancer activity of a cancer peptide. Examples of such conservative changes are well-known to the skilled artisan and are within the scope of the present invention.

The present invention also relates to functionally equivalent variants of the CAG-3 cancer peptides. "Functionally equivalent variants" includes peptides with partial sequence homology, peptides having one or more specific conservative and/or non-conservative amino acid changes, peptide conjugates, chimeric proteins, fusion proteins and peptide nucleic acids.

The CAG-3 cancer peptides, tumor antigen and their antigenic cancer epitopes may be purified and isolated from natural sources such as from primary clinical isolates, cell lines and the like. The CAG-3 cancer peptide and portions thereof are at least 90% pure, preferably at least 95% pure and as pure as 100%. The cancer peptides and their antigenic epitopes may also be obtained by chemical synthesis or by recombinant DNA techniques known in the arts. Techniques for chemical synthesis are described in J. M. Steward and J. D. Young, "Solid Phase Peptide Synthesis", W.H. Freeman & Co., San Francisco, 1969; M. Bodansky et al "Peptide Synthesis", John Wiley & Sons, Second Edition, 1976, and J. Meienhofer, "Hormonal Proteins and Peptides", Vol. 2, p. 46, Academic Press, New York, 1983 and E. Schroder and K. Kubke, "The Peptides", Vol. 1, Academic Press, New York, 1965.

The CAG-3 cancer peptides and their antigenic cancer epitopes may be formulated with pharmaceutically acceptable carriers into pharmaceutical compositions by methods known in the art. The composition is useful as a vaccine to prevent or treat cancer. The composition may further comprise at least one immunostimulatory molecule. Immunostimulatory molecules to be used in conjunction with the cancer peptide or portion thereof for stimulating antigen specific T cell responses include but are not limited to one or more major histocompatibility complex (MHC) molecules, such as class I and class II molecules, preferably a class I molecule. The composition may further comprise other stimulator molecules including B7.1, B7.2, ICAM-1, ICAM-2, LFA-1, LFA-3, CD72 and the like, and cytokines which include but are not limited to IL-1 through IL-15, TNFα, IFNγ, RANTES, G-CSF, M-CSF, IFNα, CTAP III, ENA-78, GRO, I-309, PF-4, IP-10, LD-78, MGSA, MIP-1α, MIP-1β, or combination thereof, and the like for immunopotentiation.

The stimulatory molecule may be provided as a physically separate entity or it may be provided in the membrane of an antigen presenting cell such as B-cell, macrophage or dendritic cell, in the membrane of a liposome, or expressed on the surface of a transduced or transfected cell. DNA sequences of MHC immunostimulatory molecules are available from GenBank and the like.

The CAG-3 cancer peptides, tumor antigen and their antigenic cancer epitopes are useful in methods of preventing or treating cancer and useful in diagnostic assay for detecting cancer or precancer in a mammal, including humans. The cancer peptides or portions thereof may be in the form of a derivative in which other constituents are attached thereto such as radiolabels, biotin, fluorescein. A targeting agent may also be attached to the tumor antigen, cancer peptides or portions thereof that allow for specific targeting to a specific organ, tumor or cell types. Such targeting agents may be hormones, cytokines, cellular receptors and the like. The cancer peptide, tumor antigen and portions thereof may be prepared in the form of a kit, alone or in combination with other reagents.

Another aspect of the invention is a vaccine useful in inducing tumor-specific cell-mediated immunity against cancer.

Approaches to cancer immunotherapy can be divided into active or passive categories. Active immunotherapy involves the direct immunization of cancer patients with cancer antigens in an attempt to boost immune responses against the tumor. Passive immunotherapy refers to the administration of immune reagents, such as immune cells or antibodies with antitumor reactivity with the goal of directly mediating antitumor responses.

Most prior attempts at active immunotherapy utilized either intact cancer cells or cancer cell extracts with the expectation that these materials contained tumor antigens in an amount and form capable of stimulating immune responses. The molecular identification of cancer antigens however, has open new possibilities for developing immunotherapies for the treatment of human cancer. A summary of some of these approaches is presented in Table 1.

TABLE 1

Cancer Therapies Based on the Molecular Identification of Cancer Antigens

1. Active immunotherapy with:

a. Immunodominant peptides 1) alone
      2) combined with adjuvants
      3) linked to helper peptides, lipids or liposomes
      4) pulsed onto antigen presenting cells b. Immunodominant peptides with amino acids substitutions to increase binding to MHC molecules
   c. Proteins alone or combined with adjuvants
   d. "Naked" DNA encoding cancer antigens 1) "gene gun" for intradermal injection
      2) intramuscular injection
      3) linked to lipids e. Recombinant viruses such as vaccinia, fowlpox or adenovirus encoding 1) cancer antigens alone
      2) cancer antigens plus genes encoding cytokines, costimulatory molecules, or other genes to enhance the immune response TABLE 1-continued Cancer Therapies Based on the Molecular Identification of Cancer Antigens f. Recombinant bacteria such as BCG, *Salmonella* or *Listeria* encoding cancer antigens alone or in combination with immunostimulatory molecules 2. Active immunotherapy (above) followed by the administration of immunostimulatory cytokines.

1. IL-2
   2. IL-6
   3. IL-10
   4. IL-12
   5. IL-15, and the like.

3. Passive immunotherapy with anti-tumor lymphocytes raised by in vitro sensitization of TIL or PBL to 1. immunodominant peptides pulsed onto antigen presenting cells (raise CD8 cells)
   2. antigenic proteins coincubated with antigen presenting cells (exogenous antigen presenting pathway to raise CD4 cells).

The insertion of the gene encoding CAG-3 cancer antigens into high efficiency expression systems such as *E. coli*, yeast or baculovirus and the like provides the opportunity to obtain large amounts of purified tumor antigen for use in immunization. Alternatively, the immunodominant peptides from these tumor antigens could readily be synthesized in vitro and purified in large amounts for immunization alone or in a form intended to improve their immunogenicity such as in combination with adjuvant, linkage to lipids/liposomes or helper peptides, or pulsed onto antigen presenting cells. Modification of individual amino acids of the immunodominant peptides to improve binding efficiency to MHC antigens can potentially increase immunogenicity compared to the native peptide.

Recent techniques utilizing "naked" DNA injected directly into muscle or into the skin have been shown to raise both cellular and humoral immune reactions to encoded antigens (Cooney, E. L., A. C. Collier, P. D. Greenberg, R. W. Coombs, J. Zarling, D. E. Arditti, M. C. Hoffman, S. L. Hu and L. Correy, 1991, *Lancet* 337:567; Wolff, J. A., R. W. Malone, P. Williams, W. Chong, G. Acsadi, A. Jani, and P. L. Felgner, 1990, *Science* 247:1465; Davis, H. L., R. G. Whalen, and B. A. Demeniex, 1993, *Hum. Gene Ther.* 4:151; Yang, N. S., J. Burkholder, B. Roberts, B. Martinelli, and D. McCabe, 1990, *Proc. Natl. Acad. Sci. USA* 87:9568; Williams, R. S., S. A. Johnston, M. Riedy, M. J. DeVit, S. G. McElligott, and J. C. Sanford, 1991, *Proc. Natl. Acad. Sci. USA* 88:2726; Fynan, E. R., Webster, D. H. Fuller, J. R. Haynes, J. C. Santoro, and H. L. Robinson, 1995, *Proc. Natl. Acad. Sci. USA* 90:11478; Eisenbraum, M. D., D. H. Fuller, and J. R. Haynes, 1993, DNA and Cell Bio. 12:791; Fuller, D. H. and J. R. Haynes, 1994, *AIDS Res. Hum. Retrovir.* 10(11): 1433; Acsadi, G., G. Dickson, D. R. Love, A. Jani, F. S. Walsh, A. Gurusinghe, J. A. Wolff, and K. E. Davies, 1991, *Nature* 352:815). Techniques using nonviable DNA vectors have the advantage of ease of preparation and safety of administration. The nucleic acid sequence of the present invention is useful as an immunogen and as a DNA vaccine against cancer. The nucleic acid sequence of the present invention of CAG-3 or epitopes thereof may be administered using a gene gun in amounts to elicit a cellular response against a cancer cell. Nomogram quantities are useful for such purposes.

An effective form of immunization involves the incorporation of genes encoding immunogenic molecules into recombinant bacteria such as BCG, *Salmonella* or *Listeria* or into recombinant viruses such as vaccinea, fowlpox or adenovirus and the like. The genes encoding CAG-3 cancer antigens can be expressed either alone or in combination with genes encoding immunostimulatory molecules or other genes which can enhance the immune response following infection. Studies with model tumor antigens in murine models have shown that incorporation of the gene for interleukin-2 (IL-2) or B7.1 can increase the immunogenicity of model tumor antigens and even mediate the regression of established lung metastases bearing these antigens and even mediate the regression of established lung metastases bearing these antigens. Active immunotherapy followed by the exogenous administration of immunostimulatory cytokines such as IL-2, IL-6, IL-10, IL-12, or IL-15 may also be used to improve immune responses.

Passive immunotherapy with genetically modified immune cells (commonly referred to as adoptive immunotherapy) capable of recognizing human tumor antigens is effective in mediating the regression of cancer in selected patients with metastatic melanoma. In vitro techniques have been developed in which human lymphocytes are sensitized in vitro to tumor antigen immunodominant peptides presented on antigen presenting cells. By repetitive in vitro stimulation cells can be derived with a far greater capacity to recognize human tumor antigens than the TIL that were used to clone the genes encoding these antigens. Thus by repeated in vitro sensitization with the cancer peptides, lymphocytes could be derived with 50 to 100 times more potency of TIL. The adoptive transfer of these cells may be more effective in mediating tumor regression in vivo than are conventionally grown TIL.

In the methods of preventing or inhibiting cancer, the cancer peptides or portions thereof may be administered via one of several routes including but not limited to intravenous, intramuscular, subcutaneous, intradermal, intraperitoneal, intrathecal, intrapleural, intrauterine, rectal, vaginal, topical, intratumor and the like.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be by nasal sprays, for example, or suppositories. For oral administration, the cancer peptide, tumor antigen, portion or variant thereof is formulated into conventional oral administration form such as capsules, tablets and toxics.

In general, it is desirable to provide the recipient with a dosage of CAG-3 cancer peptide or portion thereof of at least about 1 pg per Kg bodyweight, preferably at least about 1 ng per Kg bodyweight, more preferably at least about 1 μg or greater per Kg bodyweight of the recipient. A range of from about 1 ng per Kg bodyweight to about 100 mg per Kg bodyweight is preferred although a lower or higher dose may be administered. The dose is effective to prime, stimulate and/or cause the clonal expansion of CAG-3 cancer antigen specific T lymphocytes, preferably cytotoxic T lymphocytes, which in turn are capable of preventing or inhibiting cancer in the recipient.

The dose is administered at least once and may be provided as a bolus or a continuous administration. Multiple administrations of the dose over a period of several weeks to months may be preferable. Subsequent doses may be administered as indicated.

In a method of treatment, a vaccine comprising the CAG-3 cancer peptide or portion thereof is administered to a mammal in an amount effective to prevent cancer in the mammals. Of particular interest is a vaccine comprising SEQ. ID NO: 25, 38, 46, 47 or combination thereof.

In a method of reducing tumor burden in animals having tumors the method comprises administration of an effective amount of a CAG-3 antigenic cancer epitope at a site of tumor burden, said amount is effective to reduce the size of the tumor at the site.

In another method of treatment, autologous cytotoxic lymphocytes or tumor infiltrating lymphocytes may be obtained from a patient with cancer. The lymphocytes are grown in culture and cancer antigen specific lymphocytes expanded by culturing in the presence of specific cancer peptides or antigenic cancer epitopes alone or in combination with at least one immunostimulatory molecule with cytokines. The antigen specific lymphocytes are then infused back into the patient in an amount effective to reduce or eliminate the tumors in the patient.

After immunization the efficacy of the vaccine can be assessed by production of immune cells that recognize the CAG-3 cancer antigen, as assessed by specific lytic activity, specific cytokine production, tumor regression or combination of these. If the mammal to be immunized is already afflicted with cancer or metastasis cancer the vaccine can be administered in conjunction with other therapeutic treatments such as immunomodulators, for example, IL-2, IL-6, IL-10, IL-12, IL-15, interferon, tumor necrosis factor and the like, chemotherapeutic drugs such as cisplatinum, antiviral such as gancyclovir, amphotericin B, antibiotics and the like.

Another aspect of the invention is a DNA sequence of a CAG-3 gene or portion thereof encoding a CAG-3 protein or epitope thereof.

In one embodiment, the DNA sequence comprises SEQ. ID NO.: 1, 2 or 3 portions thereof and functionally equivalent sequence variant thereof that encode a CAG-3 cancer peptide or portions thereof recognized by CAG-3 cancer antigen specific T lymphocytes including tumor infiltrating lymphocytes. Also encompassed by the present invention are nucleic acid sequences complementary, as well as anti-complementary to SEQ. ID NO: 1, 2 or 3.

In another embodiment, the DNA sequence comprises:
CCT CGG GGC CGG GAG GAG GCG CCC CGC GGG (SEQ. ID NO: 51) which encodes SEQ. ID NO: 25.

In another embodiment, gene fragments encoding SEQ. ID NO: 14, 25, 34–38, 41, 42 and functionally equivalent sequence variants thereof are part of the present invention.

Another embodiment of the invention is an alternative open reading frame DNA sequence within SEQ. ID NO: 1 which encodes CAG 3 peptide or epitope thereof. In one embodiment the alternative open reading frame DNA sequence is SEQ. ID NO: 3 as depicted in FIG. 3A which encodes the CAG3 protein, ORF2-SEQ. ID NO: 5, or portion thereof.

In another embodiment, the DNA sequence of the present invention encodes the cancer peptide LAAQERRVPR of SEQ. ID NO: 47, the cancer peptide, AAQERRVPR of SEQ. ID NO: 46, cancer epitopes, fragments, derivatives or homologs thereof.

In one embodiment, the DNA sequnce comprises: CTG GCG GCC CAG GAG AGG CGG GTG CCA CGG (SEQ. ID NO: 52) and variants thereof.

In another embodiment, the DNA sequence comprises:
GCG GCC CAG GAG AGG CGG GTG CCA CGG (SEQ. ID NO: 53)

Due to degeneracy in the generic code, variations in the DNA sequence will result in translation of an equivalent cancer peptide. As a result, substitutions are included in the ambit of the invention as long as the substitution results in expression of a cancer peptide that is recognized by CAG-3 cancer antigen HLA-restricted T cells.

All or part of an open reading frame DNA sequence from the CAG-3 gene may be used as probes to identify and isolate the homologs of the cancer peptide in other mammalian species. In one embodiment, a human cDNA sequence is used to screen a mammalian cDNA library for a murine homolog nucleic acid sequence. Positive clones are selected and sequenced. Examples of tissue sources from which the cDNA library can be synthesized include but are not limited to dermis, epidermis, solid tumors, melanomas, melanocytes, and the like. One skilled in the art will understand the appropriate hybridization conditions to be used to detect the homologs. Conventional methods for nucleic acid hybridization construction of libraries and cloning techniques are described in Sambrook et al, (eds) (1989) in "Molecular Cloning. A Laboratory Manual" Cold Spring Harbor Press, Plainview, N.Y. and Ausubel et al (eds) in "Current Protocols in Molecular Biology" (1987), John Wiley and Sons, New York, N.Y.

Another aspect of the invention are nucleic acid probes for the detection and quantification of RNA that transcribes the CAG-3 cancer peptides or portion thereof in biologic samples isolated from a mammal with cancer. Alterations in the level of RNA relative to a control RNA sample is useful in diagnosis and prognosis of the disease in the mammal.

In one embodiment, mRNA is derived from tissue of a patient suspected of having cancer or precancer and compared with mRNA derived from a healthy control subject. A quantitative and/or qualitative increase of the mRNA encoding a CAG-3 cancer peptide in the patient, as compared to the control, is indicative of cancer or precancer in the patient. The mRNA may be detected using oligonucleotide probes hybridizable with the mRNA. In one embodiment the probe is hybridizable with the transcription product of SEQ. ID NO: 51.

Combinations of oligonucleotides pairs based on the sequence encoding the CAG-3 cancer peptide or portions thereof may be used as PCR primers to detect mRNA in biological samples using the reverse transcriptase polymerase chain reaction (RT-PCR) process for amplifying selected RNA sequences. The present invention also encompasses in situ PCR and in situ RT-PCR for detection of DNA and RNA encoding the CAG-3 cancer peptides or portions thereof. The technique is preferred when the copy number of a target nucleic acid is very low, or when different forms of nucleic acids must be distinguished. The method is especially useful in detecting and differentiating precancer and cancer cells from normal cells.

The present invention also encompasses antisense oligonucleotides which bind to certain complementary ('sense') regions on mRNA resulting in inhibition of synthesis of CAG-3. Such antisense oligonucleotides are single stranded nucleic acid of about 12 to about 25 mononucleotides. Such antisense oligonucleotides may be made by methods known in the art as described by Uhlmann, E. et al. Antisense oligonucleotides, structure and function of In: Molecular Biology and Biotechnology Ed. R. A. Meyers, VCH Publishers, Inc., New York, N.Y., 1995, pp. 38–44.

The present invention also encompasses a vector comprising the DNA sequence encoding CAG-3 cancer peptides or the antigenic cancer epitope. Optionally the vector may also comprise a DNA sequence encoding at least one immunostimulatory molecule. The vector may also contain a gene encoding green fluorescent protein for use in detecting localization of CAG-3 in cells and tissues.

Eukaryotic expression vectors include but are not limited to retroviral vectors, vaccinia virus vectors, adenovirus vectors, herpes virus vectors, fowlpox virus vectors, baculovirus vectors, human papillomavirus vectors, equine encephalitis vectors, influenza virus vectors and the like.

The present invention encompasses novel recombinant virus expressing a CAG-3 cancer peptide or portion thereof encoded by an open reading frame nucleic acid sequence of a gene, fragments or variants thereof. The recombinant virus may also express at least one immunostimulatory molecule. The recombinant virus is capable of eliciting or upregulating a cell-mediate immune response in a mammal for the purpose of preventing or treating cancer in the mammal, particularly humans.

A host cell infected with the recombinant virus expresses the cancer peptide, portion thereof, or antigenic cancer epitope, alone or in combination with at least one immunostimulatory molecule. The host cell may also be infected with a recombinant virus expressing an HLA class I molecule.

Methods for constructing and expressing exogenous gene products from recombinant vaccinia virus vectors are disclosed by Perkus et al *Science* 229:981–984, 1985, Kaufman et al *Int. J. Cancer* 48:900–907, 1991, Moss *Science* 252: 1662, 1991, Smith and Moss *BioTechniques* Nov./Dec., p. 306–312, 1984, and U.S. Pat. No. 4,738,846. Sutter and Moss (*Proc. Nat'l Acad. Sci. U.S.A.* 89:10847–10851, 1992) and Sutter et al (*Virology* 1994) disclose the construction and use as a vector, the non-replicating recombinant Ankara virus (MVA, modified vaccinia Ankara) which may be used as a viral vector in the present invention. Baxby and Paoletti (*Vaccine* 10:8–9, 1992) disclose the construction and use as a vector, a non-replicating poxvirus, including canarypox virus, fowlpox virus and other avian species for use as a viral vector in the present invention.

The vectors of the present invention may be placed in an appropriate host cell for the expression of the CAG-3 cancer peptide or antigenic cancer epitope. Eukaryotic host cell lines include, but are not limited to COS cells, CHO cells, Hela cells, NIH/3T3 cells, insect cells, antigen presenting cells such as dendritic cells and the like. Optionally the host cell may also express a stimulatory molecule. In the case where the host cells express both the cancer peptide or antigenic cancer epitope in combination with at least one MHC (or HLA) molecule, it is preferable that a eukaryotic expression system be used to allow for proper glycosylation. The expression of both the cancer antigen and the immunostimulatory molecule by the host cell provides the necessary MHC restricted peptide to specific T cells and the appropriate signal to the T cell to aid in antigen recognition and proliferation or clonal expansion of antigen specific T cells. The overall result is an upregulation of the immune system. The upregulation of the immune response is manifest by an increase in cancer antigen specific cytotoxic lymphocytes which are able to kill or inhibit the growth of cancer or precancer cells.

The DNA may be inserted into the host cell by transfection, transduction, liposomes and the like by methods known in the art. (Sambrook et al, 1989, in: "Molecular Cloning A Laboratory Manual", Cold Spring Harbor press, Plainview, N.Y.). For liposomes, cationic lipids are preferred, for example, polycationic lipid, dimyristyloxypropyl-3-dimethyl-hydroxyethyl ammonium (DMRIE) complexed with the neutral phospholipid dioleoyl phosphatidyl-ethanolamine (DOPE) as disclosed by Nabel, E. G. et al, 1992, *Hum. Gene. Ther.* 3:367–275; Nabel, G. J. et al, 1992, *Hum. Gene Ther.* 3:649–656; Stewart, M. J. et al 1992 *Hum. Gene Ther.* 3:399–410; Nabel, G. J. et al 1993 *Proc. Natl. Acad. Sci. USA* 90:11307–11311; and Harrison, G. S. et al 1995 *Bio Techniques* 19:816–823.

The recombinant CAG-3 cancer protein, tumor antigen or antigenic cancer epitope expressed by the host cells may be purified from cell lysates or cell supernatants by standard protein purification procedures known in the art. These include but are not limited to molecular sieve chromatography, ion-exchange chromatography, isoelectric focusing, gel electrophoresis, affinity chromatography, HPLC, reverse phase HPLC and the like. (Ausubel et al, 1987, in *Current Protocols in Molecular Biology*, John Wiley and Sons, New York, N.Y.). Immunoaffinity chromatography may also be used for purification using anti-cancer protein antibodies or antigen binding fragments thereof as described herein, as the immunoaffinity agent.

The recombinant virus may also be used as a therapeutic or vaccine. In such uses it is desirable to provide the recipient with a dosage of recombinant virus in the range of from about $10^5$ to about $10^{10}$ plaque forming units/mg mammal, although a lower or higher dose may be administered.

The recombinant viral vector may be introduced into a mammal either prior to any evidence of cancer such as melanoma or to mediate regression of the disease in a mammal afflicted with a cancer such as melanoma. Examples of methods for administering the viral vector into mammals include, but are not limited to, exposure of cells to the recombinant virus ex vivo, or injection of the recombinant virus into the affected tissue or intravenous, subcutaneous, intradermal, intramuscular and the like administration of the virus. Alternatively, the recombinant viral vector or combination of recombinant viral vectors may be administered locally by direct injection into the cancerous lesion or topical application in a suitable pharmaceutically acceptable carrier. The quantity of recombinant viral vector, carrying the nucleic acid sequence of interest is based on the titer of virus particles. A preferred range for immunization is about $10^5$ to $10^{10}$ virus particles per mammal, preferably a human.

The invention provides a transgenic animal which has incorporated into its genome one or more copies of the DNA sequence encoding a CAG-3 cancer peptide or portion thereof. The general method of producing transgenic animals is described in Krimpenfort et al U.S. Pat. No. 5,175,384, Leder et al U.S. Pat. No. 5,175,383, Wagner et al U.S. Pat. No. 5,175,385, Evans et al U.S. Pat. No. 4,870,009 and Berns U.S. Pat. No. 5,174,986. The incorporation of the gene results in overexpression, altered expression or expression of multiple forms or variants of the CAG-3 cancer peptides. The resulting transgenic animal are useful in studies of the development of cancer or tumor antigen of the present invention. The animal model is useful in screening vaccines and chemotherapeutic drugs for cancer treatment. The transgenic animal is also useful in studies of the development of cancer.

This invention further comprises an antibody or antigen binding portion thereof elicited by immunization of the CAG-3 cancer peptide or antigenic cancer epitope of the present invention. In the case where the cancer peptide or antigenic cancer epitope is comprised of only a few amino acids, the cancer peptide or antigenic cancer epitope may be conjugated to a carrier protein in order to elicit an antibody response. Carrier proteins such as KLH, tetanus toxoid and the like and methods of conjugation are known in the art. The antibody has specificity for and reacts or binds with the CAG-3 cancer peptide and the antigenic cancer epitope of the present invention.

Exemplary antibody molecules are intact immunoglobulin molecules, substantially intact immunoglobulin molecules or these portions of an immunoglobulin molecule that contain the antigen binding site, including those portions of immunoglobulin molecules known in the art as F (ab), F (ab'), F (ab')$_2$, humanized chimeric antibody, and F (v). Polyclonal or monoclonal antibodies may be produced by methods known in the art. (Kohler and Milstein (1975) *Nature* 256, 495–497; Campbell "Monoclonal Antibody Technology, the Production and Characterization of Rodent and Human Hybridomas" in Burdon et al (eds.) (1985) "Laboratory Techniques in Biochemistry and Molecular Biology", Vol. 13, Elsevier Science Publishers, Amsterdam). The antibodies or antigen binding fragments may also be produced by genetic engineering. The technology for expression of both heavy and light chain genes is the subject of the PCT patent applications: publication number WO 901443, WO 9014424, Huse et al (1989) *Science* 246: 1275–1281, and U.S. Pat. No. 4,946,778. Humanized immunoglobulins having one or more complementary determining regions and methods of making the antibodies are disclosed in U.S. Pat. Nos. 5,585,089 and 5,530,101.

In one embodiment, the antibodies of the invention are used in immunoassays to detect CAG-3 cancer peptides or portions thereof in biological samples. The antibodies or antigen binding fragments thereof may be used to detect cancer peptides in tissue biopsy samples from a mammal afflicted with cancer. Assessment of the cancer antigen in a diseased tissue can be used to prognose the progression of the disease in a mammal or may diagnose the efficacy of a treatment. The immunoassay may be a radioimmunoassay, Western blot assay, immunofluorescent assay, enzyme immunoassay, chemiluminescent assay, immunohistochemical assay and the like and may be performed in vitro, in vivo or in situ. Standard techniques known in the art for ELISA are described in "Methods in Immunodiagnosis", 2nd Edition, Rose and Bigazzi, eds. John Wiley & Sons, 1980; Campbell et al "Methods and Immunology", W. A. Benjamin, Inc., 1964; and Oellerich, M. 1984, *J. Clin. Chem. Clin. Biochem.* 22:895–904. Conventional methods for immunohistochemistry are described in Harlow and Lane (eds) (1988) In "Antibodies A Laboratory Manual", Cold Spring Harbor Press, Cold Spring Harbor, N.Y.; Ausbel et al (eds) (1987) In Current Protocols In Molecular Biology, John Wiley and Sons (New York, N.Y.). Biological samples appropriate for such detection assays include but are not limited to cells, tissue biopsy, whole blood, plasma, serum, sputum, cerebrospinal fluid, pleural fluid, urine and the like.

The antibodies or antigen binding fragments of the present invention may also be used in immunotherapy. The antibodies or antigen binding fragment thereof is provided to a mammal in an amount sufficient to prevent, lessen or attenuate the severity, extent or duration of the cancer.

All articles and patents referred to are incorporated herein by reference.

While the invention is described above in relation to certain specific embodiments, it will be understood that many variations are possible, and that alternative materials and reagents can be used without departing from the invention. In some cases such variations and substitutions may require some experimentation, but will only involve routine testing.

The foregoing description of the specific embodiments will so fully reveal the general nature of the invention and others can, by applying current knowledge, readily modify and/or adopt for various applications such specific embodiments without departing from the generic concept, and therefore such adaptations and modifications are intended to be comprehended within the meaning and range of equivalents of the disclosed embodiments.

EXAMPLE 1

Materials and Methods

Chemicals and Reagents

The following chemicals and reagents were purchased from the sources indicated: RPMI 1640, AIM-V media, Lipofectamine, G418 (GIBCO BRL, Gaithersberg, Md.); the eukaryotic expression vector pCR3 (Invitrogen, San Diego, Calif.); anti-HLA-A31 monoclonal antibody (One lambda, Canoga Park, Calif.); anti-immunoglobulin M antibody conjugated with fluorescein isothiocyanate (Vector Laboratories, Inc., Burlingame, Calif.).

Cytotoxic T Lymphocytes (CTLs) and Cell Lines

TIL 586 were isolated from the tumor specimen of a patient with metastatic melanoma and grown in medium containing IL-2 (6000 IU/ml) (Chiron) for 32–60 days as previously described (Topalian, S., D. Solomon, F. P. Avis, A. E. Chang, D. L. Freeksen, W. M. Linehan, M. T. Lotze, C. N. Robertson, C. A. Seipp, P. Simon, C. G. Simpson, and S. A. Rosenberg, 1988, *J. Clin. Oncol.* 6:839–53). TIL586 and TIL1244 were predominantly CD8$^+$ T cells. TIL1200 were grown under the same conditions as described for TIL586. TIL1244 recognized the TRP-2 peptide in the context of HLA-A31 and -A33 (31). The T cell clones or cloids were generated by limiting dilution methods (at 1 cell/well) from the TIL586 cell line, using allogeneic PBL ($1 \times 10^3$ cells/well) as feeder cells in RPMI1640 containing 10% human AB sera and 500 IU IL-2. After 12 days, the T cell clones were expanded in AIM-V medium containing 6000 IU/ml IL-2. To obtain an optimal expansion, we used the OKT3 expansion method, described by S. Riddell (32). Briefly, on day 0, $5 \times 10^4$ to $5 \times 10^5$ T cells were cocultured with HLA-A31 $^+$PBL (500:1, PBL:T cell ratio) and 586EBV B cells (100:1, EBV:T cell ratio) in 25 ml of RPMI 1640 containing 11% human sera, 30 ng/ml OKT3 Ab, and antibiotics. On day 1, IL-2 was added at a final concentration of 180 IU/ml. The medium was changed with fresh medium containing 11% human sera and 180 IU/ml IL-2 on day 5. The medium was then changed every 3 days. On days 12 through 14, T cells were harvested, counted and cryopreserved.

Melanoma cell lines 397mel, 397meUA31, 586mel, 624mel, 624mel/A31 and EBV transformed B-cell lines 586EBV and 1510EBV were established in this laboratory and cultured in RPMI 1640 medium containing 10% fetal calf serum (FCS). Normal cultured melanocytes derived from infant foreskin (NHEM680 purchased from Clonetics, Calif.) were cultured in melanocyte growth medium (MGM; Clonetics, Calif.). The COS-7 cell line was provided by Dr. W. Leonard (NIH).

295Br and 1315Br, fresh cryopreserved breast tumor digests, were cleaned with Ficoll gradient before use in T cell assays; 1295 fibroblast were cultured cells from the autologous patient for 22 to 64 days. 1315Br, culture A, were breast tumor cells grown in immunodeficient mice and then cultured in keratinocyte-SFM/2% FCS medium (Life Technologies), and 1315 Br, culture B, were grown in Hams F12/5% FCS for 77 to 80 passages; these cells were kindly provided by Dr. Stephen Ethier, University of Michigan, Ann Arbor, Mich. 1398Br was an human papillomavirus (HPV) E6/E7-immortalized breast tumor line established in the Surgery Branch, National Cancer Institute. Prostate tumor lines 1535Pro, 1542Pro, and 1510 fibroblast were HPV E6/E7-immortalized cell lines.

cDNA Library Construction

Total RNA was extracted from 586mel using Trizol reagent (Life Technologies. Poly(A) RNA was purified from total RNA by the poly AT tract system (Promega, Madison, Wis.) and then converted to cDNA using a cDNA construction kit (Life Technologies) with an oligo(dT) primer containing a NotI site. The cDNA was ligated to BstXI adaptors and digested with NotI, then ligated to the expression vector pcDNA3.1. The cDNA library was electroporated into DH10B cells (Life Technologies). Plasmid DNA pools, each consisting of ~100 cDNA clones, were prepared from bacteria.

cDNA Library Screening and GM-CSF Secretion Assay

DNA transfection and GM-CSF assay were done as previously described (Wang, R. F., P. F. Robbins, Y. Kawakami, X. Q. Kang, and S. A. Rosenberg, 1995, *J. Exp. Med.* 181:799–804). Briefly, 200 μg of DNA carrying a different fragment and 50 ng of the HLA-A31 DNA were mixed with 2 μl of lipofectamine in 100 μl of serum-free DMEM for 15–45 min. The DNA/lipofectamine mixture was then added to the COS-7 ($5 \times 10^4$) cells and incubated overnight. The following day, cells were washed twice with DMEM medium. TIL586, CTL clone 5 or CTL clone 10 were added at a concentration of $5 \times 10^4$ cells/well in AIM-V medium containing 120 IU/ml of IL-2. After 18–24 h incubation, 100 μl of supernatant was collected and GM-CSF was measured in a standard ELISA assay (R+D Systems, Minneapolis, Minn.). For peptides, 586EBV, 1510EBV and T2 cells were incubated with peptides at 37° C. for 90 min, and then washed three times with AIM-V medium containing 120 IU/ml of IL-2. T cells were added and incubated for additional 18–24 h, 100 μl of supernatant was collected for GM-CSF assay. In some experiments, IFN-γ release assays were done using a standard ELISA kit (Endogen, Woburn, Mass.).

Northern Blot Analysis

Total RNA was isolated by the guanidine isothiocyanate/cesium chloride centrifugation method. Total RNA from normal human tissue was purchased from Clontech (Palo Alto, Calif.). Twenty micrograms of total RNA was subjected to electrophoresis in a 1.2% formaldehyde agarose gel and transferred to a nylon membrane. An 0.8-kb DNA fragment of the NY-ESO-1 gene was labeled with [α-$^{32}$P] CTP by the random priming method. Prehybridization and hybridization were performed according to the QuickHyb protocol (Stratagene, La Jolla, Calif.). Membranes were washed twice with 2×SSC/0.1% SCD at room temperature for 15 and twice with 0.1×SSC/0.1% SDS at 60° C. for 30 min. The autoradiography was performed at −70° C.

Reverse Transcriptase-PCR

Total RNA was extracted from tumor cell lines as described above. Five hundred nanograms of total RNA was used for conversion of RNA to cDNA by avian myeloblastosis virus (AMV) reverse transcriptase. cDNA was then amplified by PCR using the ESO-P2 (5'GCGGCT-TCAGGGCTGAATGGATG) SEQ ID NO: 105, and ESO-P5 (5'-AAGCCGTCCTCCTCCAGCGACA) SEQ ID NO: 106, primers and One-Step RT-PCT system (Life Technologies). PCR products were amplified under denaturation conditions at 94° C. for 30 s, annealing at 55° for 30 s, extension at 72° for 3 min for 40 cycles, and final elongation at 72° for 10 min. PCR products were analyzed on a 3% agarose gel.

Cytotoxic Lysis Assays

Cytolytic assay was done as previously described (Kawakami, Y et al., 1994, *Proc. Natl. Acad. Sci. USA* 91:6458–62). Briefly, the target cells were labeled with chromium for 90 min. After washing three times, the cells were incubated with peptides at a concentration of 1 µg/ml for 90 min. The cells were washed again, counted, and then mixed with TIL586 or CTL clone 5 at the indicated ratio of effector: targets (E:T). Chromium release was measured after 4 h incubation. The peptides were synthesized by a solid-phase method using a peptide synthesizer (Model AMS 422, Gilson Co., Inc., Worthington, Ohio). Some peptides were purified by HPLC and had greater than 98% in purity. The mass of some peptides was confirmed by mass spectrometry analysis. For titration of the CAG-3 peptide recognized by TIL586, 586EBV B cells were incubated with various concentrations of the purified CAG-3 peptide or portion thereof. Percentage of specific lysis was determined from the equation $(A-B)/(C-B) \times 100$ where A is lysis of 586EBV B cells by TIL586 or clone 5 in the presence of a peptide, B is spontaneous release from 586EBV B cells in presence of the same peptide but in the absence of effector cells, and C is the maximum chromium release. Cold target inhibition of cytolysis was performed using $^{51}$Cr-labeled 586mel or 624mel cells as "hot" targets and 586EBV B and T2 cells pulsed with peptides as "cold" targets.

EXAMPLE 2

In Vivo Protection Assay

For in vivo protection studies, HLA-A31$^+$ transgenic mice are immunized with), 1 pg, 1 ng, 11 g, 1 mg or 100 mg of cancer peptide (SEQ. ID NO:4, 5, 14, 25, 34–28, 41, 42, 46 or 47), intravenously at day zero and day 14 Before a subcutaneous challenge with $10^4$CAG-3 B16 mouse melanoma cells or intravenous challenge with $5 \times 10^5$ CAG-3 B16 mouse melanoma cells. Mice receiving tumor cells subcutaneously are observed twice a week for tumor development and the size determined. Mice receiving tumor cells intravenously are euthanized on day 12 and the number of lung metastases determined as described by Houghton, A. N. 1994 *J. Exp. Med.* 180: 1–40.

EXAMPLE 3

In Vivo Treatment Assay

For in vivo treatment, HLA-A31$^+$ transgenic mice are challenged with either $1 \times 10^5$ or $5 \times 10^5$ CAG-3 B16 mouse melanoma cells intravenously in order to establish pulmonary metastases. Mice are subsequently vaccinated with a recombinant virus expressing cancer peptide (SEQ. ID NO: 4, 5, 14, 25, 34–28, 41, 42, 46 or 47) AT $10^5$ PFU/mg body weight. Mice are euthanized on day 12 and the number of pulmonary metastases in vaccinated mice vs. non-vaccinated mice determined.

EXAMPLE 4

Cancer Antigen Specific T Lymphocytes Immunotherapy

T-lymphocytes presensitized to a melanoma antigen may be effective in therapeutically treating mammals afflicted with a melanoma. T-lymphocytes are isolated from peripheral blood or melanoma tumor suspensions and cultured in vitro (Kawakami, Y. et al, 1988, *J. Exp. Med.* 168:2183–2191).

The T lymphocytes are exposed to the cancer peptide (SEQ. ID NO: 4, 5, 14, 25, 34–38, 41, 42, 46 or 47) at a concentration of 1 µg/ml alone or in the presence of IL-2, resensitized and expanded in culture. T-lymphocytes exposed to the cancer peptide are administered to a mammal at about $10^9$ to $10^{12}$ lymphocytes per mammal. The lymphocytes are administered either intravenously, intraperitoneally or intralesionally. The treatment may be administered concurrently with other therapeutic treatments such as cytokines, surgical excision of melanoma lesions and chemotherapeutic drugs.

EXAMPLE 5

Treatment of Patients with Metastatic Melanoma

In this protocol, patients with advanced melanoma are immunized with an antigenic cancer epitope.

Patients eligible for the trial must have evidence of measurable or evaluable metastatic melanoma that has failed standard effective therapy. Patients must have tumors that express the CAG-3 antigen as evidenced by PCR or Northern Blot analysis of tumor cell RNA.

Patients receive either 1 ng, 1 µg, 1 mg or 500 mg/kg body weight of a cancer peptide (SEQ. ID NO: 4, 5, 14, 25, 34–38, 41, 42, 46 or 47) via intravenously at day zero, day 7 and day 14 alone or in combination with IL2 and/or an immunostimulatory molecule. Patients are evaluated for toxicity, immunologic effects and therapeutic efficacy.

Lymphocytes taken from the treated patients are tested for specific response to the CAG-3 cancer antigen (SEQ. ID NO: 4, 5, 14, 25, 34–38, 41, 42, 46 or 47).

A complete response is defined as the disappearance of all clinical evidence of disease that lasts at least four weeks. A partial response is a 50% or greater decrease in the sum of the products of the perpendicular diameter of all measurable lesions for at least four weeks with no appearance of new lesions or increase in any lesions. Minor responses are defined as 25–49% decrease in the sum of the products of the perpendicular diameters of all measurable lesions with no appearance of new lesions and no increase in any lesions. Any patient with less than a partial response is considered a non-responder. The appearance of new lesions or greater than 25% increase in the product of perpendicular diameters of prior lesions following a partial or complete response is considered as a relapse.

EXAMPLE 6

Recognition of CAG-3 Antigens on Tumor Cells by CTL Clones

Figure 1B:
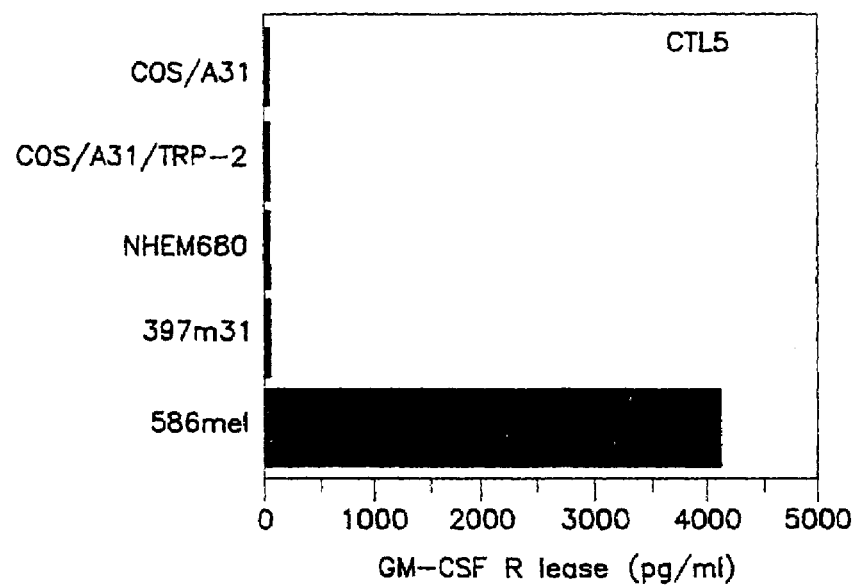
Figure 1C:
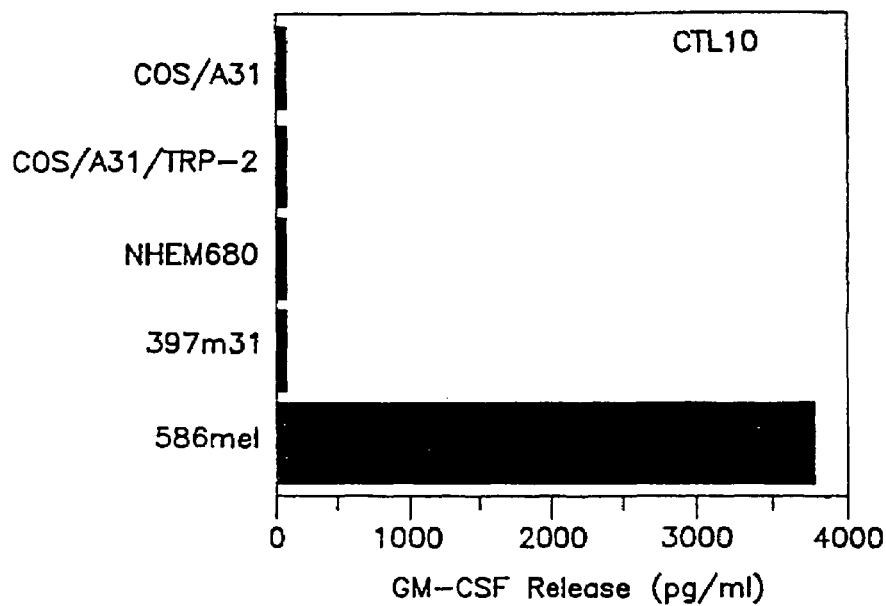

In previous studies, we have isolated a number of T cell clones from the TIL586 Bulk cell line by the limiting dilution method (Wang et al. 1996B, *J. Exp. Med.* 183: 1131–1140). Several clones recognized TRP-1 or TRP-2. However, two T cell clones isolated from the same TIL586 cell line recognized neither TRP-1 or TRP-2 But were capable of recognizing 586mel as well as HLA-A31$^+$ melanocytes (FIGS. 1A through 1C). These results suggested that these T cell clones recognized additional tumor antigens on the 586mel tumor cells. These T cell clones were then expanded and CTL clones 5 and 10 were used to screen cDNA libraries.

EXAMPLE 7

Identification of a cDNA Encoding a Tumor Antigen Recognized by T Cell Clones

To determine the HLA molecule responsible for presenting antigen to CTL clone 5 and 10, we transfected HLA-A31 cDNA into A31-negative tumor lines 397mel and 624mel and tested for recognition by the CTL clone. Transfectants of 397mel and 624mel expressing HLA-A31 were significantly recognized by CTL clone 5 and 10 (Table 1).

TABLE 1

Specific secretion of GM-CSF by CTL clone 5 and 10 is HLA-A31-restricted

| Cell lines | Stimulators Transfected gene | HLA-A31 expression | GM-CSF secretion (pg/ml) clone 5 | clone 10 |
|---|---|---|---|---|
| None | None | − | <50 | <50 |
| 397mel | None | − | <50 | <50 |
| 397mel | HLA-A31 | + | 3840 | 4280 |
| 624mel | None | − | <50 | <50 |
| 624mel | HLA-A31 | + | 4650 | 4320 |
| 586mel | None | + | 4050 | 3900 |
| 586EBVB | None | + | <50 | <50 |

GM-CSF in the supernatant was measured after 24 h incubation of 5 × $10^4$ CTL clone 5 or 10 cells with melanoma cell lines or media alone.

Figure 2:
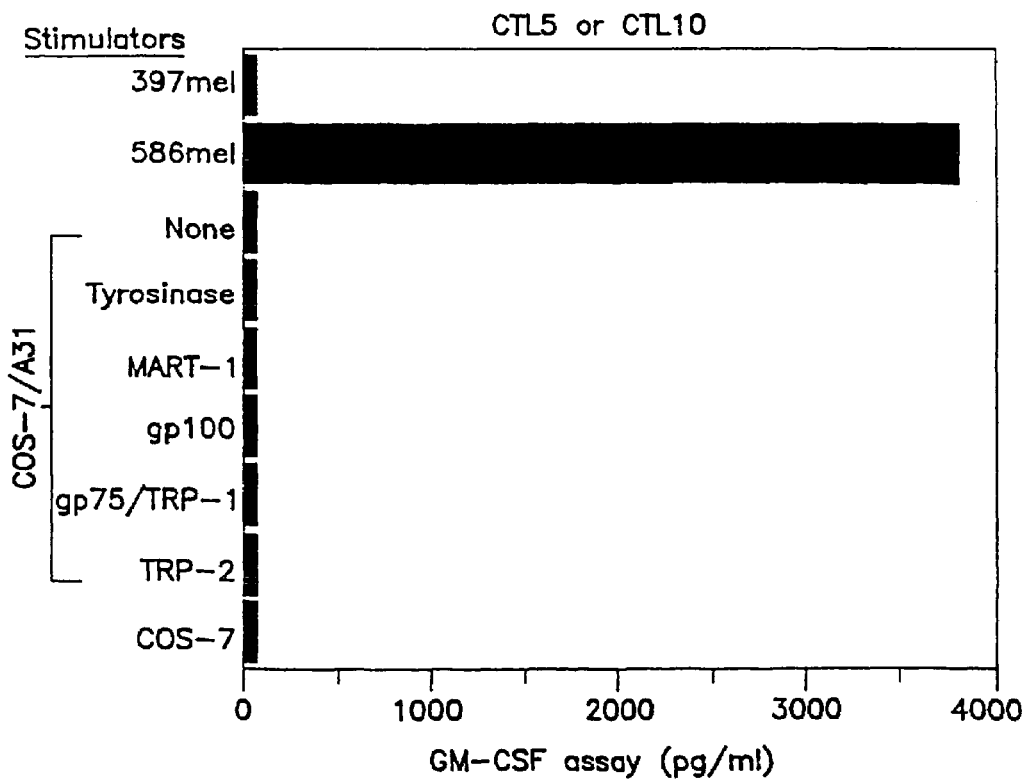
FIG. 2 shows the GM-CSF release of CTL clone 5 and CTL clone 10 in response to stimulation by various known tumor antigens.

Since only a limited number of T cells were available, we first tested whether or not these T cells recognized previously identified tumor antigens or melanocyte-lineage differentiation proteins. Recognition of COS-7 cells transfected with HLA-A31 cDNA and genes encoding the known tumor antigens or putative antigens including MART-1 (Kawakami et al. 1994a, Proc. Nat'l Acad. Sci USA 91:3515–3519), gp75 (Wang et al. 1995, J. Exp. Med. 181:799–804), gp100 (Kawakami et al. 1994B, Proc. Nat'l Acad. Sci. USA 91:6458–6462), tyrosinase (Brichard et al. 1993, J. Exp. Med. 178:489–495), and TRP-2 (Yokoyama et al. 1994, Biochim. Biophys. Acta 1217:317–321; Bouchard et al. 1994, Eur. J. Biochem. 219:127–134) by CTL clone 5 or 10 was tested. COS cells transfected with HLA-A31 alone, TRP-1 or TRP-2 alone did not confer recognition by the T cell clones (FIG. 2). Moreover, COS cells transfected with HLA-A31 and other tumor genes failed to stimulate GM-CSF release from T cells, indicating that the T cell clone 5 or 10 did not recognize these tumor antigens, but recognized a new tumor antigen in the context of HLA-A31.

EXAMPLE 8

Cloning of CAG-3 Gene

Figure 4:
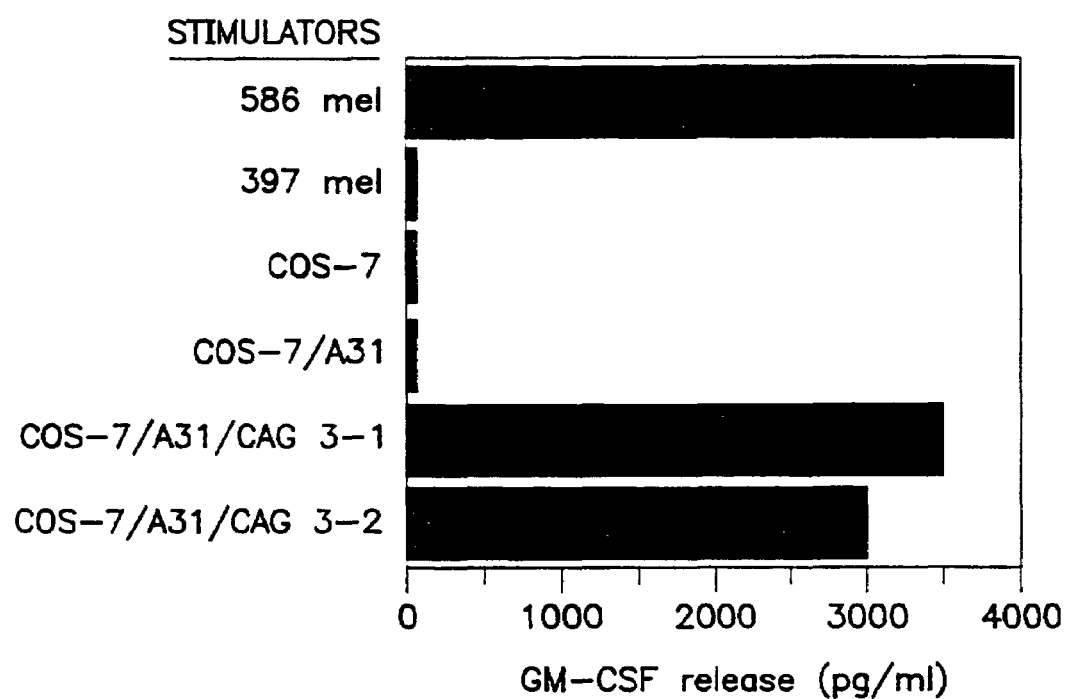
FIG. 4 shows that COS-7 cells transfected with CAG-3 and an HLA-A31 molecule are recognized by CTL clone 5 lymphocytes.

To identify the new tumor Ag(s) recognized by CTL clones 5 and 10, we made a cDNA library derived from 586mel. Each cDNA pool consisted of ~100 cDNA clones. After screening a total of 2.5×10⁵ cDNA clones, we identified 15 positive cDNA pools that conferred T cell recognition by CTL 5 or 10 when cotransfected into COS-7 along with HLA-A31 cDNA. The positive clones were then tested for recognition by both CTL clones 5 and 10. It was found that both CTL clones recognized the same cDNA pools. Individual colonies were isolated from each positive pool and tested for T cell reactivity. Representative data are shown in FIG. 4. CTL clone 5 recognized COS-7 cotransfected with cDNA clone 1 or 2 and HLA-A31, but not COS-7 alone, COS-7 transfected with cDNA clone 1 or 2, or transfected only with the HLA-A31 cDNA (FIG. 4). DNA sequencing analysis indicated that all 10 cDNA positive clones from different positive pools overlapped, and the DNA and the amino acid sequence of these clones is shown in FIG. 3A. A search of all available databases revealed that the coding region of this gene, we named cancer antigen gene 3 (CAG-3, Genbank Accession Number AF038567), was identical to NY-ESO-1 which was recently reported to be an Ag recognized by a serum Ab derived from a patient with esophageal cancer (29). Our longest cDNA clone contained an additional 37 nucleotides upstream of the previously reported 5'-end untranslated region. Two other proteins in the databases were found to contain homologous sequences in a limited region. The gene product of NY-ESO-1 (we have used NY-ESO-1 for CAG-3 in the following text) has 52% similarity to the tegument protein (UL36) of herpes simplex virus type 1 in the 64-amino acid segment and 47% similarity to enterobactin synthetase component F (serine-activating enzyme) in the 48-amino acid region (FIG. 3B).

EXAMPLE 9

Breast Cancer Cells Recognized by CTL Clones

Northern blot analyses were performed using NY-ESO-1 cDNA as a probe to evaluate the expression pattern in different tissues. Testis tissue was shown to be the only positive in the expression of NY-ESO-1 among the normal human tissues tested. NY-ESO-1 was found to be expressed in several types of cancers including melanoma and breast cancer (data not shown). These results were in consistent with data previously reported (29). To determine whether the melanoma reactive CTLs would also recognize other tumor cells, we tested T cell reactivity against HLA-A31 positive breast and prostate tumor cells by CTL clone 5. We used IFN-γ to monitor T cell recognition in these experiments because prostate tumor cells alone secrete GM-CSF, but not IFN-γ. As shown in Table 2, CTL clone 5 was capable of recognizing HLA-A31 positive 1295Br and 1315Br fresh breast tumor cells, but neither HLA-A31 negative 1405Br and 1411Br fresh breast tumor cells, nor HLA-A31 positive 1295 fibroblast cells derived from the autologous patient 1295. In addition, CTL clone 5 recognized the cultured HLA-A31 positive 1315Br (culture A and B) cells (Table 2), but did not respond to the cultured HLA-A31 negative cultured 1386Br breast cancer cells, nor the cultured HLA-A31 positive 1510 fibroblast. Although CTL clone 5 somehow did not respond to the cultured HLA-A31 positive 1315Br (culture A and B) cells in experiment 1, additional experiments showed T cell recognition of the cultured HLA-A31 positive 1315 Br (culture A and B) cells (data not shown). The expression of HLA-A31 and NY-ESO-1 in the fresh 1315Br and 1295Br tumor cells was confirmed by FACS analysis and RT-PCR analysis (data now shown). Expression of NY-ESO-1 was detected by RT-PCR using primers ESO—P2 and ESO—P5 in both 1295 and 1315 fresh breast tumor cells. CTL clone 5 recognized neither the HLA-A31⁺ 1535 prostate tumor cells because of lack of expression of NY-ESO-1 nor the HLA-A31–1542 prostate tumor cells (Table 2). These results strongly suggested that an antigenic peptide of NY-ESO-1 was expressed at sufficient levels on the surface of breast tumor cells to be recognized by T cells. Therefore, NY-ESO-1 may serve as an immune target for the immunotherapy of patients with breast cancer. NY-ESO-1 is also expressed in a high percentage (about 67%) of small cell lung carcinoma (data not shown).

TABLE 2

Recognition of breast tumor cells by CTL clone 5<sup>a</sup>

| Stimulators | | IFNγ release (pg/ml) by CTL | |
|---|---|---|---|
| Target cells | HLA-A31 expression | clone 5 Expt. 1 | Expt. 2 |
| 586mel | + | 225 | 488 |
| 397mel | − | 7 | 35 |
| 1315Br (fresh tumor #1) | + | 171 | 520 |
| 1315Br (fresh tumor #2) | + | 106 | 126 |
| 1295Br (fresh tumor) | + | 265 | 358 |
| 1295 Fibroblast | + | 4 | 24 |
| 1405 Br (fresh tumor) | − | 15 | 28 |
| 1411Br (fresh tumor) | − | ND | 74 |
| 1315Br (culture A) | + | 23 | 224 |
| 1315Br (culture B) | + | 0 | 155 |
| 1398Br | − | 0 | 36 |
| 1510 Fibroblast | + | 8 | ND |
| 1535 Prostate | + | 24 | ND |
| 1542 Prostate | − | 17 | ND |

<sup>a</sup>FN-γ in the supernatant was measured after an 18-h incubation of 1 × 10⁵ CTL clone 5. In experiments 1 and 2 cytokine release from stimulators alone was <10 pg/ml.

EXAMPLE 10

The Peptide Epitopes Recognized by CTL Clone 5

To screen for epitopes from the coding region of CAG-3 DNA an HLA peptide motif search was performed. These results are shown in Table 4 and Table 5.

TABLE 4

HLA peptide motif search results

User Parameters and Scoring Information

| Method selected to limit number of results | explicit number |
|---|---|
| Number of results requested | 30 |
| HLA molecule type selected | A-3101 |
| Length selected for subsequences to be scored | 10 |
| Echoing mode selected for input sequence | Y |
| Echoing format | numbered lines |
| Length of user's input peptide sequence | 180 |
| Number subsequence scores calculated | 171 |
| Number of top-scoring subsequences reported back in scoring output table | 30 |

Scoring Results

| Rank | Start Position | Subsequence Residue Listing | Score (Estimate of Half Time of Disassociation of a Molecule Containing This Subsequence) |
|---|---|---|---|
| 1 | 127 | TVSGnILTIR | 4.000 Seq. ID No. 84 |
| 2 | 134 | TIRLtAADHR | 2.000 Seq. ID No. 85 |
| 3 | 97 | ATPMeAELAR | 2.000 Seq. ID No. 115 |
| 4 | 170 | FLAQpPSGQR | 2.000 Seq. ID No. 116 |
| 5 | 98 | TPMEaELARR | 1.200 Seq. ID No. 117 |
| 6 | 77 | RCGArGPESR | 0.600 Seq. ID No. 118 |
| 7 | 68 | AASG1NGCCR | 0.200 Seq. ID No. 119 |
| 8 | 171 | LAQPpSGQRR | 0.200 Seq. ID No. 120 |
| 9 | 163 | TQCF1PVFLA | 0.120 Seq. ID No. 86 |
| 10 | 153 | LQQLsLLMWI | 0.080 Seq. ID No. 87 |
| 11 | 115 | PLPVpGVLLK | 0.080 Seq. ID No. 88 |
| 12 | 152 | CLQQ1SLLMW | 0.080 Seq. ID No. 89 |
| 13 | 131 | NILTiRLTAA | 0.080 Seq. ID No. 90 |
| 14 | 126 | FTVSgNILTI | 0.080 Seq. ID No. 91 |

TABLE 4-continued

HLA peptide motif search results

| 15 | 43 | RGPRgAGAAR | 0.060 Seq. ID No. 121 |
|---|---|---|---|
| 16 | 158 | LLMWiTQCFL | 0.060 Seq. ID No. 92 |
| 17 | 87 | LLEFyLAMPF | 0.040 Seq. ID No. 93 |
| 18 | 161 | WITQcFLPVF | 0.040 Seq. ID No. 94 |
| 19 | 157 | SLLMwITQCF | 0.040 Seq. ID No. 95 |
| 20 | 93 | AMPFaTPMEA | 0.040 Seq. ID No. 96 |
| 21 | 72 | LNGCcRCGAR | 0.040 Seq. ID No. 122 |
| 22 | 154 | QQLS1LMWIT | 0.040 Seq. ID No. 97 |
| 23 | 86 | RLLEfYLAMP | 0.024 Seq. ID No. 98 |
| 24 | 143 | RQLQ1SISSC | 0.024 Seq. ID No. 99 |
| 25 | 71 | GLNGcCRCGA | 0.020 Seq. ID No. 100 |
| 26 | 91 | YLAMpFATPM | 0.020 Seq. ID No. 101 |
| 27 | 22 | GIPDgPGGNA | 0.020 Seq. ID No. 102 |
| 28 | 53 | ASGPgGGAPR | 0.020 Seq. ID No. 25 |
| 29 | 144 | QLQLsISSCL | 0.020 Seq. ID No. 103 |
| 30 | 133 | LTIR1TAADH | 0.020 Seq. ID No. 104 |

TABLE 5

HLA peptide motif search results

User Parameters and Scoring Information

| Method selected to limit number of results | explicit number |
|---|---|
| Number of results requested | 30 |
| HLA molecule type selected | A-3101 |
| Length selected for subsequences to be scored | 9 |
| Echoing mode selected for input sequence | Y |
| Echoing format | numbered lines |
| Length of user's input peptide sequence | 181 |
| Number subsequence scores calculated | 173 |
| Number of top-scoring subsequences reported back in scoring output table | 30 |

Scoring Results

| Rank | Start Position | Subsequence Residue Listing | Score (Estimate of Half Time of Disassociation of a Molecule Containing This Subsequence) |
|---|---|---|---|
| 1 | 172 | AQPPSGQRR | 2.000 Seq. ID No. 107 |
| 2 | 98 | TPMEAELAR | 1.200 Seq. ID No. 108 |
| 3 | 99 | PMEAELARR | 0.400 Seq. ID No. 109 |
| 4 | 86 | RLLEFYLAM | 0.240 Seq. ID No. 63 |
| 5 | 38 | GATGGRGPR | 0.200 Seq. ID No. 110 |
| 6 | 44 | GPRGAGAAR | 0.200 Seq. ID No. 111 |
| 7 | 171 | LAQPPSGQR | 0.200 Seq. ID No. 112 |
| 8 | 154 | QQLSLLMWI | 0.160 Seq. ID No. 64 |
| 9 | 116 | LPVPGVLLK | 0.160 Seq. ID No. 65 |
| 10 | 120 | GVLLKEFTV | 0.120 Seq. ID No. 66 |
| 11 | 131 | NILTIRLTA | 0.080 Seq. ID No. 67 |
| 12 | 161 | WITQCFLPV | 0.080 Seq. ID No. 68 |
| 13 | 127 | TVSGNILTI | 0.080 Seq. ID No. 69 |
| 14 | 153 | LQQLSLLMW | 0.080 Seq. ID No. 70 |
| 15 | 159 | LMWITQCFL | 0.060 Seq. ID No. 71 |
| 16 | 158 | LLMWITQCF | 0.060 Seq. ID No. 72 |
| 17 | 132 | ILTIRLTAA | 0.040 Seq. ID No. 73 |
| 18 | 148 | SISSCLQQL | 0.040 Seq. ID No. 74 |
| 19 | 128 | VSGNILTIR | 0.040 Seq. ID No. 113 |
| 20 | 145 | LQLSISSCL | 0.040 Seq. ID No. 75 |
| 21 | 135 | IRLTAADHR | 0.040 Seq. ID No. 114 |
| 22 | 152 | CLQQLSLLM | 0.040 Seq. ID No. 76 |
| 23 | 110 | AQDAPPLPV | 0.040 Seq. ID No. 77 |
| 24 | 164 | QCFLPVFLA | 0.036 Seq. ID No. 78 |
| 25 | 143 | RQLQLSISS | 0.024 Seq. ID No. 79 |
| 26 | 108 | SLAQDAPPL | 0.020 Seq. ID No. 80 |
| 27 | 73 | NGCCRCGAR | 0.020 Seq. ID No. 81 |
| 28 | 134 | TIRLTAADH | 0.020 Seq. ID No. 82 |
| 29 | 54 | SGPGGGAPR | 0.020 Seq. ID No. 14 |
| 30 | 69 | ASGLNGCCR | 0.020 Seq. ID No. 83 |

Peptides were synthesized based on the peptide binding motif for HLA-A31 (hydrophobic residues at position 2 and positively charged residues at position 9) (Rammensee et al. 1995, *Immunogenetics* 41:178–228) and tested for reactivity with CTL clone 5.

These peptides were pulsed onto HLA-A31-positive 1510EBV B cells and tested for their ability to stimulate cytokine release by CTL clone 5. As shown in Table 6, the 10-mer peptide ESO10-53 (ASGPGGGAPR) (SEQ ID NO: 25), starting at position 53 of the NY-ESO-1 protein was strongly recognized by CTL clone 5, while the overlapping 9-mer peptides, ES09-54 as well as ESO10$^{-127}$, were weakly recognized when pulsed onto 1510EVB B cells. CTL clone 10 recognized the same peptide as CTL clone 5 (data not shown). Interestingly, CTL clone 2 did not recognize any of these peptides (Table 6), even though it recognized 586mel and COS-7 transfected with NY-ESO-1 (see below). The reactivity of CTL clone 5 was undetectable when either the ESO9-54 or the ESO10-127 peptides were used at concentrations below 100 nM to sensitize EBV cells.

TABLE 6

Screening of synthetic peptides with reactivity to CTL Clone 5[a]

| Target cells pulsed with peptide from NY-ESO-1 | | CTL clone 5 GM-CSF release (pg/ml) |
|---|---|---|
| Peptides from CAG-3 | | |
| 1510EBV + ESO9-90 | AQPPSGQRR | <50 (SEQ. ID NO: 6) |
| 1510EBV + ESO9-98 | TPMEAELAR | <50 (SEQ. ID NO: 7) |
| 1510EBV + ESO9-99 | PMEAELARR | <50 (SEQ. ID NO: 8) |
| 1510EBV + ESO9-38 | GATGGRGPR | <50 (SEQ. ID NO: 9) |
| 1510EBV + ESO9-45 | GPRGAGAAR | <50 (SEQ. ID NO: 10) |
| 1510EBV + ESO9-89 | LAQPPSGQR | <50 (SEQ. ID NO: 11) |
| 1510EBV + ESO9-128 | VSGNILTIR | <50 (SEQ. ID NO: 12) |
| 1510EBV + ESO9-35 | IRLTAADHR | <50 (SEQ. ID NO: 13) |
| 1510EBV – ESO9-54 | SGPGGGAPR | 304 (SEQ. ID NO: 14) |
| 1510EBV + ESO10-127 | TVSGNILTIR | 293 (SEQ. ID NO: 15) |
| 1510EBV + ESO10-34 | TIRLTAADHR | <50 (SEQ. ID NO: 16) |
| 1510EBV + ESO10-97 | ATPMEAELAR | <50 (SEQ. ID NO: 17) |
| 1510EBV + ESO10-170 | FLAQPPSGQR | <50 (SEQ. ID NO: 18) |
| 1510EBV + ESO10-98 | TPMEAELARR | <50 (SEQ. ID NO: 19) |
| 1510EBV + ESO10-77 | RCGARGPESR | <50 (SEQ. ID NO: 20) |
| 1510EBV + ESO10-68 | AASGLNGCCR | <50 (SEQ. ID NO: 21) |
| 1510EBV + ESO10-171 | LAQPPSGQRR | <50 (SEQ. ID NO: 22) |
| 1510EBV + ESO10-44 | RGPRGAGAAR | <50 (SEQ. ID NO: 23) |
| 1510EBV + ESO10-72 | LNGCCRCGAR | <50 (SEQ. ID NO: 24) |
| 1510EBV + ESO10-53 | ASGPGGGAPR | >2000 (SEQ. ID NO: 25) |
| 1510EBV + None | | <50 |

[a]1510EBV cells were incubated with individual peptide at a concentration of 0.1 μg/ml for 90 min. GM-CSF release was measured after co-incubation of peptide-loaded 1510EBV cells with CTL clone 5. GM-CSF release was measured after coincubation of peptide-loaded 1510EBV cells with CTL clone 5. 1510EBV was a EBV transformed B cell line expressing HLA-A31.

EXAMPLE 11

Recognition of Modified Peptides

To examine whether CTL clone 5 also recognized peptides that contained the core amino acid sequence with the extension of amino acid residues at either the N or C terminus, we made overlapping 11-mer, 12-mer, 13-mer, 14-mer, and 15-mer peptides, as well as several peptides containing substitutions at either position. 1, 2 or 10 of ESO10-53 (Table 7 and FIG. 3A). CTL clone 5 was capable of recognizing 11-mer, 12-mer, 13-mer, 14-mer, and 15-mer peptides with amino acid extensions at the N terminus of the ESO-53 core peptide, although the longer peptides appeared to stimulate significantly less GM-CSF secretion than did the ESO10-53 10-mer peptide (Table 7). However, an extension of only a single amino acid residue at the C terminus of ESO10-53 abrogated its ability to stimulate T cells (Table 7). CTL clone 5 did not recognize the 8-mer peptide.

Figure 5A:
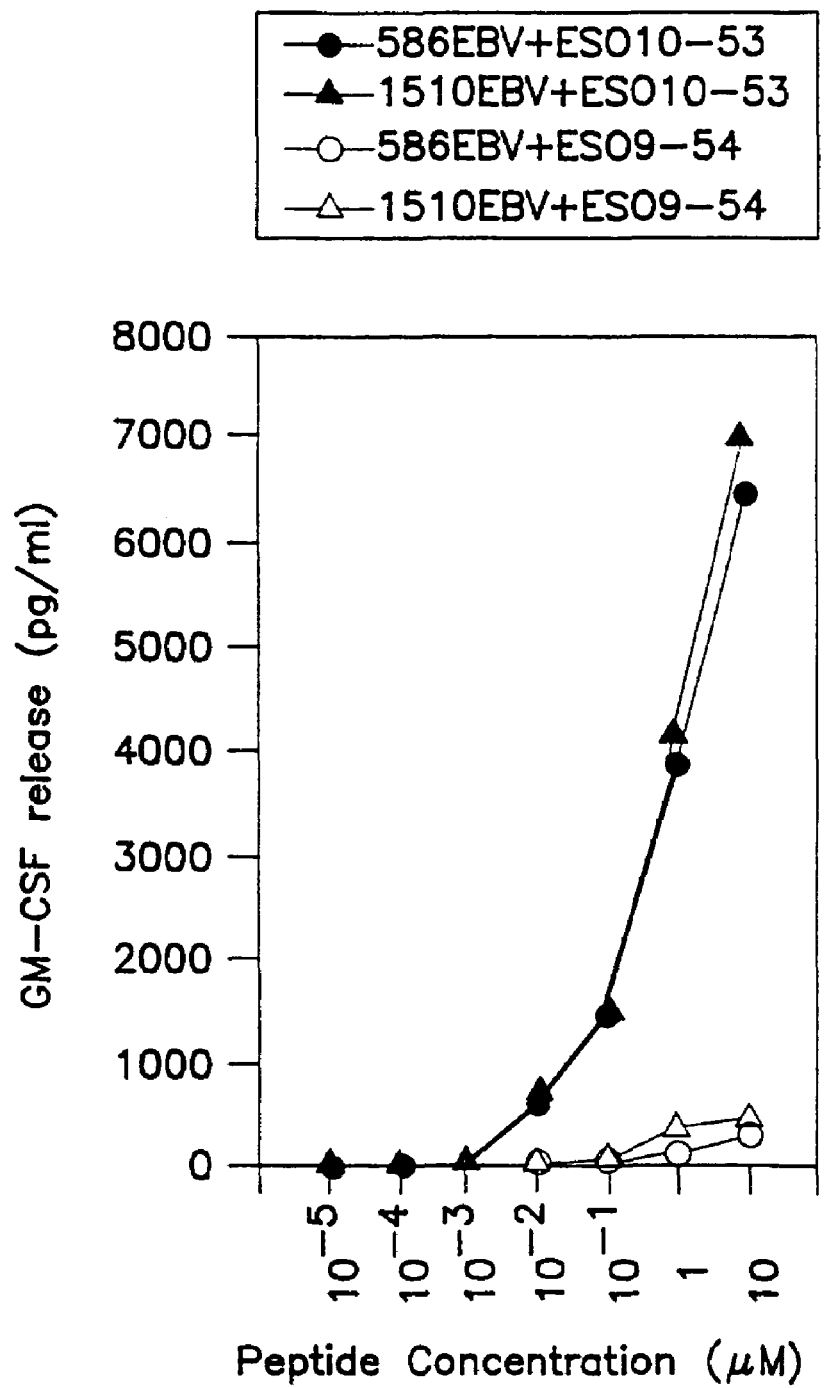
FIGS. 5A–5C. Characterization of the 9-mer ESO9-54 and 10-mer ESO10-53 derived from the normal open reading frame.
Figure 5B:
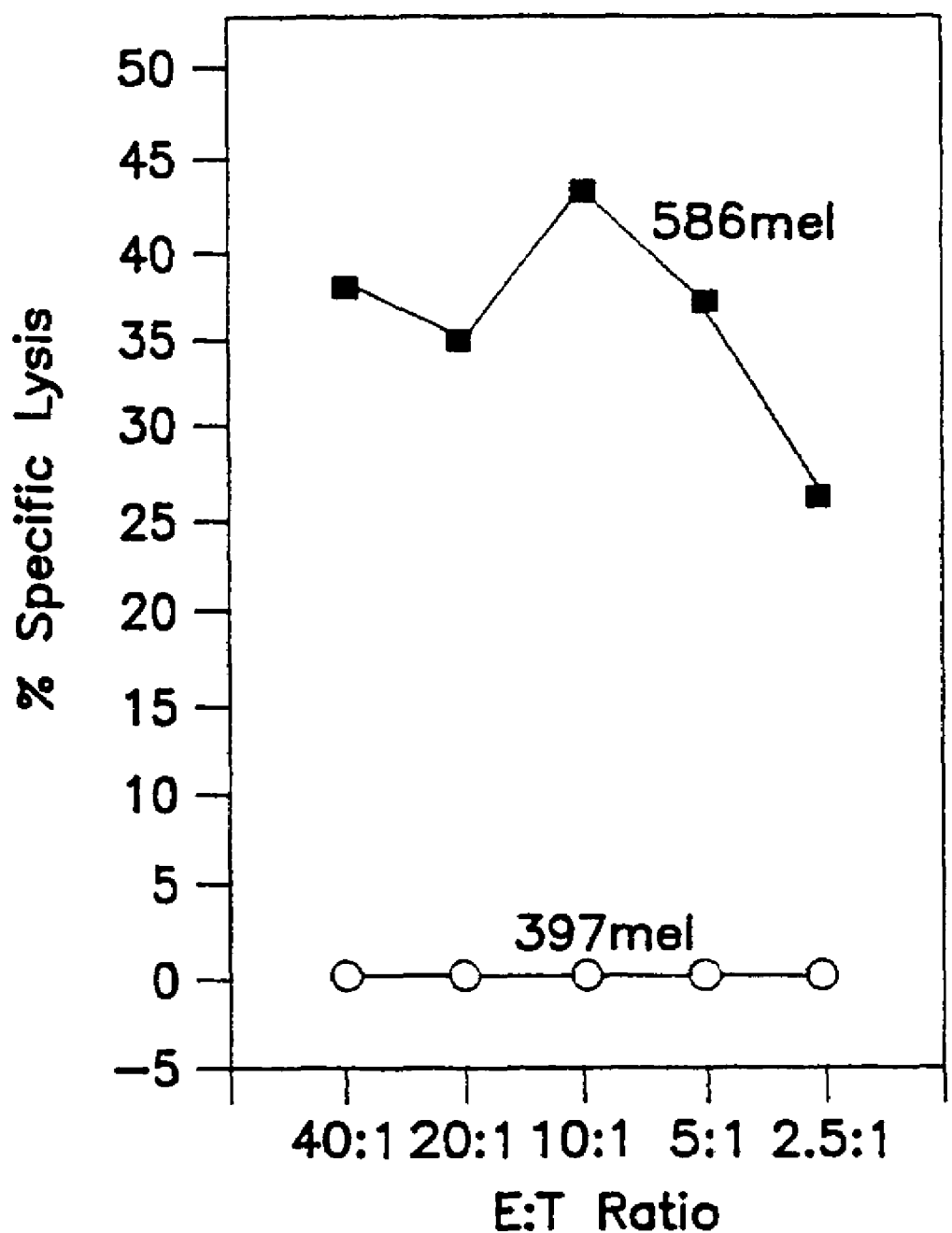

Titration experiments demonstrated that CTL reactivity was detectable at 10 nM concentration of ESO10-53 peptide. GM-CSF release from CTL clone 5 increased with the increasing peptide concentrations, and no plateau was reached at 10 μM peptide concentration (FIG. 5A). In addition to measuring cytokine release stimulated by ESO10-53, the ability of this peptide to sensitize target cells for lysis by CTL clone 5 was examined. CTL clone 5 was capable of lysing HLA-A31-positive tumor 586 mel, but not the HLA-A31-negative and NY-ESO-1-positive tumor 397mel (FIG. 5B).

Figure 5C:
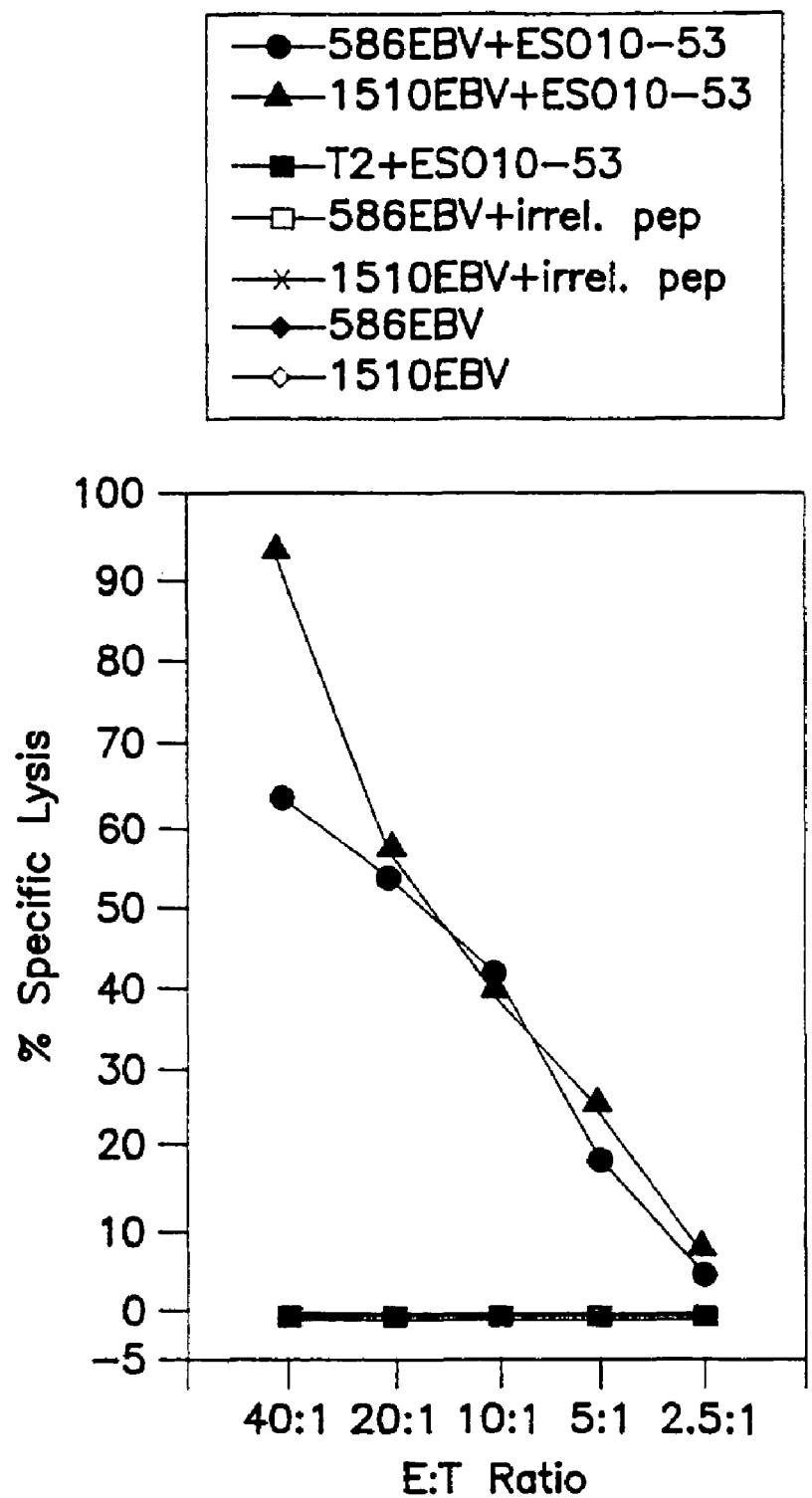
Figure 6A:
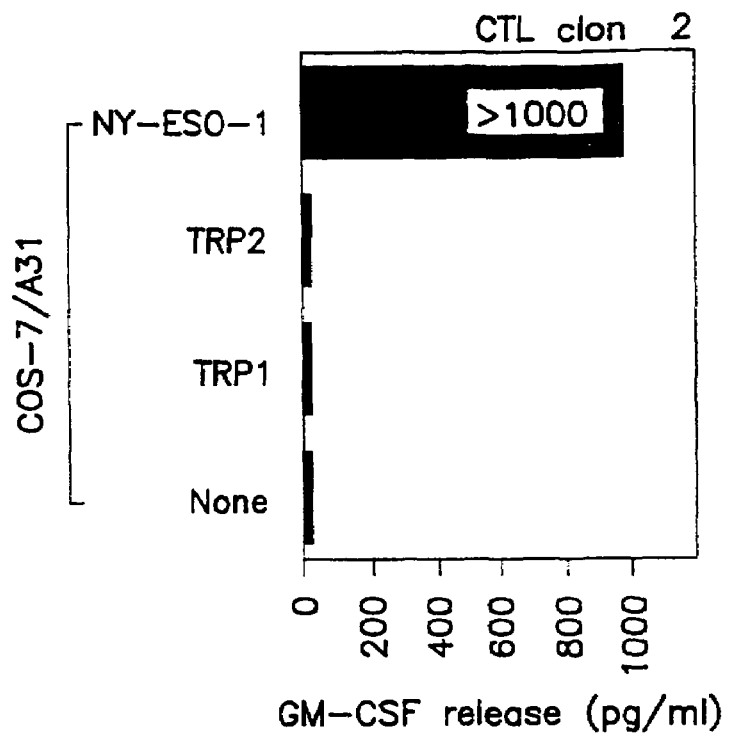
FIGS. 6A–6H. CTL clones 2 and 14 recognize the NY-ESO-1 gene, but not the ESO10-53 peptide derived from the NY-ESO-1 protein. CTL clones 2, 14 and 5 recognized NY-ESO-1 when cotransfected with HLA-A31 cDNA into COS-7 (FIG. 6A, C, E and G). TIL1244, which recognized TRP-2 But not NY-ESO-1, was used as a specificity control.
Figure 6B:
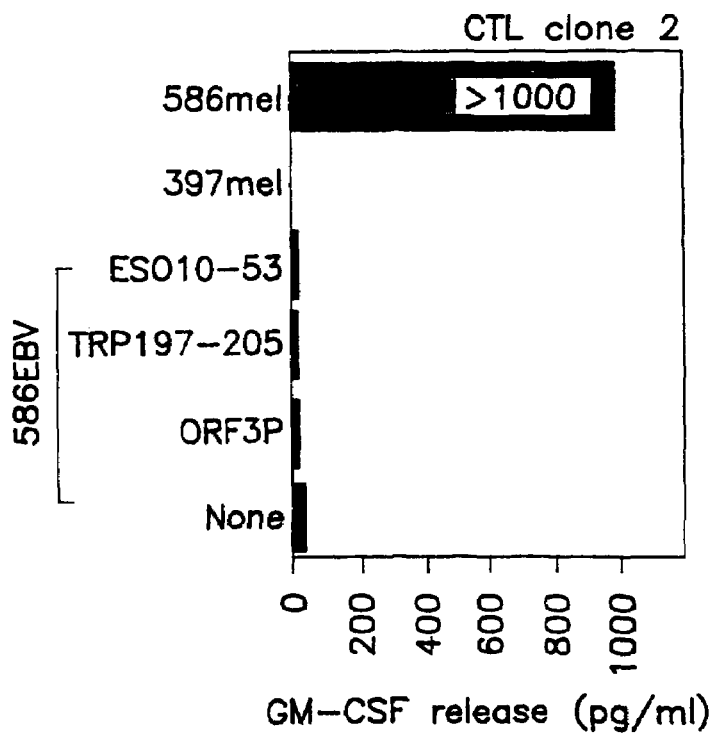
Figure 6C:
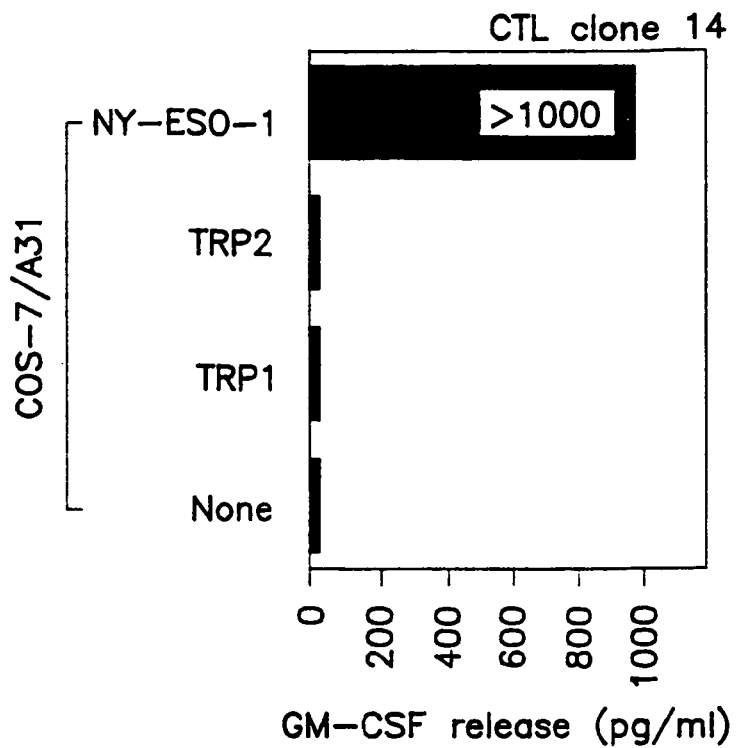
Figure 6D:
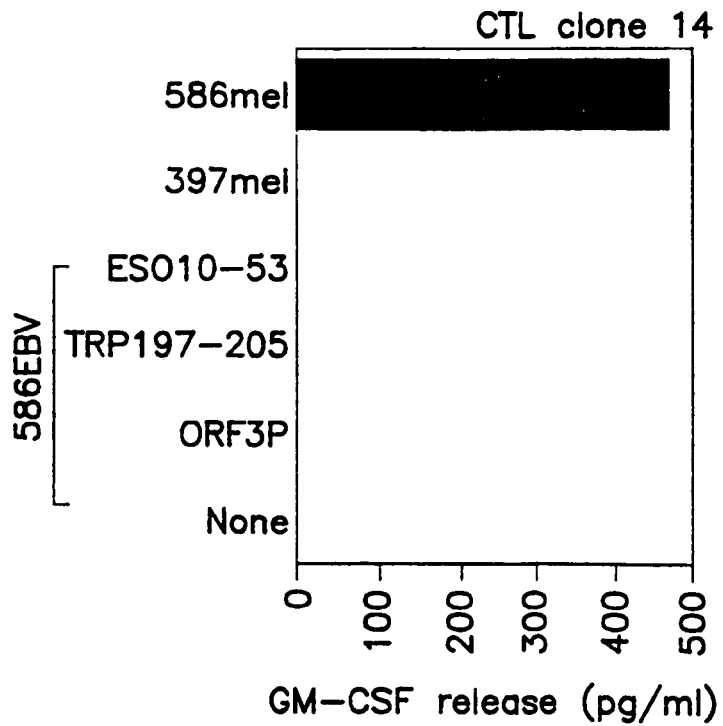
Figure 6E:
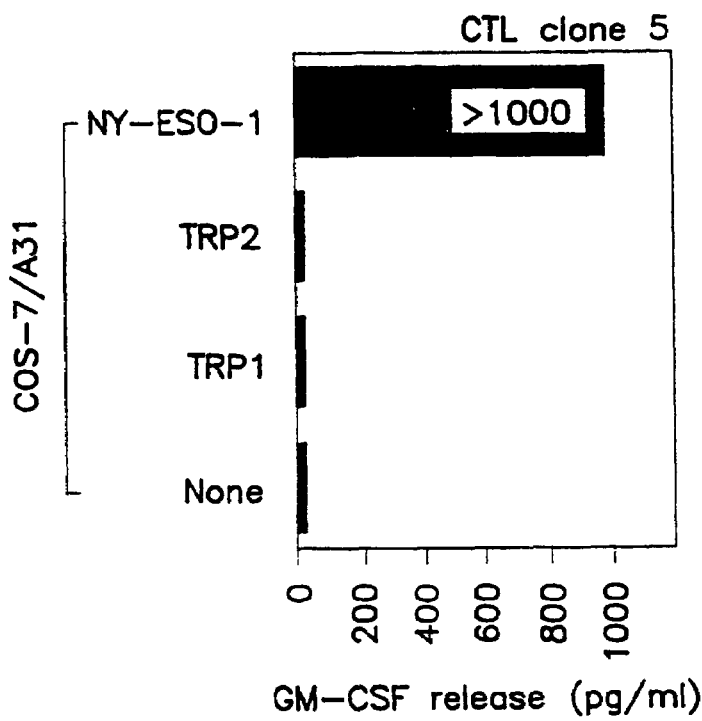
Figure 6F:
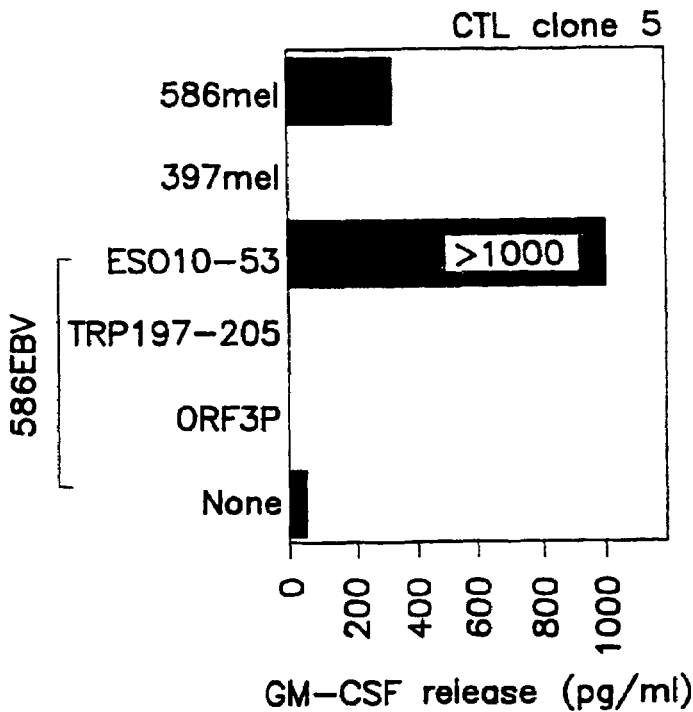
Figure 6G:
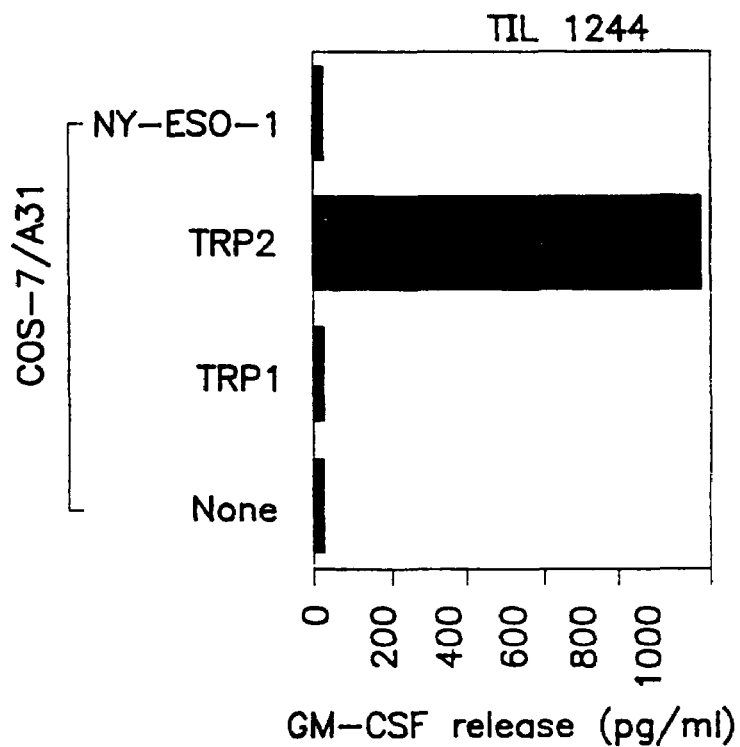
Figure 6H:
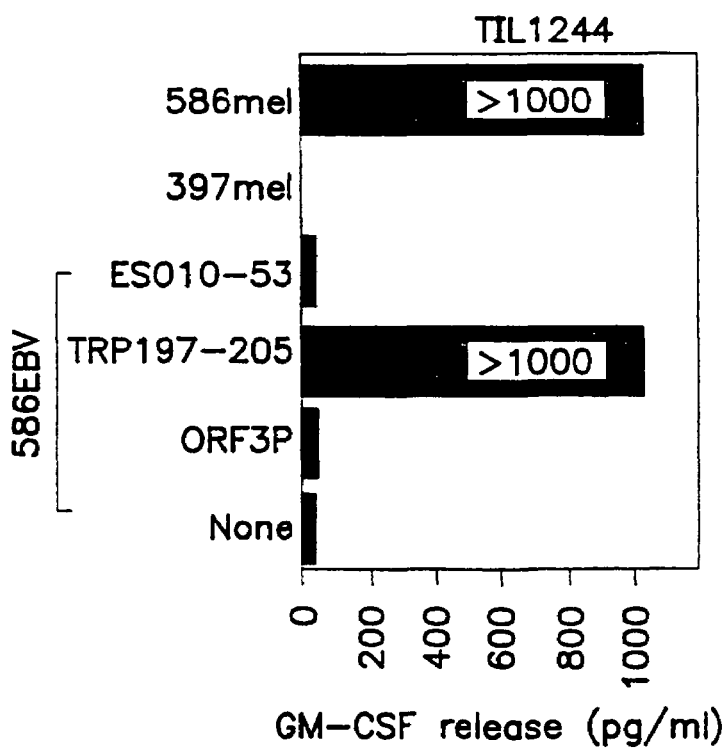

CTL clone 5 lysed >60% of either 586EBV or 1510EBV that had been incubated with the ESO10$^{-53}$ peptide at an E:T ratio of 40:1, and ~5–10% lysis of target cells was observed at an E:T ratio of 2.5:1 E:T. CTL clone did not lyse either 586EBV or 1515EBV B cells alone or pulsed with an irrelevant peptide, nor did it lyse the HLA-A3'-negative T2 cells pulsed with the ESO10-53 peptide (FIG. 5C).

Next, it was tested whether T cell recognition of the 10-mer peptide could be improved by substituting amino acids at anchor residues. A number of synthetic peptides with modification at residues 1, 2 and 10 were made and tested for recognition by CTL clone 5 when pulsed onto 586EBV B cells (Table 7). The modified 10-mer peptides with a substitution at position 2 derived from the wild-type ASGPGGGAPR (SEQ ID NO: 25) were still recognized by CTL clone 5 when pulsed on 586EBV B cells. The reactivity of peptides containing a substitution of either Ala, Ile, Leu or Val at position 2 was lower than that of the wild-type peptide, while one peptide containing a substitution of Thr for Ser at position 2 resulted in a slightly higher reactivity than the wild-type ESO10-53 peptide. In contrast, peptides containing substitutions of Arg with Lys or His completely lost their ability to stimulate T cells, suggesting that the Arg at the C-terminus of the ESO10-53 peptide represents a critical anchor residue. Peptides with a substitution at position 1 were recognized poorly or not recognized at all by CTL clone 5 (Table 7). These results indicate that the ESO-53 peptide, ASGPGGGAPR (SEQ ID NO: 25), represents the best peptide for T cell recognition.

EXAMPLE 12

Antigenic Peptides Derived from an Alternative Open Reading Frame

Figure 7A:
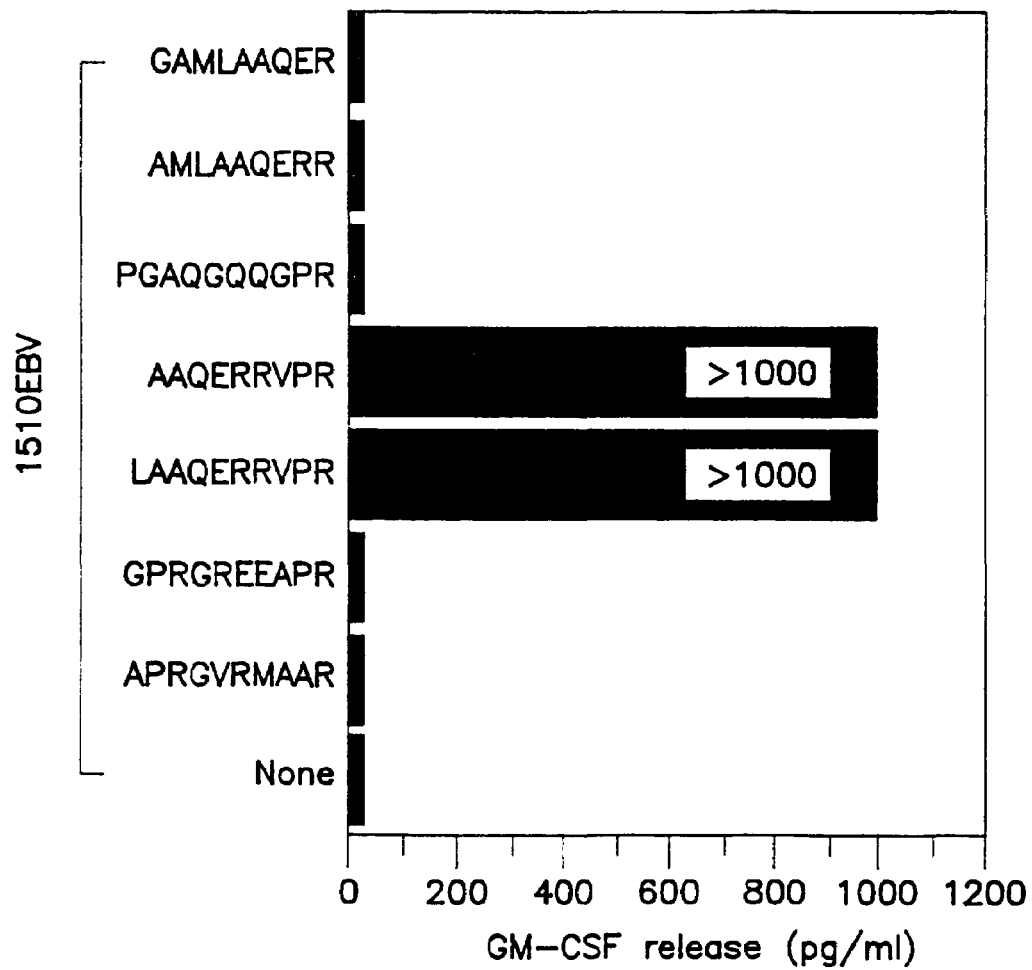
FIGS. 7A–7C. An alternative open reading frame of the NY-ESO-1 gene and antigenic peptides recognized by CTL.
Figure 7B:
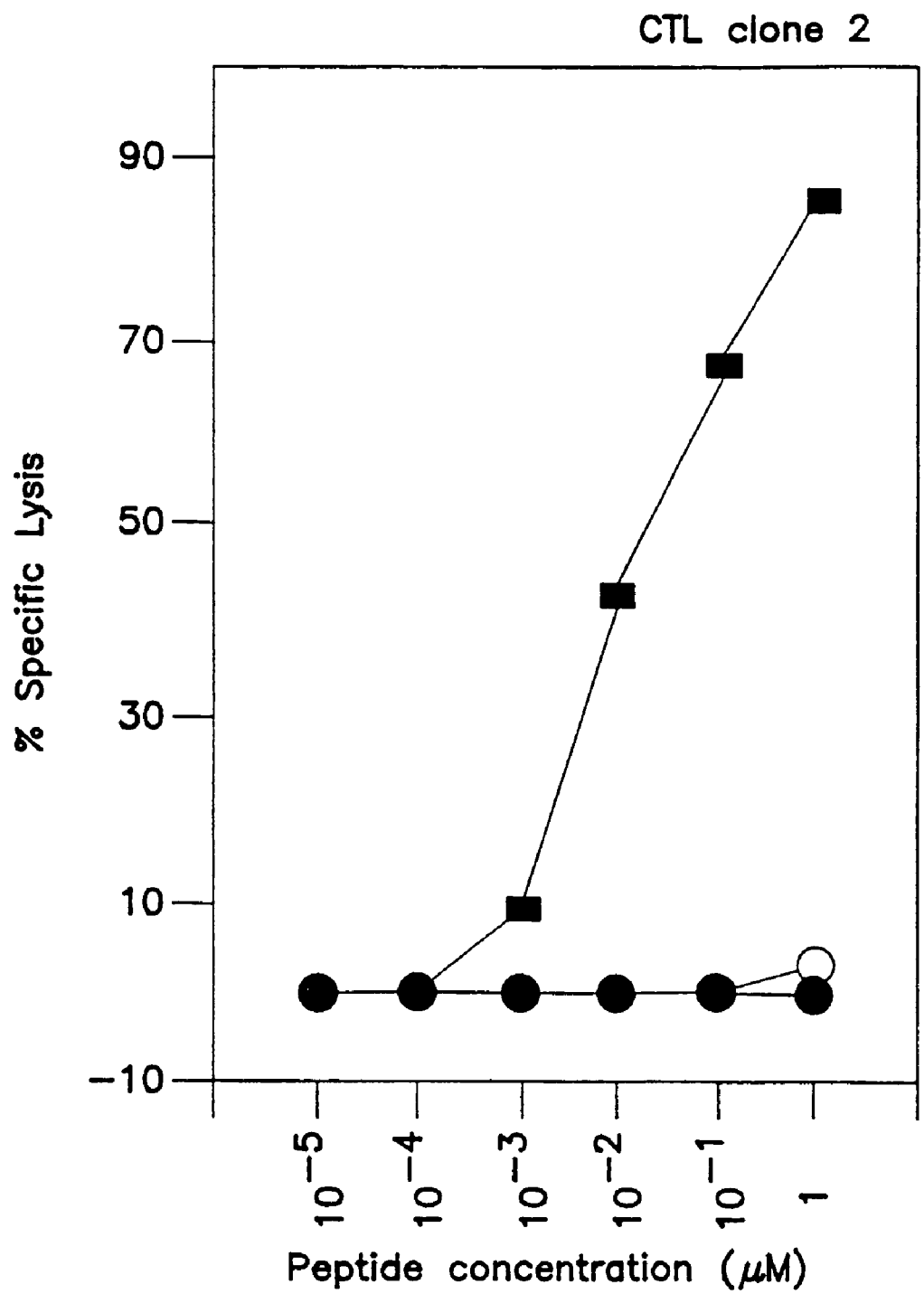

Two additional CTL clones, clones 2 and 14, appeared to recognize 586mel as well as COS-7 cells transfected with NY-ESO-1 and HLA-A31 cDNA, but failed to recognize the ESO 10-53 peptide (FIGS. 6A–6H). CTL clone 5 and TIL1244 were used for the specificity controls. Additional experiments showed that CTL clone 2 did not respond to any of 19 other peptides containing the HLA-A31 Binding motif derived from the normal open reading frame of NY-ESO-1 (Table 6). To test the hypothesis that CTL may recognize a peptide from a gene product translated from an alternative open reading frame of the same gene, synthetic peptides were made with HLA-A31 Binding motif on the basis of amino acid sequence predicted from the second open reading frames (ORF2) (FIG. 3A). Strikingly, CTL clone 2 recognized ESORF2-9-19 (AAQERRVPR) (SEQ ID NO: 46) as well as the overlapping ESORF2-10-18 (LAAQER-RVPR) (SEQ ID NO: 47) peptides when pulsed onto 1510EBV B cells. Representative data for CTL clone 2 is shown in FIG. 7A. CTL clone 14 recognized the same peptides as CTL clone 2 (Data not shown). These results suggest that CTL clones 2 and 14 recognized an antigenic peptide derived from the ORF2 (FIG. 3A). A protein database search revealed that the 58 amino acid protein of ORF2 has a 52% similarity to the chain A of glutamate dehydrogenase in a 25 amino acid region (34). Peptide titration experiments demonstrated that CTL clone 2 was capable of lysing 1510EBV pulsed with ESORF2-10-18 (LAAQER-RVPR) (SEQ ID NO: 47) at relatively low concentrations of peptide, but failed to lyse 1510EBV pulsed with ESO10-53 or HLA-A31-negative 1102EBV pulsed with ESORF2-10-18 (FIG. 7B). In addition, CTL clone 2 also recognized overlapping 11mer, 12-mer, and 13-mer peptides with amino acid extensions at the N terminus of the ESORF2-10-18 peptide at relatively high concentrations (data not shown).

Figure 7C:
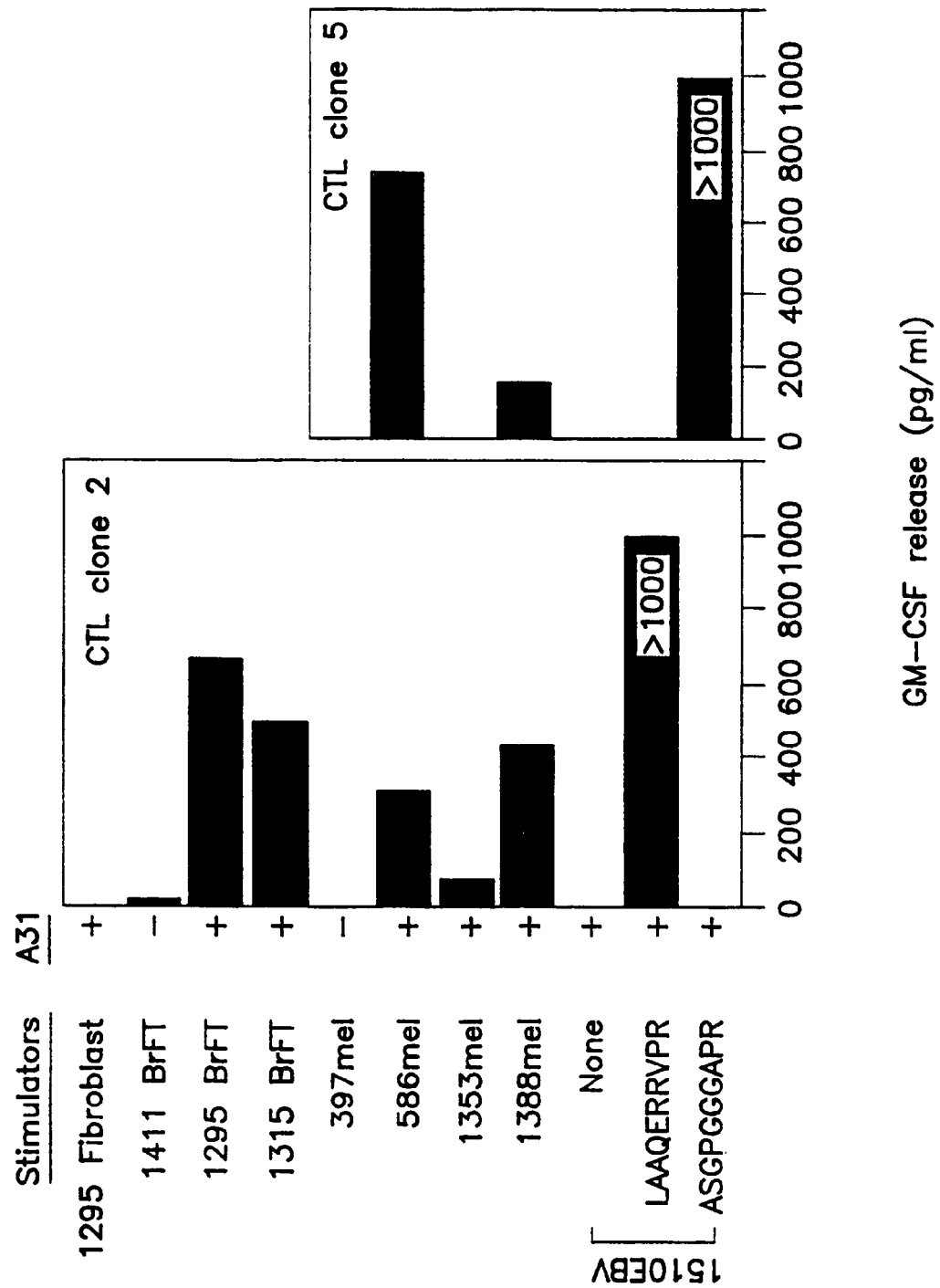

Additional experiments were carried out to determine whether CTL clones recognize the ORF2 gene product of the NY-ESO-1 in other tumor types. As shown in FIG. 7C, the recognition pattern of CTL clone 2 was similar to that of CTL clone 5 on tumor cells. CTL clone 2 recognized HLA-A31 positive fresh 1315Br and 1295Br breast tumors as well as 586mel and 1388mel, but did not recognize HLA-A31 negative fresh 1411Br breast tumor, 397mel, nor the HLA-A31 negative 1295 fibroblast. Although 1353mel expresses HLA-A31, neither CTL clone 2 nor clone 5 responded to 1353mel because 1353mel is NY-ESO-1 negative tumor. As previously demonstrated, CTL clone 5 recognized the ESO10-53 ASGPGGGAPR peptide (SEQ ID NO: 25) and CTL clone 2 recognized the ORF2-10-18 LAAQERRVPR peptide (SEQ ID NO: 47) derived from the ORF2 following incubation with 1510EBV B cells (FIG. 7C). These results strongly suggest that the ORF2 gene product was translated, processed and presented in melanoma as well as breast tumors. Therefore, NY-ESO-1 Encodes two different proteins: a protein with 180 amino acids (ORF1) recognized by CTL clones 5 and 10, and a protein with 58 amino acids (ORF2) recognized by CTL clones 2 and 14.

TABLE 7

Recognition of the modified peptides by CTL clone 5[a]

| Target cells pulsed with peptides | GM-CSF release by CTL clone 5 | |
|---|---|---|
| | EXPT. 1 (1510EBV) | EXPT. 2 (586EBV) |
| 1510EBV + AGAARASGPGGGAPR | 728 | 532 (SEQ. ID NO: 26) |
| 1510EBV + GAARASGPGGGAPR | 659 | 678 (SEQ. ID NO: 27) |
| 1510EBV + AARASGPGGGAPR | 844 | 738 (SEQ. ID NO: 28) |
| 1510EBV + ARASGPGGGAPR | 840 | 738 (SEQ. ID NO: 29) |
| 1510EBV + RASGPGGGAPR | 851 | 708 (SEQ. ID NO: 30) |
| 1510EBV + SGPGGGAPR | <50 | <50 (SEQ. ID NO: 14) |
| 1510EBV + GPGGGAPR | <50 | <50 (SEQ. ID NO: 31) |
| 1510EBV + ASGPGGGAPRG | <50 | <50 (SEQ. ID NO: 32) |
| 1510EBV + SGPGGGAPRG | <50 | <50 (SEQ. ID NO: 33) |
| 1510EBV + ASGPGGGAPR | 1097 | 1044 (SEQ. ID NO: 25) |
| 1510EBV + AAGPGGGAPR | 688 | 676 (SEQ. ID NO: 34) |
| 1510EBV + AIGPGGGAPR | 428 | 550 (SEQ. ID NO: 35) |
| 1510EBV + ALGPGGGAPR | 200 | 378 (SEQ. ID NO: 36) |
| 1510EBV + AVGPGGGAPR | 556 | 512 (SEQ. ID NO: 37) |
| 1510EBV + ATGPGGGAPR | 1630 | 1158 (SEQ. ID NO: 38) |
| 1510EBV + ASGPGGGAPK | <50 | <50 (SEQ. ID NO: 39) |
| 1510EBV + ASGPGGGAPH | <50 | <50 (SEQ. ID NO: 40) |
| 1510EBV + TSGPGGGAPR | 320 | 346 (SEQ. ID NO: 41) |
| 1510EBV + VSGPGGGAPR | 825 | 666 (SEQ. ID NO: 42) |
| 1510EBV + LSGPGGGAPR | <50 | <50 (SEQ. ID NO: 43) |

TABLE 7-continued

Recognition of the modified peptides by CTL clone 5[a]

|  |  | GM-CSF release by CTL clone 5 | |
| --- | --- | --- | --- |
| Target cells pulsed with peptides |  | EXPT. 1 (1510EBV) | EXPT. 2 (586EBV) |
| 1510EBV + | RSGPGGGAPR | <50 | <50 (SEQ. ID NO: 44) |
| 1510EBV + | None | <50 | <50 |

[a]586EBV or 1510EBV cells were incubated with individual peptide at a concentration of 0.1 μg/ml for 90 min. GM-CSF release was measured after coincubation of peptide-loaded EBV cells with 5 × 10$^4$ CTL clone 5. The wild-type 10 mer ESO10-53 peptide was underlined. Peptides with amino acid substitutions are marked by bold face and underscored. 586EBV and 1510EBV were HLA-A31-positive EBV transformed B cell lines.

EXAMPLE 13

In Vivo Treatment Assay

For in vivo treatment, MHL-A31$^+$ transgenic mice are challenged with either 1×10$^5$ or 5×10$^5$ CAG-3 B16 mouse melanoma cells intravenously in order to establish pulmonary metastases. Mice are subsequently vaccinated with a recombinant virus expressing cancer peptide, SEQ. ID NO. 4 or 5 at 10$^5$ PFU/mg body weight. Mice are euthanized on day 12 and the number of pulmonary metastases in vaccinated mice vs. non-vaccinated mice determined.

EXAMPLE 14

Cancer Antigen Specific T Lymphocytes Immunotherapy

T-lymphocytes presensitized to a melanoma antigen may be effective in therapeutically treating mammals afflicted with a melanoma. T-lymphocytes are isolated from peripheral blood or melanoma tumor suspensions and cultured in vitro (Kawakami et al 1988, *J. Exp. Med.* 168:2183–2191).

The T lymphocytes are exposed to the cancer peptide, SEQ. ID NO. 4 or 5 at a concentration of 1 μg/ml alone or in the presence of IL-2, resensitized and expanded in culture. T-lymphocytes exposed to the cancer peptide are administered to a mammal at about 10$^9$ to 10$^{12}$ lymphocytes per mammal. The lymphocytes are administered either intravenously, intraperitoneally or intralesionally. The treatment may be administered concurrently with other therapeutic treatments such as cytokines, surgical excision of melanoma lesions and chemotherapeutic drugs.

DISCUSSION

NY-ESO-1 is a Cellular Immune Target

Five differentiation antigens including tyrosinase, MART-1, gp100, TRP-1/gp75 and TRP-2 have been identified as melanoma Ags recognized by T cells derived from TILs (13–19), which have been shown to be associated with antitumor reactivity in vivo. Thus far, no TILs available in the Surgery Branch at National Cancer Institute recognize MAGE-1, BAGE and GAGE, which are expressed only in testis and cancer cells. Here we show that NY-ESO-1, another cancer-shared Ag, is a tumor Ag recognized by HLA-A31-restricted T cells. NY-ESO-1 was independently isolated using the autologous serum from a patient with esophageal cancer (29), suggesting that the NY-ESO-1 gene product was an immune target for Ab-mediated immunity. Results in this study provide evidence that NY-ESO-1 is also an immune target recognized by T cells. This is further supported by a recent report that HLA-A2 restricted CTL recognize NY-ESO-1 Established in a melanoma patient (35). Several tumor antigens, including MAGE-1, tyrosinase, TRP-1, recognized by CTL, have been found to be reactive with antibody as well (36, 37). Since NY-ESO-1 is not expressed in normal human tissues except the testis, which does not express MHC class I molecules and is considered as an immunologically privileged site, this gene product may consistitute a safe immune target for the immunotherapy of patients with cancer.

NY-ESO-1 is a Breast Cancer Ag

Based on its gene expression pattern, NY-ESO-1 Belongs to a member of an expanding family of antigens (Ags) including MAGE-1, MAGE-3, BAGE, GAGE and HOM-MEL-40 (9–12, 30). However, NY-ESO-1 is highly expressed in a significant proportion of breast, prostate and bladder cancers (29) compared to MAGE, BAGE and GAGE. More importantly, CTL clones recognized two HLA-A31-positive fresh and cultured breast cancer cells (Table 2 and FIG. 7C). To our knowledge, this is the first demonstration of CTL recognition of NY-ESO-1 positive breast cancer cells. Although the expression of MAGE-1, MAGE-3 and others were reported to be detected by RT-PCR in breast tumors at a low frequency (<5–10%), CTL recognition of these breast tumors by the Ag-specific CTL has not been documented. It has been difficult to generate breast-reactive CTLs from PBL in vitro although MHC-restricted T cells that recognized HER-2/neu peptides on breast cancer cells have been reported (26–28). Identification of NY-ESO-1 peptides presented on the cell surface of breast cancers is important for the development of Ag-specific cancer vaccines for the treatment of patients with breast cancer. The CTL cloning approach described here represents a strategy for the isolation breast cancer Ags.

Translation of Different ORFs as a Mechanism for Generating T Cell Epitopes

To define antigenic peptides, we found the 10-mer ASG-PGGGAPR (SEQ ID NO.: 25) derived from the NY-ESO-1 protein as the best antigenic peptide recognized by CTL clone 5 although the 9-mer, 11-mer, 12-mer, 13-mer, 14-mer and 15-mer peptides were also recognized. This reactivity may be due to the presence of two proline residues in these peptides. Proline residues in the core peptide sequence may allow the peptides to bulge out of the MHC binding pocket, thus the anchored residues in the longer peptides can still fit into the HLA-A31 molecule. An alternative explanation is that the longer peptides may be processed to the shorter peptides by extracellular or serum proteases (38). However, when the longer peptides were pulsed onto 586EBV B cells in serum-free conditions, they were still recognized by CTL clone 5 (data not shown). This experiment, however, does not exclude the possibility that these longer peptides were processed by extracellular proteases. The modified peptide, ATGPGGGAPR (SEQ ID NO.: 38) with a substitution of Thr for Ser appeared to slightly improve binding affinity to the MHC class I molecule, thus enhancing the immunogenicity of peptides (39). It is not clear why CTL clone 5 recognized the unrelated ESO10-127 peptide, but its recognition was weak and only could be detected at a relatively high peptide concentration.

Interestingly, two additional CTL clones recognized COS-7 transfected with NY-ESO-1 plus HLA-A31 cDNA, but not the ESO10-53 peptide which was derived from the ORF1 of the NY-ESO-1 gene (FIGS. 6A–6D). Further analysis showed that CTL clone 2 recognized a peptide from the gene product translated from an alternative open reading frame (ORF2) of NY-ESO-1. Although there are several examples that two different proteins are translated from different ORFs from a single viral mRNA (40), very few cases have been reported in single eukaryotic mRNA. Two examples have been reported: TRP-1/gp75 which encodes two different proteins, gp75 recognized by sera from a patient with melanoma and a 24 amino acid gene product recognized by CTLs (24, 37); and 43 kDa-Ag recognized by squamous cell carcinoma reactive CTL (41). Interestingly, the cyclin-dependent kinase inhibitor p16 gene also encodes two gene products, p16 and $p19^{ARF}$. However, the alternative ORF gene product $p19^{ARF}$ is translated from an alternatively spliced transcript shares an identical sequence with the p16 transcript except the first exon (42). Recent studies showed that the alternative reading frame product $p19^{ARF}$ plays a role in cell cycle regulation and tumor suppression (43). The NY-ESO-1 gene reported here encodes two different proteins: a 180 amino acid protein encoded by ORF1 and a 58 amino acid protein encoded by ORF2. The ORF2 product is located inside ORF1. Strikingly, CTL clones 5 and 10 recognized antigenic peptides derived from ORF1, while CTL clone 2 and 14 recognized an antigenic peptide from ORF2. Both CTL clones 2 and 5 recognized several HLA-A31+ melanomas as well as fresh breast tumors (Table 2 and FIG. 7C), suggesting that the translation of the alternative ORF2 may serve as a general mechanism in vivo for generating T cell epitopes.

The mechanism by which the alternative ORF is translated is currently not known. However, there are several potential explanations for the production of alternative reading frames. The leaky-scanning model is one possible explanation: ribosomes occasionally bypass the first AUG with a poor KOZAK consensus sequence and initiates translation at a downstream AUG (43, 44). In the case of NY-ESO-1, the start codon for translation of ORF1 is not in the optimal context. There are four potential start codons that could be used to translate the ORF2. In our previous report, a CTL epitope was translated from an alternative reading frame of gp75/TRP-1 (24). Recognition of the epitope of ORF3 By CTL was affected by the presence of the first ATG codon used for the translation of the gp75 protein and was completely abolished when the internal ATG preceeding the T cell eptiope (ORF3P) was changed to ATC, suggesting that ribosomal scanning may be a possible mechanism. In the studies of the influenza nucleoprotein, CTL epitopes were produced via a ribosomal scanning mechanism (44). However, in a similar study, ribosomal frameshifting was suggested as a mechanism for the production of T cell epitopes (45). Other mechanisms have also been proposed for the production of T cell epitopes derived from different genes. For example, several T cell epitopes were identified from gene products translated from a cryptic initiation codon of the 5' untranslated region (46,47), from a non-ATG-defined open reading frame (48), and from introns of transcript (22, 49, 50). Since both the alternative open reading frame of gp75/TRP-1 and NY-ESO-1 are located within the primary open reading frame, it is of particular interest to understand the underlying mechanism.

Although there are only a few examples of the usage of the alternative open reading frames in eukaryotes reported in the literature, we believe that more examples will be reported in the future when tumor-reactive CTL and autoantibodies are available and used to identify target proteins or peptides. Therefore, it is important to understand the biologic significance of the gene products translated from alternative open reading frames. One possibility is that these gene products serve as antigenic targets of the Ag processing machinery to increase the efficiency and capacity of the immune surveillance. Identification of T cell epitopes derived from different open reading frames of NY-ESO-1 suggests that the identity of immunogenic peptides for cancer vaccines may not be limited only to peptides derived from the primary open reading frame. It is not clear at the present time whether the ORF2 gene product of NY-ESO-1 and the ORF3 gene product of gp75/TRP-1 have biologic functions in addition to immune responses of T cells.

REFERENCES

1. Rosenberg, S. A., B. S. Packard, P. M. Aebersold, D. Solomon, S. L. Topalian, S. T. Toy, P. Simon, M. T. Lotze, J. C. Yang, C. A. Seipp, et al, 1998. Use of tumor infiltrating lymphocytes and interleukin-2 in the immunotherapy of patients with metastatic melanoma. Preliminary report. *N. Engl. J. Med.* 319:1676.
2. Rosenberg, S. A., J. Y. Yannelli and J. C. Yang, 1994. Treatment of Patients with metastatic melanoma using autologous tumor-infiltrating lymphocytes and interleukin-2. *J. Natl. Cancer Inst.* 86:1159.
3. Boon, T., J. C. Cerottini, B. Van den Eynde, P. van der Bruggen and A. Van Pel. 1994. Tumor antigens recognized by T lymphocytes. *Annu. Rev. Immunol.* 12:337.
4. Houghton, A. N. 1994. Commentary: cancer antigens: immune recognition of self and altered self. *J. Exp. Med.* 180:1.
5. Tsomides, T. J. and H. N. Eisen, 1994. Commentary: T-cell antigens in cancer. *Proc. Natl. Acad. Sci. USA* 91:3487.
6. Pardoll, D. M. 1994. News and views: a new look for the 1990s. *Nature* 369:357.
7. Wang, R. F., and S. A. Rosenberg, 1996. Human tumor antigens recognized by T lymphocytes: implications for cancer therapy. *J. Leukocyte Biol.* 60:296.
8. Rosenberg, S. A. 1997. Cancer vaccines based on the identification of genes encoding cancer regression antigens. *Immunol. Today* 18:175.
9. van der Bruggen, P., C. Traversari, Pl. Chomez, C. Lurquin, E. Deplaen, B. Van den Eynde, A. Knuth and T. Boon, 1991. A gene encoding an antigen recognized by cytolytic T lymphocytes on a human melanoma. *Science* 254:1643.

10. Gaugler, B., B. Van den Eynde, P. van der Bruggen, P. Romero, J. J. Gaforio, E. De Plaen, B. Lethe, F. Brasseur and T. Boon, 1994. Human gene MAGE-3 codes for an antigen recognized o a melanoma by autologous cytolytic T lymphocytes. *J. Exp. Med.* 179:921.

11. Van Den Eynde, B., O. Peeters, O. De Backer, B. Gaugler, S. Lucas and T. Boon, 1995. A new family of genes coding for an antigen recognized by autologous cytolytic T lymphocytes on a human melanoma. *J. Exp. Med.* 182:689.

12. Boël P., C. Wildmann, M. L. Sensi, R. Brasseur, J. C. Renauld, P. Coulie, T. Boon and P. van der Bruggen, 1995. BAGE: a new gene encoding an antigen recognized on human melanomas by cytolytic T lymphocytes. *Immunity* 2:167.

13. Kawakami, Y., S. Eliyahu, C. H. Delgaldo, P. F. Robbins, L. Rivoltni, S. L. Topalian, T. Miki and S. A. Rosenberg, 1994. Cloning of the gene coding for a shared human melanoma antigen recognized by autologous T cells infiltrating into tumor. *Proc. Natl. Acad. Sci. USA* 91:3515.

14. Coulie, P. G., V. Brichard, A. Van Pel. T. Wolfe, J. Schneider, C. Traversari, S. Mattei, E. D. De Plaen, C. Lurquin, J. P. Szikora, J. C. Reauld and T. Boon, 1994. A new gene coding for a differentiation antigen recognized by autologous cytolytic T lymphocytes on HLA-A2 melanomas. *J. Exp. Med.* 180:35.

15. Kawakami, Y., S. Eliyahu, C. H. Delgado, P. F. Robins, K. Sakaguchi, E. Appella, J. R. Yannelli, G. J. Adema, T. Miki and S. A. Rosenberg, 1994. Identification of a human melanoma antigen recognized by tumor infiltrating lymphocytes associated with in vivo tumor rejection. *Proc. Natl. Acad. Sci. USA* 91:6458.

16. Brichard, V., A. Van Pel, T. Wölfel, E. De Plaen, B. Lethë, P. Coulie and T. Boon, 1993. The tyrosinase gene codes for an antigen recognized by autologous cytolytic T lymphocytes on HLA-A2 melanomas. *J. Exp. Med.* 178: 489.

17. Robbins, P. F., M. El-Gamil, Y. Kawakami, E. Stevens, J. Yannelli and S. A. Rosenberg, 1994. Recognition of tyrosinase by tumor infiltrating lymphocytes from a patient responding to immunotherapy. *Cancer Res.* 54:3124.

18. Wang, R. F., P. F. Robbins, Y. Kawakami, X. Q. Kang and S. A. Rosenberg, 1995. Identification of a gene encoding a melanoma tumor antigen recognized by HLA-A31-restricted tumor-infiltrating lymphocytes. *J. Exp. Med.* 181:799.

19. Wang, R. F., E. Appella, Y. Kawakami, X. Q. Kang and S. A. Rosenberg, 1995. Identification of TRP-2 as a human tumor antigen recognized by cytotoxic T lymphocytes. *J. Exp. Med.* 184:2207.

20. Wolfel, T., M. Hauer, J. Schneider, M. Serrano, C. Wolfel, E. Klehmann-Hieb, E. De Plaen, T. Hankein, K. H. Meyer Zum Buschenfeld and D. Beach, 1995. A p16INK4a-insensitive CDK4 mutant targeted by cytolytic T lymphocytes in a human melanoma. *Science* 269:1281.

21. Robbins, P. F., M. El-Gamil, Y. F. Li, Y. Kawakami, D. Loftus, E. Appella and S. A. Rosenberg, 1996. A mutated β-catenin gene encodes a melanoma-specific antigen recognized by tumor infiltrating lymphocytes. *J. Exp. Med.* 183:1185.

22. Coulie, P. G., F. Lehmann, B. Lethe, J. Herman, C. Lurquin, M. Andrawiss and T. Boon, 1995. A mutated intron sequence codes for an antigenic peptide recognized by cytolytic T lymphocytes on a human melanoma. *Proc. Natl. Acad. Sci. USA* 92:7976.

23. Mandruzzato, S., F. Brasseur, G. Andry, T. Boon and P. van der Bruggen, 1997. A CASP-8 mutation recognized by cytolytic T lymphocytes on a human head and neck carcinoma. *J. Exp. Med.* 186:785.

24. Wang, R. F., M. R. Parkhurst, Y. Kawakami, P. F. Robbins and S. A. Rosenberg, 1996. Utilization of an alternative open reading frame of a normal gene in generating a novel human cancer antigen. *J. Exp. Med.* 183:1131.

25. Bloom, M. D., D. Perry-Lalley, P. F. Robbins, Y. Li, M. El-Gamil, S. A. Rosenberg and J. C. Yand, 1997. Identification of tyrosinase-related protein 2 as a tumor rejection antigen for the B16 melanoma. *J. Exp. Med.* 185:453.

26. Disis, M. L., J. W. Smith, A. E. Murphy, W. Chen and M. A. Cheever, 1994. In vitro generation of human cytotoxic T-cells specific for peptides derived from the HER-2/new protooncogene protein. *Cancer Res.* 54:1071.

27. Fisk. B., B. Chesak, J. S. Pollack, J. T. Wharton and C. G. Ioannides, 9114. Oligopeptide induction of a cytotoxic T lymphocyte response to HER-2/Neu proto-oncogene in vitro. *Cell Immunol.* 157:415.

28. Peoples, G. E., 1. Yosino, C. C. Douville, J. V. R. Andrews, P. S. Goedegebuure and T. J. Eberlein, 1994. TCR Vβ3$^+$ and Vβ6$^+$ CTL recognized tumor-associated antigens related to HER-2/neu expression in HLA-A2$^+$ ovarian cancers. *J. Immunol.* 152:4993.

29. Chen Y.-T., M. J. Scanlan, U. Sahin, O. Tureci, A. O. Gure, S. Tsang, B. Williamson, E. Stockert, M. Pfreundschuh and L. J. Old. 1997. A testicular antigen aberrantly expressed in human cancers detected by autologous antibody screening. *Proc. Natl. Acad. Sci. USA* 94:1914.

30. Topalian, S., D. Solomon, F. P. Avis, A. E. Chang, D. L. Freeksen, W. M. Linehan, M. T. Lotze, C. N. Robertson, C. A. Seipp, P. Simon, C. G. Simpson and S. A. Rosenberg, 1988. Immunotherapy of patients with advanced cancer using tumor infiltrating lymphocytes and recombinant interleukin-2: a pilot study, *J. Clin. Oncol.* 6:839.

31. Wang. R. F., S. Johnston, S. Southwood, A. Sette and S. A. Rosenberg, 1998.d Recognition of an antigenic peptide derived from TRP-2 By cytotoxic T lymphocytes in the context of HLA-A31 and -A33. *J. Immunol.* 160:890.

32. Riddell, S. R. and P. D. Greenberg, 1995. Principles for adoptive T cell therapy of human viral diseases. *Annu. Rev. Immunol.* 13:545.

33. Rammensee, H. G., T. Friede and S. Stevanoviic, 1995. MHC ligands and peptide motifs: first listing. *Immunogenetics* 41:178.

34. Baker, P. J., K. L. Britton, P. C. Engel, G. W. Farrants, K. S. Lilley, D. W. Rice and T. J. Stillman, 1992. Subunit assembly and active site location in the structure of glutamate dehydrogenase. *Proteins* 12:75.

35. Jager, E., Y.-T. Chen, J. W. Drijfout, J. Karbach, M. Ringhoffer, D. Jager, M. Arand, H. Wada, Y. Noguchi, E. Stockert, L. J. Old and A. Knuth, 1998. Simultaneous humoral and cellular immune response against cancer-testis antigen NY-ESO-1: definition of human histocompatibility leukocyte antigen (HLA)-A2-binding peptide eptiopes. *J. Exp. Med.* 187:265.

36. Sahin, U., O. Tureci, H. Schmitt, B. Cochlovius, T. Johannes, R. Schmits, F. Stenner, G. Luo, I. Schobert and M. Pfreundschuh, 1995. Human neoplasms elicit multiple immune responses in the autologous host. *Proc. Natl. Acad. Sci. USA* 92:11810.

37. Mattes, J. J., T. M. Thomson, L. J. Old and K. O. Lloyd, 1983. A pigmentation-associated, differentiation antigen of human melanoma defined by a precipitating antibody in human serum. *Int. J. Cancer* 32:717.

38. Kozlowski, S., M. Corr, M. Shirai, L. F. Boyd, C. D. Pendleton, J. A. Berzofsky and D. H. Margulies, 1993. Multiple pathways are involved in the extracellular processing of MHC class I-restricted peptides. *J. Immunol.* 151:4033.
39. Parkhurst, M. R., M. Salgaller, S. Southwood, P. Robbins, A. Sette, S. A. Rosenberg and Y. Kawakami, 1996. Improved induction of melanoma reactive CTL with peptides from the melanoma antigen gp100 modified at HLA-A0201 Binding residues. *J. Immunol.* 157:2539.
40. Fischer, F., D. Peng, S. T. Hingley, S. R. Weiss and P. S. Masters, 1997. The internal open reading frame within the nucleocapside gene of mouse hepatitis virus encodes a structural protein that is not essential for viral replication. *J. Virol.* 71:996.
41. Quelle, D. E., F. Zindy, R. A. Ashmun and C. J. Sherr, 1995. Alternative reading frames of the INK4a tumor suppressor gene encode two unrelated proteins capable of inducing cell cycle arrest. *Cell* 83:993.
42. Kamijo, T., F. Zindy, M. F. Roussel, D. E. Quelle, J. R. Downing, R. A. Ashmun, G. Grosveld and C. J. Sheer, 1997. tumor suppression at the mouse INK4a locus mediated by the alternative reading frame product p19$^{ARF}$. *Cell* 91:649.
43. Kozak, M. 1994. Determinants of translational fidelity and efficiency in vertebrate mRNAs. *Biochimie* 76:815.
44. Bullock, T. N. J. and L. C. Eisenlohr, 1996. ribosomal scanning past the primary initiation codon as a mechanism for expression of CTL epitopes encoded in alternative reading frames. *J. Exp. Med.* 184:1319.
45. Elliott, T., H. Bodmer and A. Townsend, 1996. Recognition of out-of-frame major histocompatibility complex class I-restricted epitopes in vivo. *Eur. J. Immunol.* 26:1175.
46. Uenaka, A., T. Ono, T. Akisawa, H. Wada, T. Yasuda and E. Nakayama, 1994. Identification of a unique peptide pRL1 on BALB/c RL male 1 leukemia recognized by cytotoxic T lymphocytes and its relation to the aki onogene. *J. Exp. Med.* 180:1599.
47. Shastri, N., V. Nguyen and F. Gonzalez, 1995. Major histocompatibility class I molecules can present cryptic translation products to T cells. *J. Biol. Chem.* 270:1088.
48. Malarkannan, S., M. Afkarian and N. Shastri, 1995. A rare cryptic translation product is presented by $K^b$ major histocompatibility complex class I molecule to alloreactive T cells. *J. Exp. Med.* 182:1739.
49. Guilloux, Y., L. Lucas, V. G. Brichard, A. Van Pel, C. Viret, E. De Plaen, F. Brasseur, B. Lethe, F. Jotereau and T. Boon, 1996. A peptide recognized by human cytolytic T lymphocytes on HLA-A2 melanomas is encoded by an intron sequence of the N-acetylglucosaminyltransferase V. gene. *J. Exp. Med.* 183:1173.
50. Robbins, P. F., M. El-Gamil, Y. F. Li, E. Fitzgerald, Y. Kawakami and S. A. Rosenberg, 1997. The intronic region of an incompletely spliced gp100 gene transcript encodes an epitope recognized by melanoma-reactive tumor-in-filtrating lymphocytes. *J. Immunol.* 159:303.

The invention claimed is:

1. An isolated cancer peptide consisting of (a) (i) amino acids 53–62 of SEQ ID NO: 4, (ii) amino acids 127–136 of SEQ ID NO: 4, or (iii) a functionally equivalent variant of (i), wherein the functionally equivalent variant has at least 90% sequence identity with amino acids 53–62 of SEQ ID NO: 4, (iv) amino acids 52–62 of SEQ ID NO: 4, (v) amino acids 51–62 of SEQ ID NO: 4, (vi) amino acids 50–62 of SEQ ID NO: 4, (vii) amino acids 49–62 of SEQ ID NO: 4, or (viii) amino acids 48–62 of SEQ ID NO: 4, wherein said cancer peptide or functionally equivalent variant stimulates cancer antigen specific cytotoxic T lymphocytes.

2. The isolated cancer peptide of claims, wherein the cytotoxic T lymphocytes are restricted by a Major Histocompatibility Complex (MHC) molecule.

3. The isolated cancer peptide of claim 2, wherein the MHC molecule is an MHC class I molecule.

4. The isolated cancer peptide of claim 1, wherein the cancer peptide is expressed by a cell of a cancer selected from the group consisting of: a non-Hodgkins lymphoma, leukemia, Hodgkins lymphoma, lung cancer, liver cancer, metastases, melanoma, adenocarcinoma, thymoma, colon cancer, uterine cancer, breast cancer, prostate cancer, ovarian cancer, cervical cancer, bladder cancer, kidney cancer, pancreatic cancer and sarcoma.

5. The isolated cancer peptide of claim 4, wherein the isolated cancer peptide is presented by a primary breast tumor cell or by a melanoma cell.

6. The isolated cancer peptide of claim 1, wherein the isolated cancer peptide consists of amino acids 53–62 of SEQ ID NO: 4.

7. The isolated cancer peptide of claim 1, wherein the isolated cancer peptide consists of amino acids 48–62 of SEQ ID NO: 4.

8. A composition comprising the cancer peptide of claim 1.

9. An immunogen comprising the composition of claim 8 alone or in combination with at least one immunostimulatory molecule, wherein the immunogen elicits a response by an antigen specific T lymphocyte.

10. The immunogen of claim 9, wherein the immunostimulatory molecule is an MHC molecule.

11. The isolated cancer peptide of claim 3, wherein the MHC class I molecule is selected from the group consisting of HLA-A31, HLA-A3, HLA-A11, HLA-A33, and HLA-A68.

12. The isolated cancer peptide of claim 11, wherein the MHC class I molecule is HLA-A31.

13. The isolated cancer peptide of claim 1, wherein the functionally equivalent variant consists of amino acids 53–62 of SEQ ID NO: 4 Except that amino acid 54 of SEQ ID NO: 4 is substituted with a different amino acid.

14. The isolated cancer peptide of claim 13, wherein the different amino acid is threonine.

15. The isolated cancer peptide of claim 13, wherein the different amino acid is selected from the group consisting of alanine, isoleucine, valine, and leucine.

16. The isolated cancer peptide of claim 1, wherein the functionally equivalent variant consists of amino acids 53–62 of SEQ ID NO: 4 Except that amino acid 53 of SEQ ID NO: 4 is substituted with a different amino acid.

17. The isolated cancer peptide of claim 16, wherein the different amino acid is valine or threonine.

18. The isolated cancer peptide of claim 1, wherein the isolated cancer peptide consists of amino acids 52–62 of SEQ ID NO: 4.

19. The isolated cancer peptide of claim 1, wherein the isolated cancer peptide consists of amino acids 51–62 of SEQ ID NO: 4.

20. The isolated cancer peptide of claim 1, wherein the isolated cancer peptide consists of amino acids 50–62 of SEQ ID NO: 4.

21. The isolated cancer peptide of claim 1, wherein the isolated cancer peptide consists of amino acids 49–62 of SEQ ID NO: 4.

22. The immunogen of claim 10, wherein the MHC molecule is a MHC Class I molecule.

23. The immunogen of claims 22, wherein the MHC Class I molecule is selected from the group consisting of HLA-A31, HLA-A3, HLA-AL 11, HLA-A33, and HLA-A68.

24. The immunogen of claim 23, wherein the MHC Class I molecule is HLA-A31.

25. The isolated cancer peptide of claim 1, wherein the cancer peptide is 10 amino acids in length.

26. An isolated cancer peptide consisting of a portion of SEQ ID NO: 4, wherein the portion consists of (i) amino acids 55–62 of SEQ ID NO: 4; (ii) amino acids 127–136 of SEQ ID 0: 4; (iii) amino acids 53–62 of SEQ ID NO: 4; (iv) amino acids 48–62 of SEQ ID NO: 4; (v) amino acids 43–62 of SEQ ID NO: 4(vi) amino acids 52–62 of SEQ ID NO: 4; (vii) amino acids 51–62 of SEQ ID NO: 4; (viii) amino acids 50–62 of SEQ ID NO: 4; (ix) amino acids 49–62 of SEQ ID NO: 4; (x) amino acids 53–62 of SEQ ID NO: 4 in which amino acid 54 is substituted with a different amino acid; or (xi) amino acids 54–62 of SEQ ID NO: 4 and an additional amino acid at the N-terminus of amino acids 54–62; wherein said cancer peptide is immunologically recognized by antigen specific cytotoxic T lymphocytes.

27. The isolated cancer peptide of claims 26, wherein the different amino acid is threonine.

28. The isolated cancer peptide of claims 26, wherein the different amino acid is alanine, isoleucine, valine, or leucine.

29. The isolated cancer peptide of claim 26, wherein the additional amino acid is valine or threonine.

30. The isolated cancer peptide of claim 26, wherein the cytotoxic T lymphocytes are restricted by an MHC molecule.

31. The isolated cancer peptide of claim 30, wherein the MHC molecule is an MHC class I molecule.

32. The isolated cancer peptide of claim 31, wherein the MHC class I molecule is selected from the group consisting of HLA-A31, HLA-A3, HLA-A11, HLA-A33, and HLA-A68.

33. The isolated cancer peptide of claim 32, wherein the MHC class I molecule is HLA-A31.

34. The isolated cancer peptide of claim 26, wherein the cancer peptide is expressed by a cell of a cancer selected from the group consisting of a non-Hodgkins lymphoma, leukemia, Hodgkins lymphoma, lung cancer, liver cancer, metastases, melanoma, adenocarcinoma, thymoma, colon cancer, uterine cancer, breast cancer, prostate cancer, ovarian cancer, cervical cancer, bladder cancer, kidney cancer, pancreatic cancer and sarcoma.

35. The isolated cancer peptide of claim 34, wherein the isolated cancer peptide is presented by a primary breast tumor cell or by a melanoma cell.

36. A composition comprising one or more of the isolated cancer peptides of claim 26.

37. An immunogen comprising one or more of the isolated cancer peptides of claim 26, alone or in combination with at least one immunostimulatory molecule, wherein the immunogen elicits a response by an antigen specific T lymphocyte.

38. The immunogen of claim 37, wherein the immunostimulatory molecule is an MHC molecule.

39. The immunogen of claim 38, wherein the MHC molecule is an MHC Class I molecule.

40. The immunogen of claim 39, wherein the MHC Class I molecule is selected from the group consisting of HLA-A31, HLA-A3, HLA-A11, HLA-A33, and HLA-A68.

41. The immunogen of claim 40, wherein the MHC Class I molecule is HLA-A31.

* * * * *

UNITED STATES PATENT AND TRADEMARK OFFICE
CERTIFICATE OF CORRECTION

| | |
|---|---|
| PATENT NO. | : 7,084,239 B1 |
| APPLICATION NO. | : 09/529206 |
| DATED | : August 1, 2006 |
| INVENTOR(S) | : Wang et al. |

It is certified that error appears in the above-identified patent and that said Letters Patent is hereby corrected as shown below:

Column 69, Line 13 Claim 2: "claims" should read -- claim 1 --.

Signed and Sealed this

Twenty-third Day of June, 2009

JOHN DOLL
*Acting Director of the United States Patent and Trademark Office*